(12) United States Patent
Cho et al.

(10) Patent No.: US 9,385,336 B2
(45) Date of Patent: Jul. 5, 2016

(54) ORGANIC LIGHT-EMITTING DEVICE USING A MIXTURE OF ELECTRON TRANSPORTING COMPOUNDS

(71) Applicant: SAMSUNG DISPLAY CO., LTD., Yongin, Gyeonggi-Do (KR)

(72) Inventors: Se-Jin Cho, Yongin (KR); Chang-Ho Lee, Yongin (KR); Dae-Yup Shin, Yongin (KR); Young-Mok Son, Yongin (KR); Il-Soo Oh, Yongin (KR); Hee-Joo Ko, Yongin (KR); Jin-Young Yun, Yongin (KR); Bo-Ra Lee, Yongin (KR); Yeon-Woo Lee, Yongin (KR); Beom-Joon Kim, Yongin (KR); Pyung-Eun Jeon, Yongin (KR); Hyun-Ju Choi, Yongin (KR); Chang-Min Lee, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 0 days.

(21) Appl. No.: 14/267,103

(22) Filed: May 1, 2014

(65) Prior Publication Data

US 2014/0374713 A1    Dec. 25, 2014

(30) Foreign Application Priority Data

Jun. 24, 2013 (KR) .................. 10-2013-0072707

(51) Int. Cl.
*H01L 51/50* (2006.01)
*H01L 51/00* (2006.01)
*C09K 11/06* (2006.01)

(52) U.S. Cl.
CPC ............ *H01L 51/5004* (2013.01); *C09K 11/06* (2013.01); *H01L 51/006* (2013.01); *H01L 51/0061* (2013.01); *H01L 51/5072* (2013.01); *C09K 2211/1011* (2013.01); *C09K 2211/1014* (2013.01); *C09K 2211/1044* (2013.01); *H01L 51/0058* (2013.01); *H01L 51/0067* (2013.01); *H01L 51/0077* (2013.01); *H01L 51/5056* (2013.01); *H01L 2251/308* (2013.01)

(58) Field of Classification Search
None
See application file for complete search history.

(56) References Cited

U.S. PATENT DOCUMENTS

| 6,773,830 B2 | 8/2004 | Aziz et al. |
| 2007/0020483 A1 | 1/2007 | Park et al. |
| 2008/0182129 A1* | 7/2008 | Klubek ............... H01L 51/0052 428/704 |

(Continued)

FOREIGN PATENT DOCUMENTS

| KR | 10-2007-0013002 | 1/2007 |
| KR | 10-0826437 | 4/2008 |

(Continued)

*Primary Examiner* — Erik Kielin
(74) *Attorney, Agent, or Firm* — Lee & Morse, P.C.

(57) ABSTRACT

Provided is an organic light-emitting device including a first electrode, a second electrode disposed opposite to the first electrode, an emission layer disposed between the first electrode and the second electrode, and an electron-transporting layer disposed between the emission layer and the second electrode. The electron-transporting layer includes a first electron-transporting material and a second electron-transporting material. The lowest unoccupied molecular orbital (LUMO) energy level of the first electron-transporting material ($EL_1$) and the lowest unoccupied molecular orbital (LUMO) energy level of the second electron-transporting material ($EL_2$) satisfy the equation $0.1\ eV \leq |EL_1 - EL_2| \leq 0.3\ eV$.

20 Claims, 1 Drawing Sheet

(56) References Cited

U.S. PATENT DOCUMENTS

| | | | |
|---|---|---|---|
| 2009/0079326 A1* | 3/2009 | Seo | H01L 51/5048 313/499 |
| 2010/0117520 A1* | 5/2010 | Begley | C09K 11/06 313/504 |
| 2010/0141122 A1* | 6/2010 | Begley | C07D 209/86 313/504 |
| 2010/0164371 A1 | 7/2010 | Jeong et al. | |
| 2012/0305909 A1 | 12/2012 | Seo et al. | |
| 2014/0197401 A1* | 7/2014 | Kroeber et al. | 257/40 |

FOREIGN PATENT DOCUMENTS

| | | |
|---|---|---|
| KR | 10-2010-0069360 | 6/2010 |
| KR | 10-2011-0018892 | 2/2011 |
| KR | 2011018195 A * | 2/2011 |

* cited by examiner

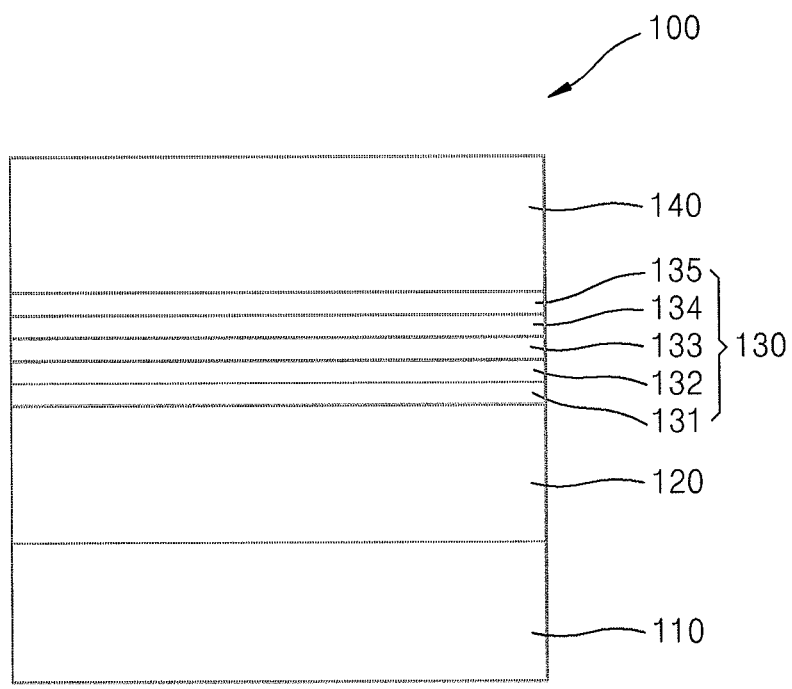

ORGANIC LIGHT-EMITTING DEVICE USING A MIXTURE OF ELECTRON TRANSPORTING COMPOUNDS

CROSS-REFERENCE TO RELATED APPLICATION

The present application claims priority under 35 U.S.C. §119 to Korean Patent Application No. 10-2013-0072707, filed on Jun. 24, 2013, in the Korean Intellectual Property Office, and entitled: "Organic Light-Emitting Device," which is incorporated by reference herein in its entirety.

BACKGROUND

1. Field

The present disclosure relates to an organic light-emitting device.

2. Description of the Related Art

Organic light-emitting devices (OLEDs) are self-emitting devices that have advantages such as wide viewing angles, excellent contrast, quick response time, and excellent brightness, driving voltage, and response speed characteristics, and can provide multicolored images.

A typical OLED has a structure including an anode, a hole-transporting layer (HTL), an emission layer (EML), an electron-transporting layer (ETL), and a cathode, which are sequentially stacked on the substrate. In this regard, the HTL, the EML, and the ETL are organic thin films foamed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. Carriers such as the holes and the electrons recombine in the EML to generate excitons. When the excitons drop from an excited state to a ground state, light is emitted.

SUMMARY

The present disclosure provides an organic light-emitting device simultaneously having a low driving voltage, high efficiency, and a long lifespan.

According to an aspect of the present disclosure, there is provided an organic light emitting device including a first electrode, a second electrode disposed opposite to the first electrode, an emission layer disposed between the first electrode and the second electrode, and an electron-transporting layer disposed between the emission layer and the second electrode. The electron-transporting layer includes a first electron-transporting material and a second electron-transporting material. A lowest unoccupied molecular orbital (LUMO) energy level of the first electron-transporting material ($EL_1$) and a LUMO energy level of the second electron-transporting material ($EL_2$) satisfy the equation, $0.1\ eV \leq |EL_1 - EL_2| \leq 0.3\ eV$.

According to another aspect of the present disclosure, there is provided an organic light-emitting device including a first electrode, a second electrode disposed opposite to the first electrode, an emission layer disposed between the first electrode and the second electrode, and an electron-transporting layer disposed between the emission layer and the second electrode. The electron-transporting layer includes a first electron-transporting material and a second electron-transporting material. The first electron-transporting material and the second electron-transporting material are each independently selected from an amine-based compound represented by Formula 1 and an anthracene-based compound represented by Formula 2, wherein, such that the first electron-transporting material and the second electron-transporting material are different.

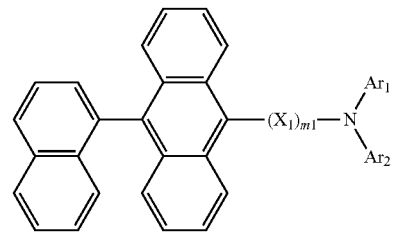

<Formula 1>

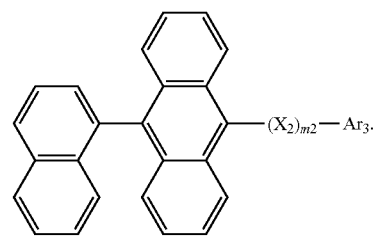

<Formula 2>

In Formulae 1 and 2, groups represented by $X_1$ and $X_2$ are each independently selected from a substituted or unsubstituted $C_6$-$C_{60}$ arylene group or a substituted or unsubstituted $C_2$-$C_{60}$ heteroarylene group; m1 and m2 are each independently an integer of 0 to 5.

In Formula 1, groups represented by $Ar_1$ and $Ar_2$ are each independently selected from a substituted or unsubstituted $C_6$-$C_{60}$ aryl group and a substituted or unsubstituted $C_2$-$C_{60}$ heteroaryl group. At least one of the groups represented by $Ar_1$ and $Ar_2$ is selected from i) a pyridyl group, a pyrimidyl group, and a triazinyl group, ii) a pyridyl group, a pyrimidyl group, and a triazinyl group, each of which may be substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group, each of which may be substituted with at least one of a pyridyl group, a pyrimidyl group, and a triazinyl group; and iv) a pyridyl group, a pyrimidyl group, and a triazinyl group, each of which may be substituted with at least one of a $C_6$-$C_{60}$ aryl group and a $C_2$-$C_{60}$ heteroaryl group, each of which may be substituted with at least one of a $C_6$-$C_{60}$ aryl group and a $C_2$-$C_{60}$ heteroaryl group.

In Formula 2, the group represented by $Ar_3$ is selected from i) a pyridyl group, a pyrimidyl group, and a triazinyl group; ii) a pyridyl group, a pyrimidyl group, and a triazinyl group each substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group each substituted with at least one of a pyridyl group, a pyrimidyl group, and a triazinyl group; and iv) a pyridyl group, a pyrimidyl group, and a triazinyl group, each of which may be substituted with at least one of a $C_6$-$C_{60}$ aryl group and a $C_2$-$C_{60}$ heteroaryl group, which are each substituted with at least one of a $C_6$-$C_{60}$ aryl group and a $C_2$-$C_{60}$ heteroaryl group.

BRIEF DESCRIPTION OF THE DRAWINGS

Features will become apparent to those of ordinary skill in the art by describing in detail exemplary embodiments with reference to the attached drawings in which:

FIG. 1 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURES, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

FIG. 1 illustrates a schematic view of a cross-section of an organic light-emitting device 100 according to an embodiment of the present disclosure. A structure and a method of manufacturing an organic light-emitting device according to an embodiment of the present disclosure are described as follows with reference to FIG. 1.

The substrate 110 may be any substrate that is used in existing organic light emitting devices such as a glass substrate or a transparent plastic substrate having strong mechanical strength, thermal stability, transparency, surface smoothness, ease of handling, and water resistance.

The first electrode 120 may be formed on the substrate by depositing or sputtering a first electrode-forming material onto a surface of the substrate 110. When the first electrode 120 is an anode, a material having a high work function may be used as the first electrode-forming material to facilitate hole injection. The first electrode 120 may be a reflective electrode or a transmission electrode. Materials having excellent transparent and conductive capabilities such as indium tin oxide (ITO), indium zinc oxide (IZO), tin oxide ($SnO_2$), and zinc oxide (ZnO) may be used to form the first electrode 120. In other embodiments, magnesium (Mg), aluminum (Al), aluminum-lithium (Al—Li), calcium (Ca), magnesium-indium (Mg—In), magnesium-silver (Mg—Ag), and the like may be used to form the first electrode 120 as a reflective electrode.

The first electrode 120 may have a single layer or a multi-layer structure including two or more layers. For example, the first electrode 120 may have a three-layered structure of ITO/Ag/ITO, but is not limited thereto.

An organic layer 130 is disposed on the first electrode 120. The organic layer 130 refers to a plurality of layers disposed between the first electrode 120 and a second electrode 140 in the organic light-emitting device 100 and may further include an emission layer (EML) 133, a hole-injecting layer (HIL) 131, a hole-transporting layer (HTL) 132, a functional layer having both hole-injecting and hole-transporting capabilities (H-functional layer), a buffer layer, an electron-blocking layer (EBL), a hole-blocking layer (HBL), an electron-transporting layer (ETL) 134, an electron-injecting layer (EIL) 135, and a functional layer having both electron-injecting and electron-transporting capabilities (E-functional layer). According to an embodiment, the organic layer 130 may sequentially include the HIL 131, HTL 132, buffer layer, EML 133, ETL 134, and EIL 135.

The HIL 131 may be formed on the first electrode 120 using various methods, such as vacuum deposition, spin coating, casting, or Langmuir-Blodgett (LB) deposition. When the HIL 131 is formed using vacuum deposition, vacuum deposition conditions may vary according to the compound that is used to form the HIL 131, and the desired structure and thermal properties of the HIL 131 to be formed. For example, vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL 131 is formed using spin coating, the coating conditions may vary according to the compound that is used to form the HIL 131, and the desired structure and thermal properties of the HIL 131 to be formed. For example, the coating rate may be in a range of about 2000 rpm to about 5000 rpm, and a temperature at which heat treatment is performed to remove a solvent after coating may be in a range of about 80° C. to about 200° C. However, the coating conditions are not limited thereto.

The HIL 131 may be formed of any known hole-injecting material, and non-limiting examples of the hole-injecting material are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino) triphenylamine (m-MTDATA), N,N'-di(1-naphthyl group-N,N'-diphenyl-benzidine (NPB), TDATA, 2-TNATA, polyaniline/dodecyl-benzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate) (PANI/PSS).

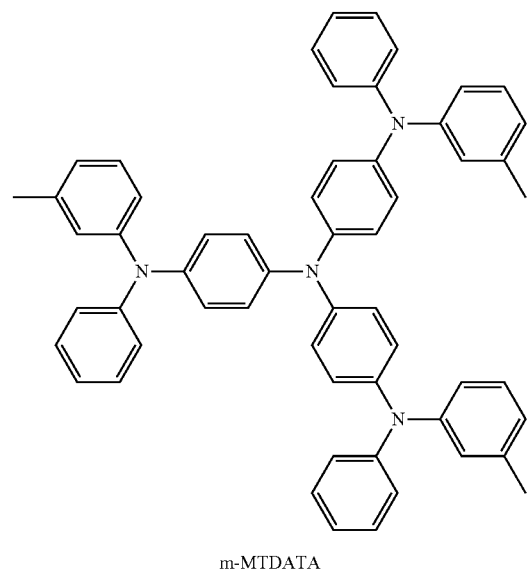

m-MTDATA

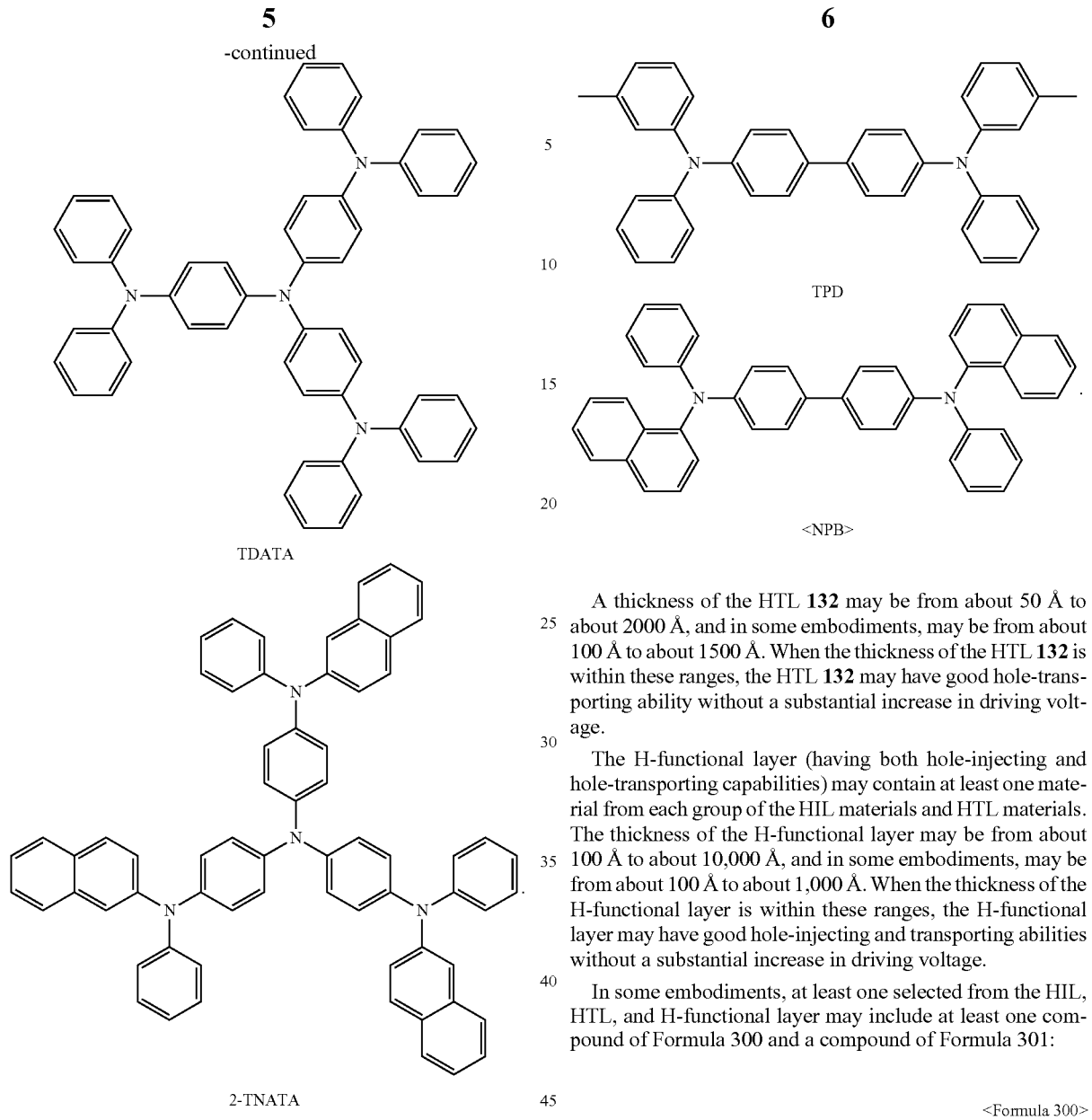

TDATA

2-TNATA

TPD

<NPB>

A thickness of the HIL 131 may be about 100 Å to about 10,000 Å, and in some embodiments, may be from about 100 Å to about 1000 Å. When the thickness of the HIL 131 is within these ranges, the HIL 131 may have good hole-injecting ability without a substantial increase in driving voltage.

Then, the HTL 132 may be formed on the HIL 131 by using various methods, such as vacuum deposition, spin coating, casting, and LB deposition. When the HTL 132 is formed using vacuum deposition or spin coating, the deposition and coating conditions may be similar to those for the formation of the HIL 131, though the conditions for deposition and coating may vary according to the material that is used to form the HTL 132.

Non-limiting examples of known hole-transporting materials may include, for example, carbazole derivatives such as N-phenylcarbazole and polyvinylcarbazole, N,N'-bis(3-methyl phenyl)-N,N'-diphenyl-[1,1-biphenyl]-4,4'-diamine (TPD), 4,4',4"-tris(N-carbazolyl)triphenylamine (TCTA), and N,N'-di(1-naphthyl-N,N'-diphenylbenzidine) (NPB).

A thickness of the HTL 132 may be from about 50 Å to about 2000 Å, and in some embodiments, may be from about 100 Å to about 1500 Å. When the thickness of the HTL 132 is within these ranges, the HTL 132 may have good hole-transporting ability without a substantial increase in driving voltage.

The H-functional layer (having both hole-injecting and hole-transporting capabilities) may contain at least one material from each group of the HIL materials and HTL materials. The thickness of the H-functional layer may be from about 100 Å to about 10,000 Å, and in some embodiments, may be from about 100 Å to about 1,000 Å. When the thickness of the H-functional layer is within these ranges, the H-functional layer may have good hole-injecting and transporting abilities without a substantial increase in driving voltage.

In some embodiments, at least one selected from the HIL, HTL, and H-functional layer may include at least one compound of Formula 300 and a compound of Formula 301:

<Formula 300>

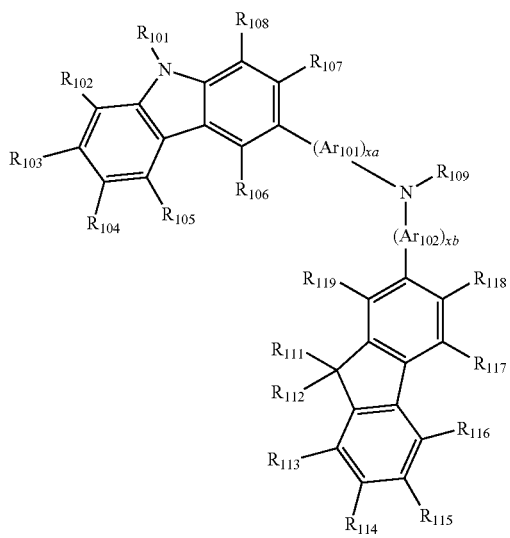

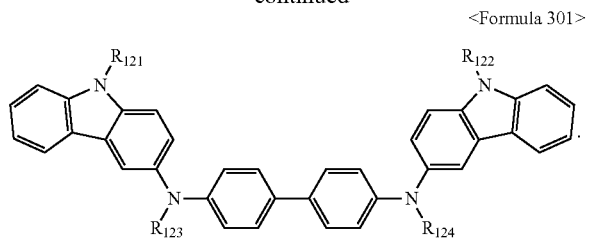

<Formula 301>

In Formula 300, groups represented by $Ar_{101}$ and $Ar_{102}$ may be each independently a substituted or unsubstituted $C_6$-$C_{60}$ arylene group. For example, $Ar_{101}$ and $Ar_{102}$ may be each independently selected from a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylenylene group, a naphthacenylene group, a picenylene group, a perylenylene group, and a pentacenylene group, each of which may be substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

In Formula 300, xa and xb may be each independently an integer of 0 to 5, or 0, 1 or 2. For example, xa may be 1 and xb may be 0, but they are not limited thereto.

In Formulae 300 and 301, groups represented by $R_{101}$ to $R_{108}$, $R_{111}$ to $R_{119}$, and $R_{121}$ to $R_{124}$ may be each independently selected from a hydrogen atom, a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. For example, groups represented by $R_{101}$ to $R_{108}$, $R_{111}$ to $R_{119}$, and $R_{121}$ to $R_{124}$ may be each independently a hydrogen atom, a deuterium atom, a halogen atom, a hydroxyl group, a cyano group, a nitro group, an amino group, an amidino group, hydrazine; hydrazone, a carboxylic acid group or a salt thereof, a sulfonic acid group or a salt thereof, a phosphoric acid or a salt thereof, a $C_1$-$C_{10}$ alkyl group (for example, a methyl group, an ethyl group, a propyl group, a butyl group, a pentyl group, and a hexyl group), a $C_1$-$C_{10}$ alkoxy group (for example, a methoxy group, an ethoxy group, a propoxy group, a butoxy group, and a pentoxy group), a $C_1$-$C_{10}$ alkyl group, and a $C_1$-$C_{10}$ alkoxy group, each of which may be substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof and a phosphoric acid or a salt thereof, a phenyl group, a naphthyl group, an anthryl group, a fluorenyl group, a pyrenyl group, a phenyl group, a naphthyl group, an anthryl group, a fluorenyl group, and a pyrenyl group, each of which substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid or a salt thereof, a $C_1$-$C_{10}$ alkyl group, and a $C_1$-$C_{10}$ alkoxy group, but they are not limited thereto.

In Formula 300, a group represented by $R_{109}$ may be one selected from a phenyl group, a naphthyl group, an anthryl group, a biphenyl group, a pyridyl group, a phenyl group, a naphthyl group, an anthryl group, a biphenyl group, and a pyridyl group, each of which may be substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment, a compound represented by Formula 300 may be represented as Formula 300A, but the compound is not limited thereto:

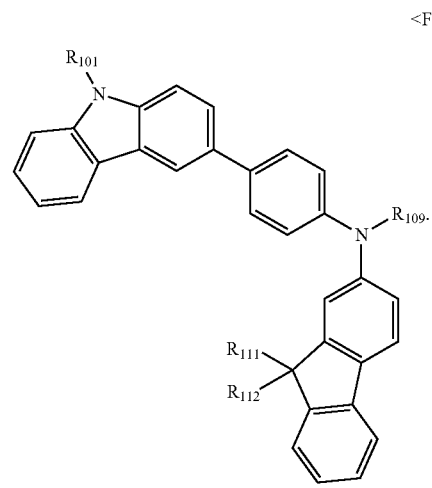

<Formula 300A>

In Formula 300A, descriptions of groups represented by $R_{101}$, $R_{111}$, $R_{112}$, and $R_{109}$ are referred to in the description provided herein. For example, at least one of the HIL 131, HTL 132, and H-functional layer may include at least one of Compounds 301 to 320, but is not limited thereto:

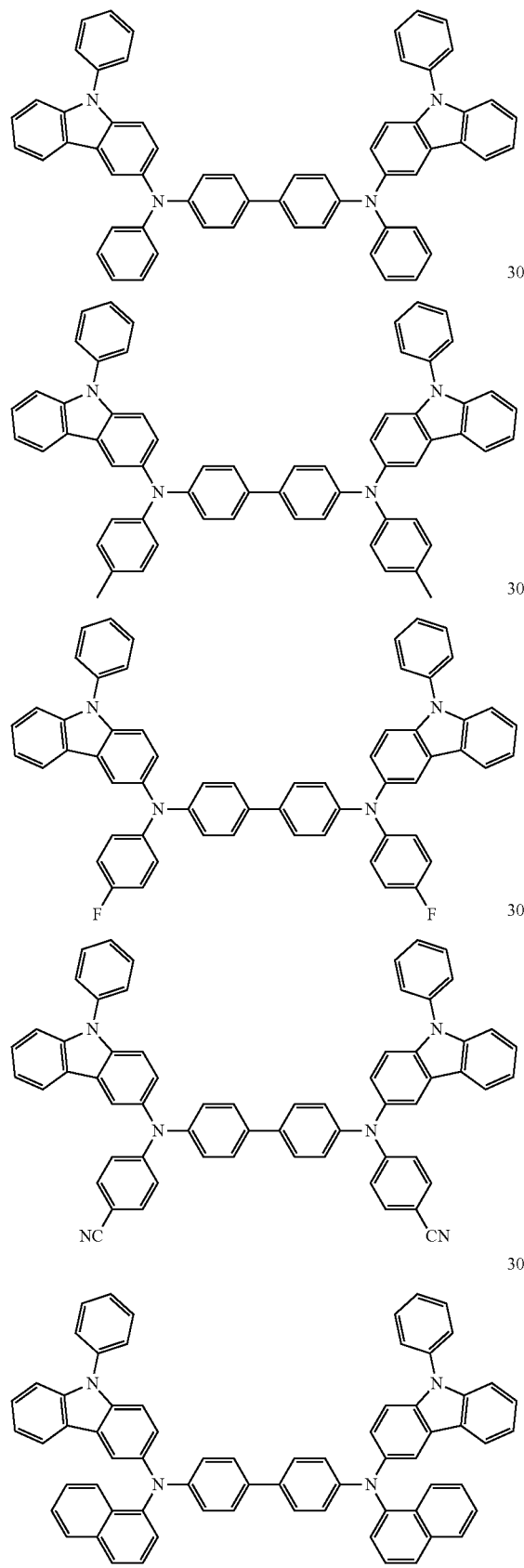
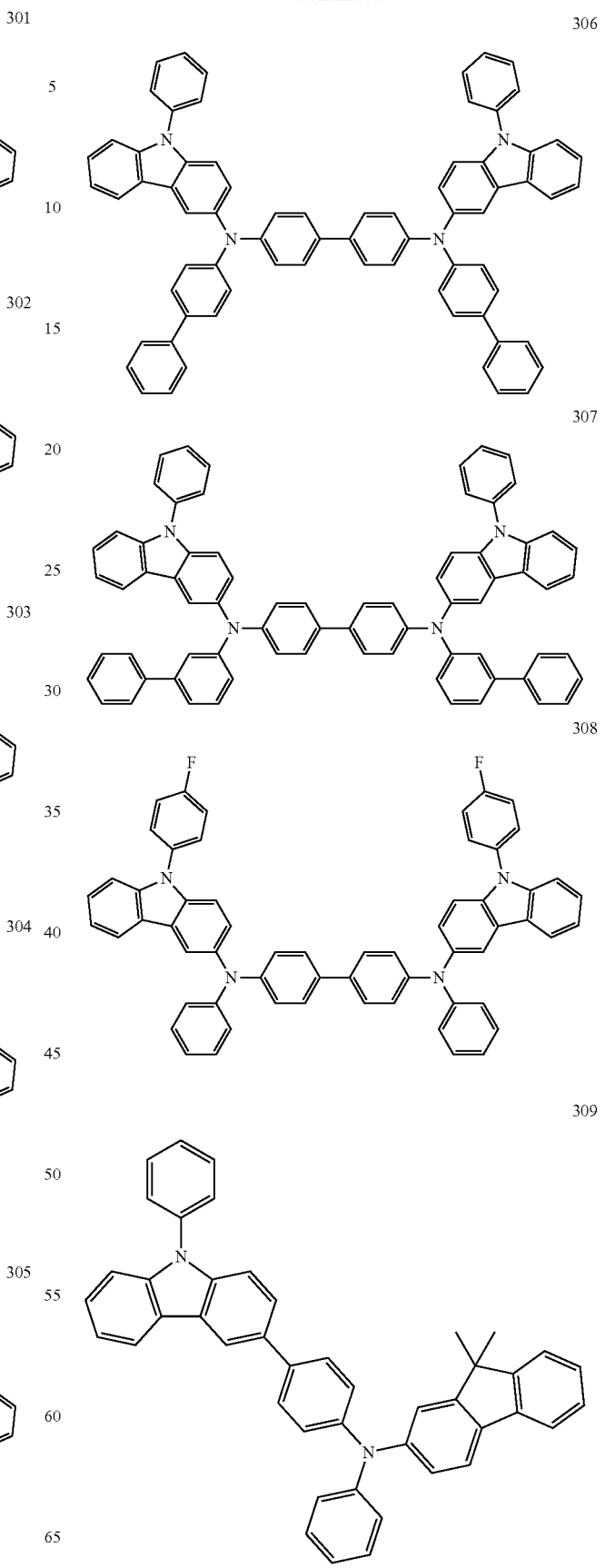

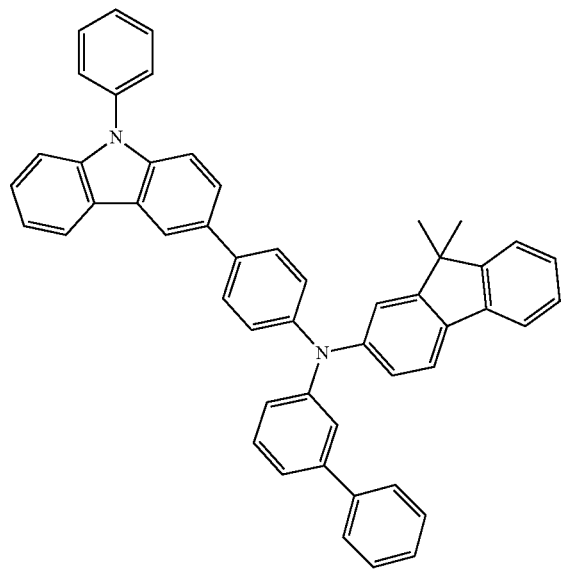
310
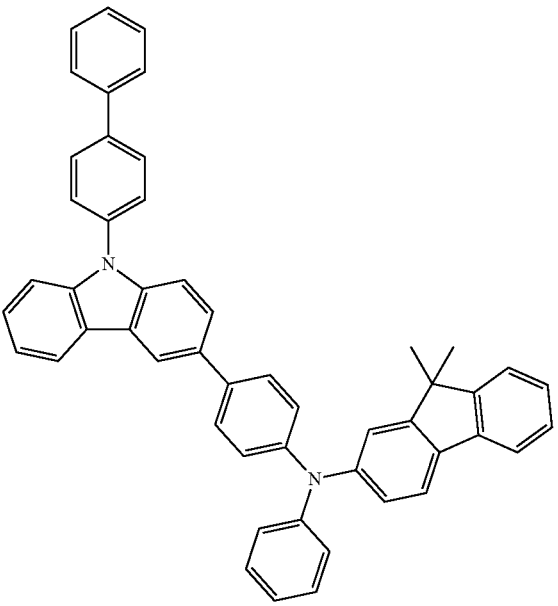
312
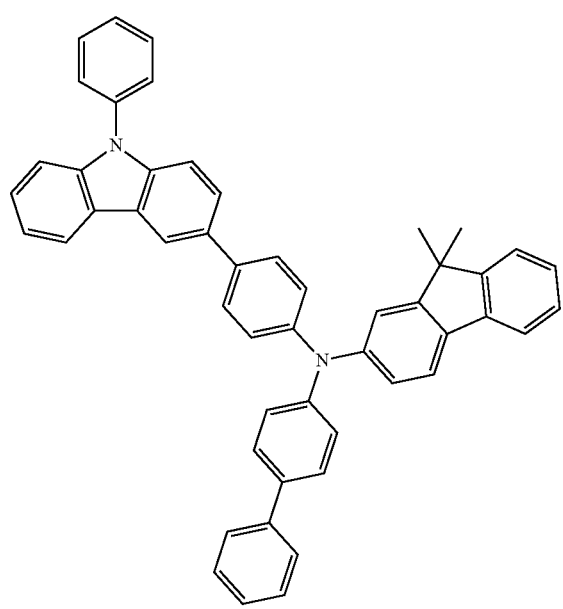
311
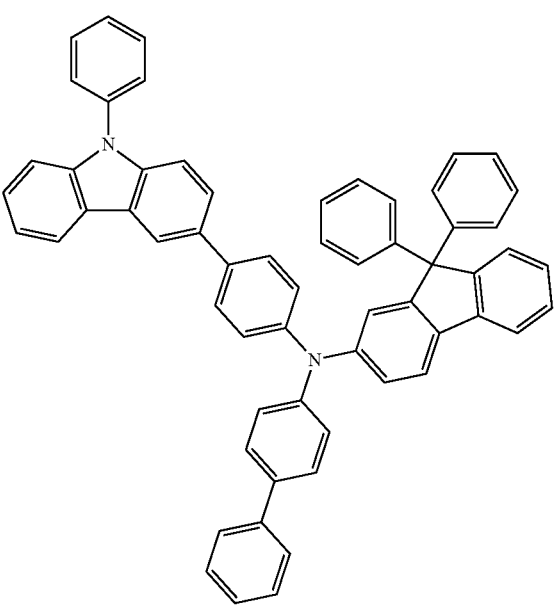
313

314
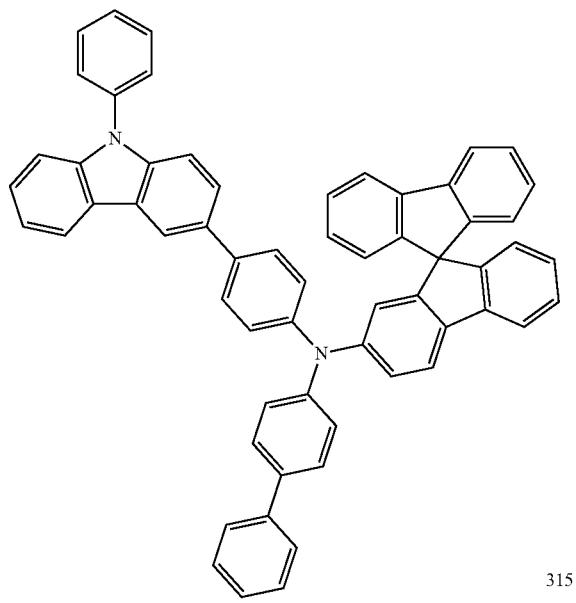
315
317
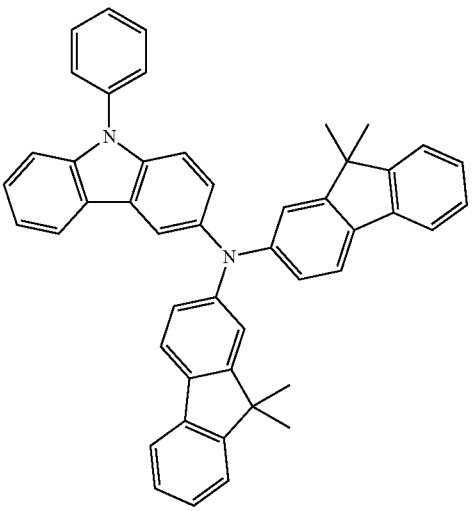
318
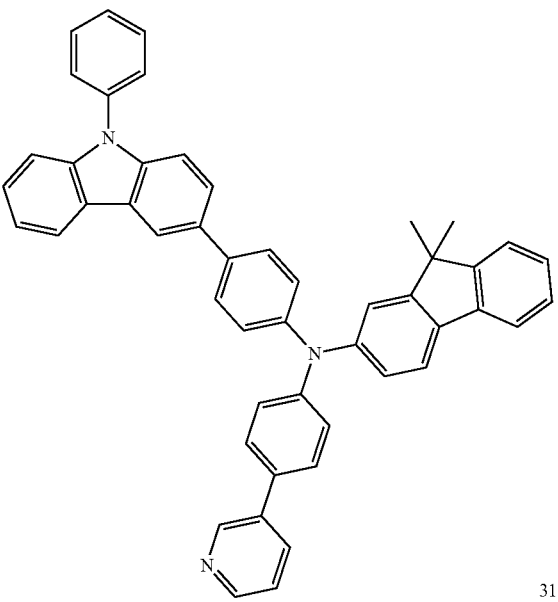
316
319
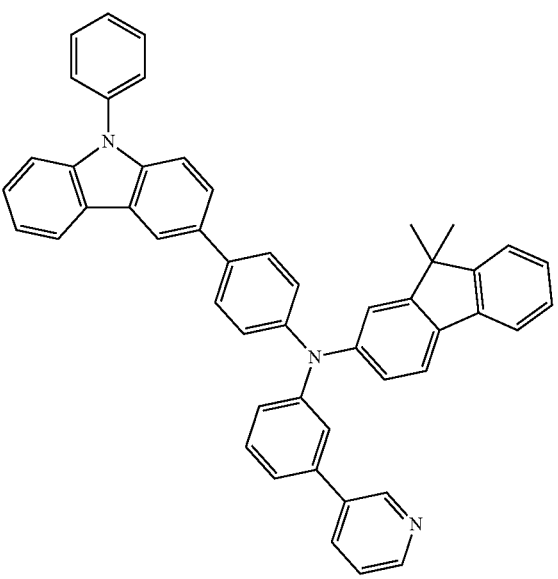

-continued

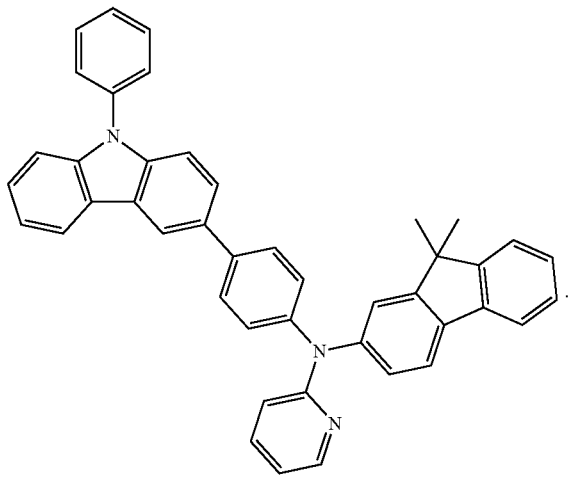

At least one of the HIL 131, HTL 132, and H-functional layer may further include a charge-generating material to improve conductivity of a film and the like, in addition to a known hole-injecting material, a known hole-transporting material, and/or a material having both hole-injecting and hole-transporting capabilities.

The charge-generating material may be, for example, a p-dopant. The p-dopant may be one of a quinone derivative, a metal oxide, and a cyano group-containing compound, but is not limited thereto. Non-limiting examples of the p-dopant are quinone derivatives such as tetracyanoquinonedimethane (TCNQ) and 2,3,5,6-tetrafluoro-tetracyano-1,4-benzoquinonedimethane (F4-TCNQ), metal oxides such as tungsten oxide and molybdenum oxide, and cyano-group-containing compounds such as Compound 200.

<Compound 200>

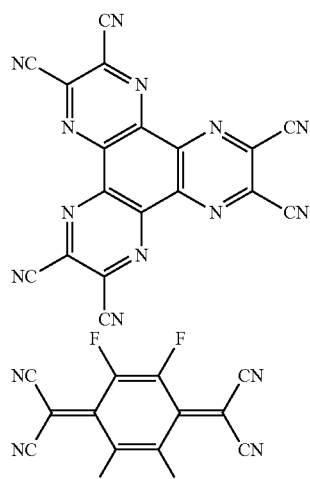

<F4-TCNQ>

When the HIL 131, HTL 132, or the H-functional layer further includes the charge-generating material, the charge-generating material may be homogeneously dispersed or non-homogeneously distributed in the HIL 131, HTL 132, or H-functional layer.

The buffer layer may be disposed between the EML 133 and at least one selected from the HIL 131, HTL 132, and the H-functional layer. The buffer layer may compensate for an optical resonance distance of light according to a wavelength of the light emitted from the EML 133, and thus may increase efficiency. The buffer layer may include any hole-injecting material or hole-transporting material. In some other embodiments, the buffer layer may include the same material as one of the materials included in the HIL 131, HTL 132, and H-functional layer that underlies the buffer layer.

Then, the EML 133 may be formed on the HTL 132, H-functional layer, or buffer layer by vacuum deposition, spin coating, casting, LB deposition, or the like. When the EML 133 is formed using vacuum deposition or spin coating, the deposition and coating conditions may be similar to those for the formation of the HIL 131, though the conditions for deposition and coating may vary according to the material that is used to form the EML 133.

The EML 133 may include a known light-emitting material. The EML 133 may include a known host and a dopant. When the organic light-emitting device is a full color organic light-emitting device, the EML 133 may be patterned into a red EML, a green EML, and a blue EML. In some embodiments, the EML 133 may include at least two of the red EML, the green EML, and the blue EML that are stacked upon one another to emit white light, but is not limited thereto.

Non-limiting examples of the known host are tris(8-quinolinato)aluminum (Alq$_3$), 4,4'-N,N'-dicarbazole-biphenyl (CBP), poly(n-vinylcarbazole) (PVK), 9,10-di(naphthalene-2-yl)anthracene (ADN), 4,4',4"-tris(carbazole-9-yl)triphenylamine (TCTA), 1,3,5-tris(N-phenylbenzimidazole-2-yl)benzene (TPBI), 3-tertert-butyl-9,10-di(napth-2-yl)anthracene (TBADN), 9,9'-(1,3-phenylene)bis-9H-carbazole (mCP), E3, 1,3-bis[2-(4-tert-butyphenyl)-1,3,4-oxadiazo-5-yl] (OXD-7), distyryl arylene (DSA), dmCBP, and Compounds 501 to 509, but are not limited thereto.

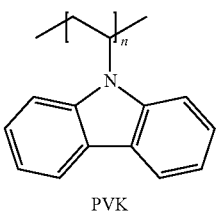

PVK

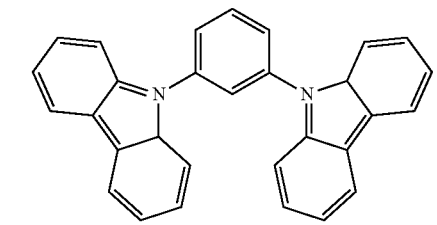

mCP

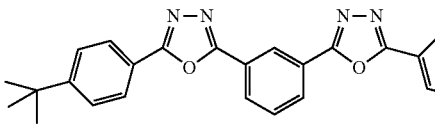

OXD-7

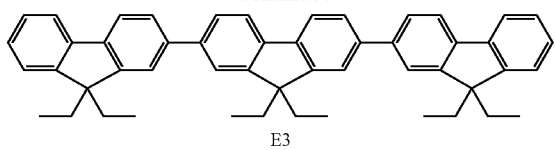
E3
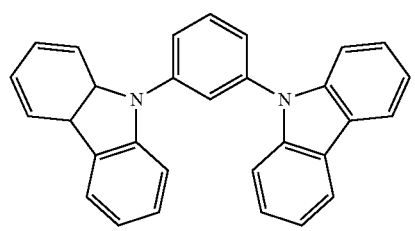
dmCBP
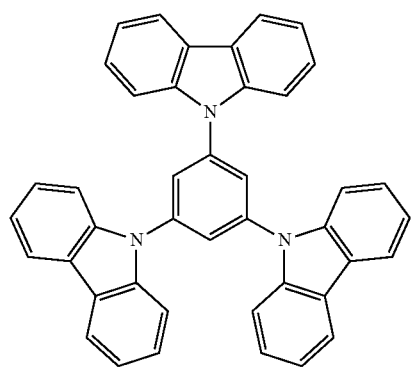
501
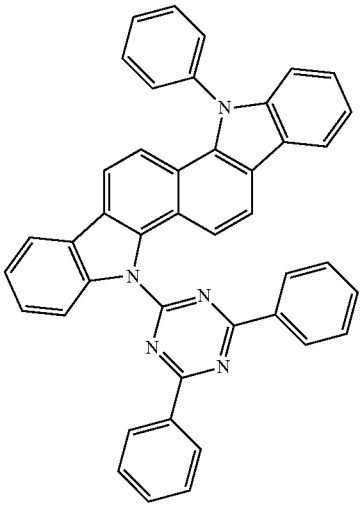
504
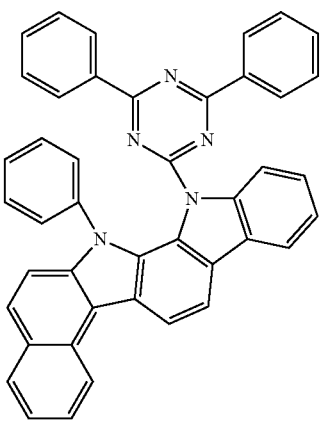
505
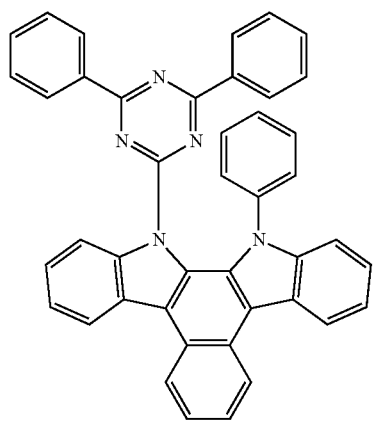
502
503
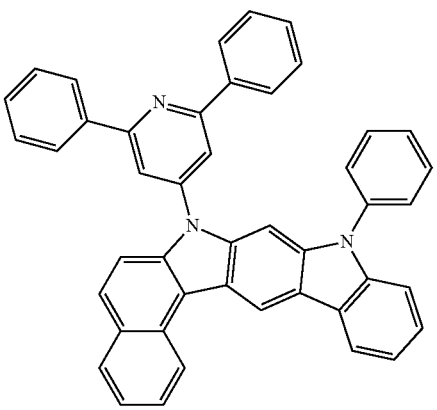
506

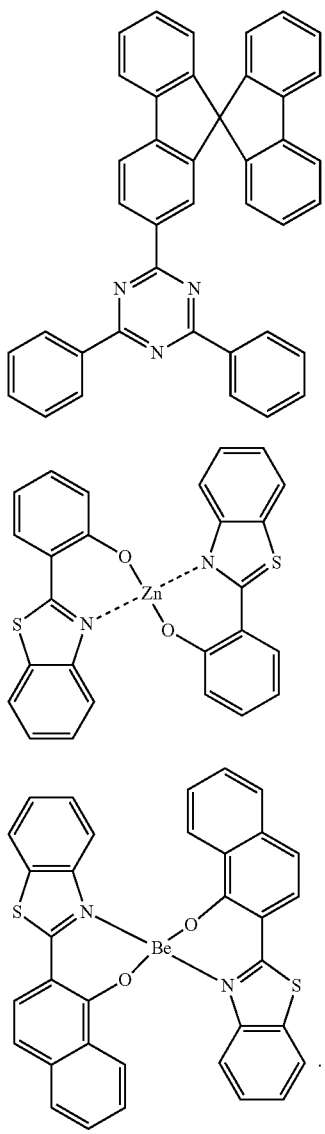

In some embodiments, as the host, an anthracene-based compound represented by Formula 400 may be used:

<Formula 400>

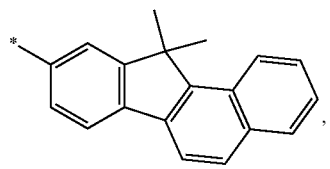 [SMILES: *c1ccc2c(c1)C(C)(C)c1c-2ccc2ccccc12]

In Formula 400, groups represented by $Ar_{111}$ and $Ar_{112}$ are each independently a substituted or unsubstituted $C_5$-$C_{60}$ arylene group; groups represented by $Ar_{113}$ to $Ar_{116}$ are each independently a substituted or unsubstituted $C_1$-$C_{10}$ alkyl group or a substituted or unsubstituted $C_5$-$C_{60}$ aryl group; and g, h, i, and j may be each independently an integer of 0 to 4. In some embodiments, in Formula 400, groups represented by $Ar_{111}$ and $Ar_{112}$ may be each independently a phenylene group, a naphthylene group, a phenanthrenylene group, or a pyrenylene group; or a phenylene group, a naphthylene group, a phenanthrenylene group, a fluorenyl group, or a pyrenylene group, each of which may be substituted with at least one selected from a phenyl group, a napthyl group, and an anthryl group, but are not limited thereto. In Formula 400, g, h, i, and j may be each independently an integer of 0, 1, or 2.

In Formula 400, groups represented by $Ar_{113}$ to $Ar_{116}$ may be each independently a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group, each of which may be substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

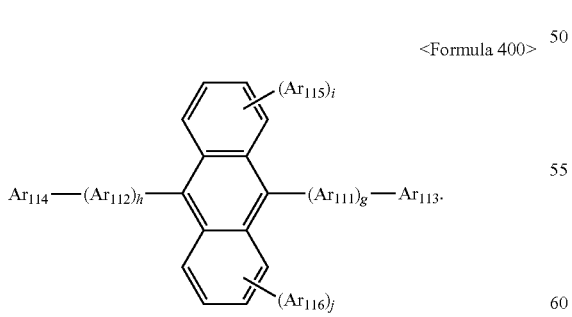

but are not limited thereto.

In some embodiments, an anthracene-based compound represented by Formula 400 may be one of the following compounds, but is not limited thereto:

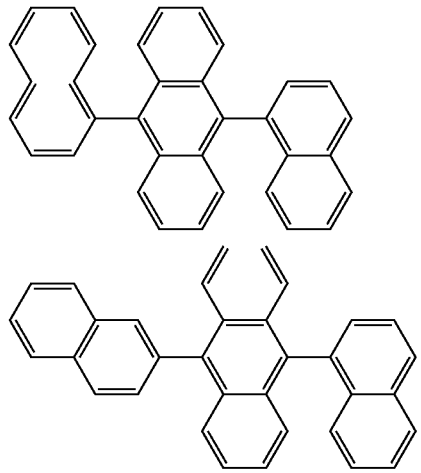

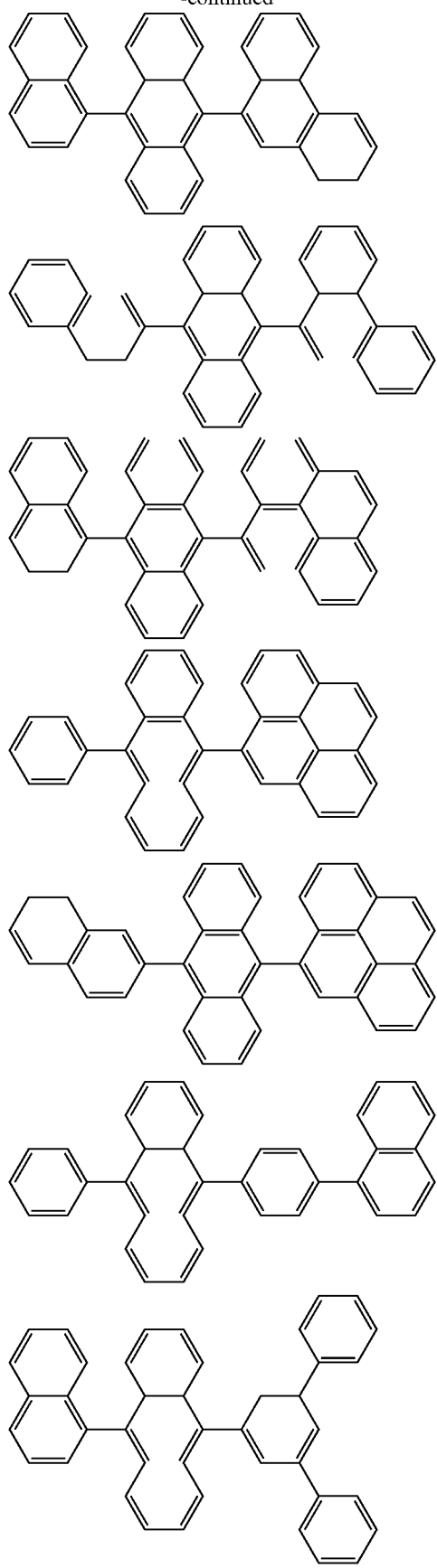
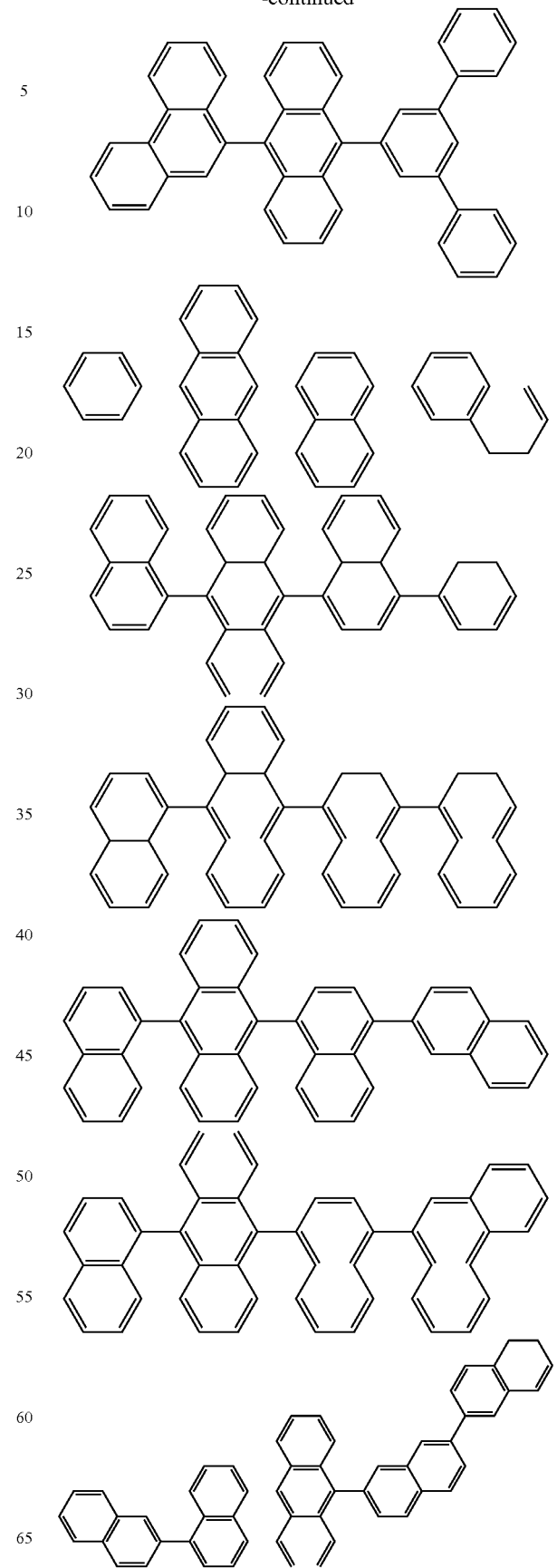

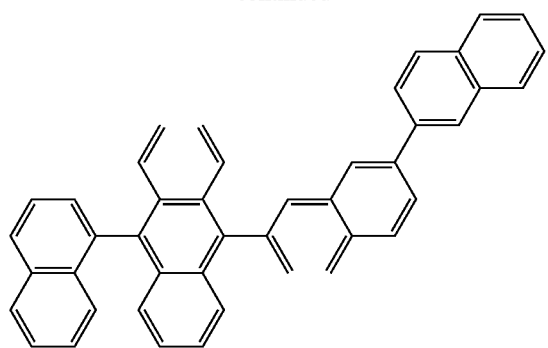
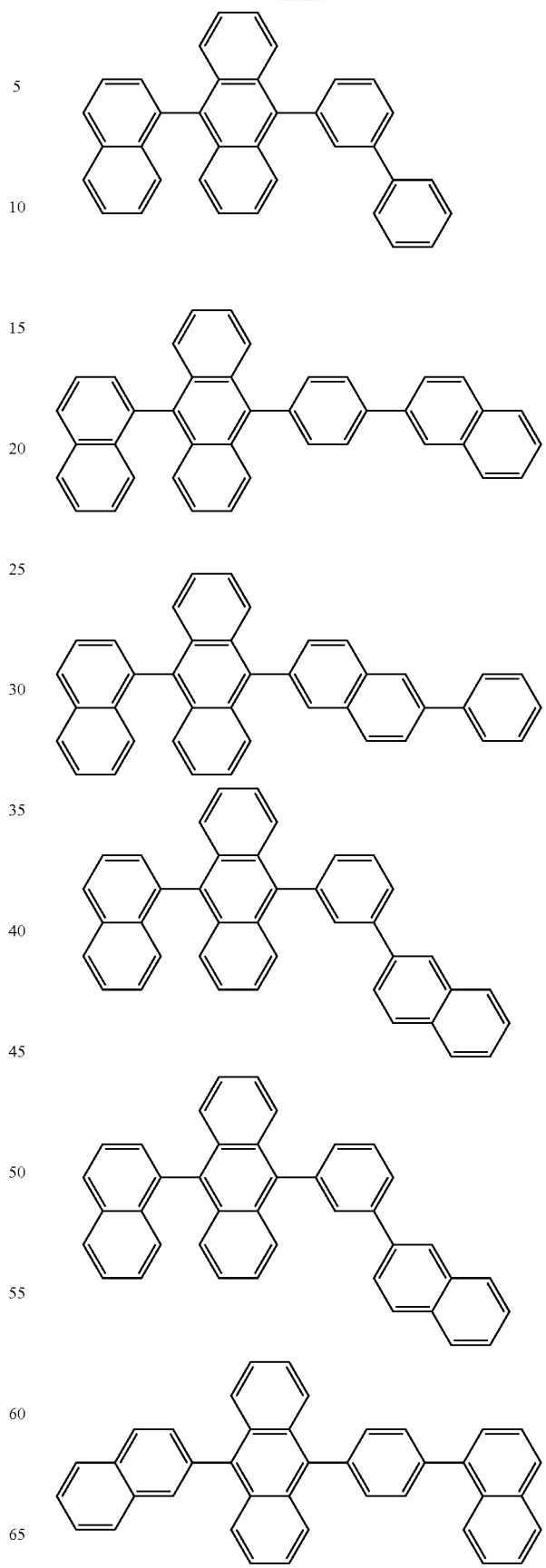

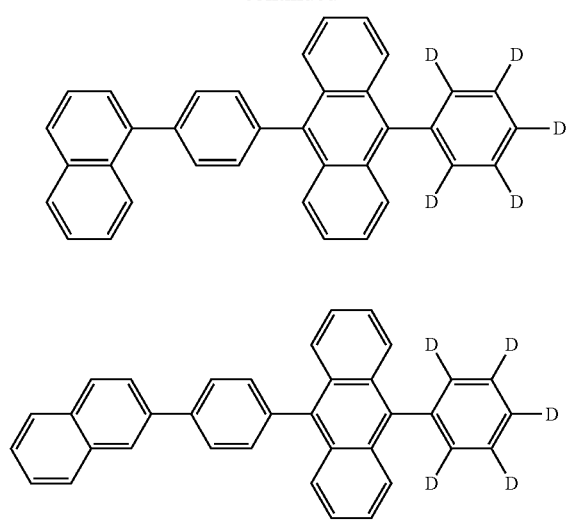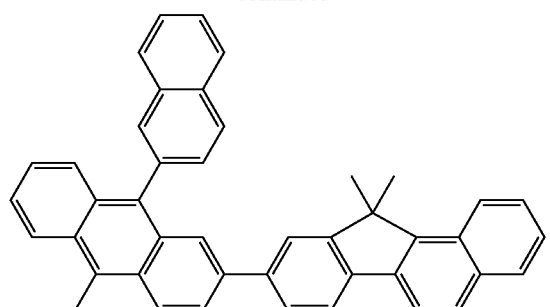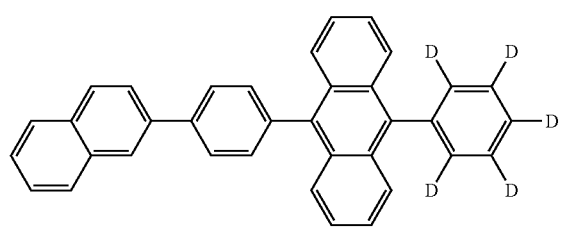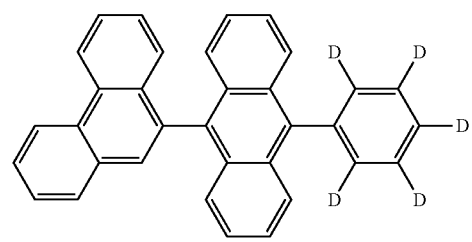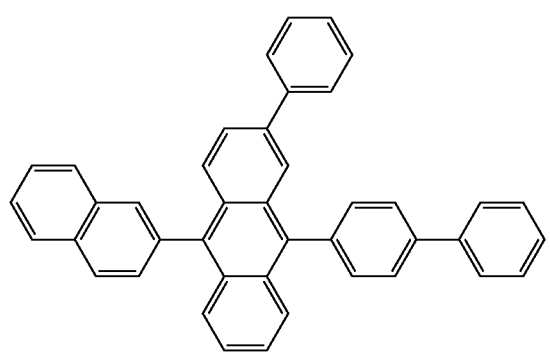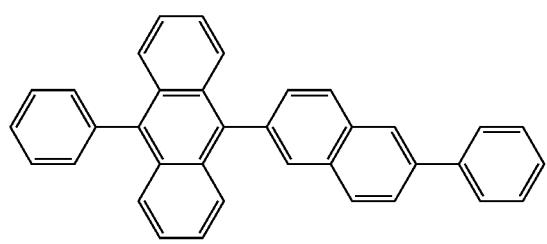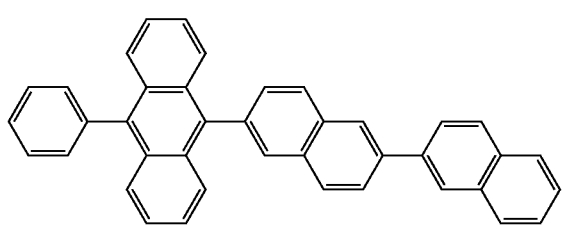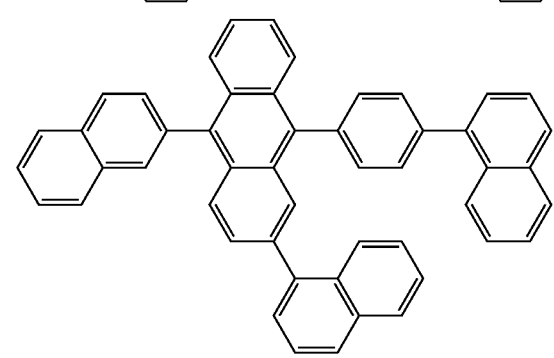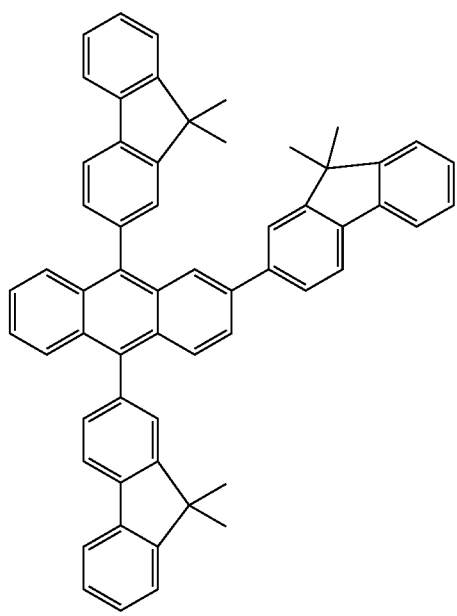

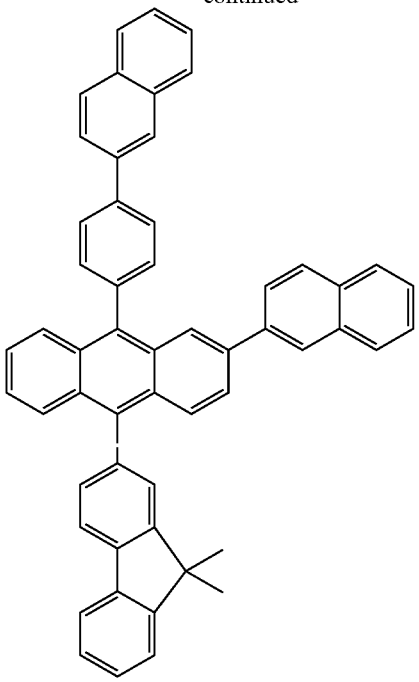

In some embodiments, as the host, an anthracene-based compound represented by Formula 401 may be used:

<Formula 401>

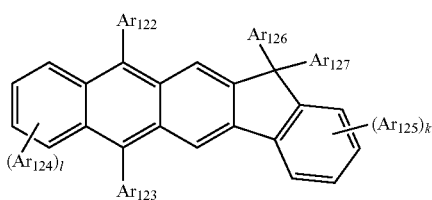

In Formula 401, detailed descriptions of groups represented by $Ar_{122}$ to $Ar_{125}$ are as referred to in the description of the group represented by $Ar_{113}$ of Formula 400.

In Formula 401, groups represented by $Ar_{126}$ and $Ar_{127}$ may be each independently a $C_1$-$C_{10}$ alkyl group (for example, a methyl group, an ethyl group, or a propyl group).

In Formula 401, k and l may be each independently an integer of 0 to 4. For example, the k and l may be 0, 1, or 2. For example, the anthracene-based compound represented by Formula 401 may be one of the following compounds, but is not limited thereto:

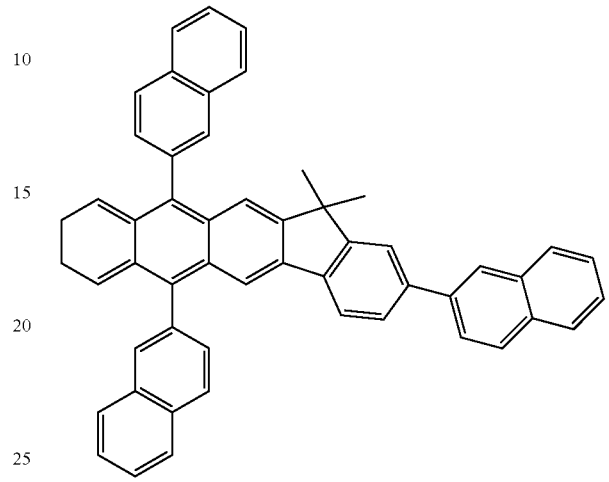

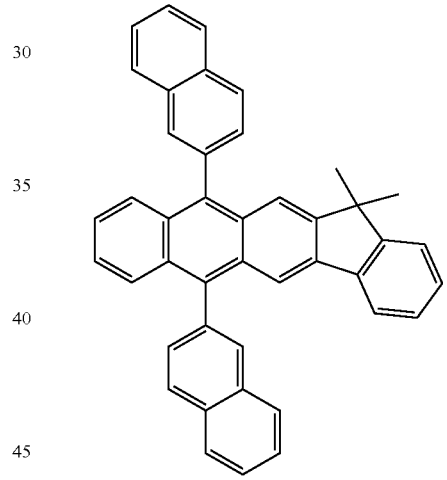

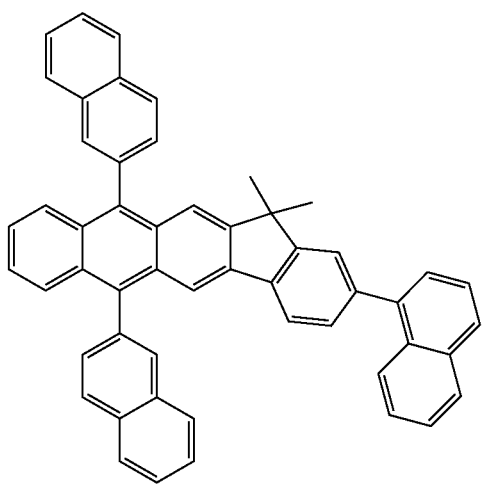

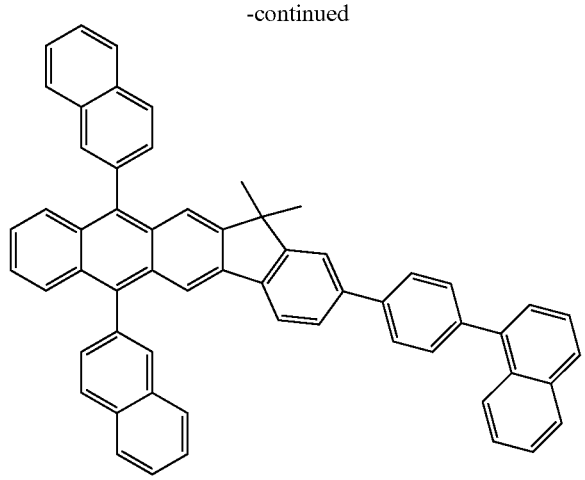

The dopant may be at least one selected from a fluorescent dopant and a phosphorescent dopant. The phosphorescent dopant may be an organic metal complex including Ir, Pt, Os, Re, Ti, Zr, Hf, or a combination of two or more of these, but is not limited thereto.

Non-limiting examples of known blue dopants are $F_2$Irpic, $(F_2\ ppy)_2$Ir(tmd), Ir(dfppz)$_3$, ter-fluorene (fluorene), 4,4'-bis(4-diphenyl aminostyryl) biphenyl (DPAVBi), 2,5,8,11-tetra-tertert-butyl perylene (TBPe), and 4,4'-bis(2,2-diphenyl vinyl)-1,1'-biphenyl (DPVBi), but are not limited thereto.

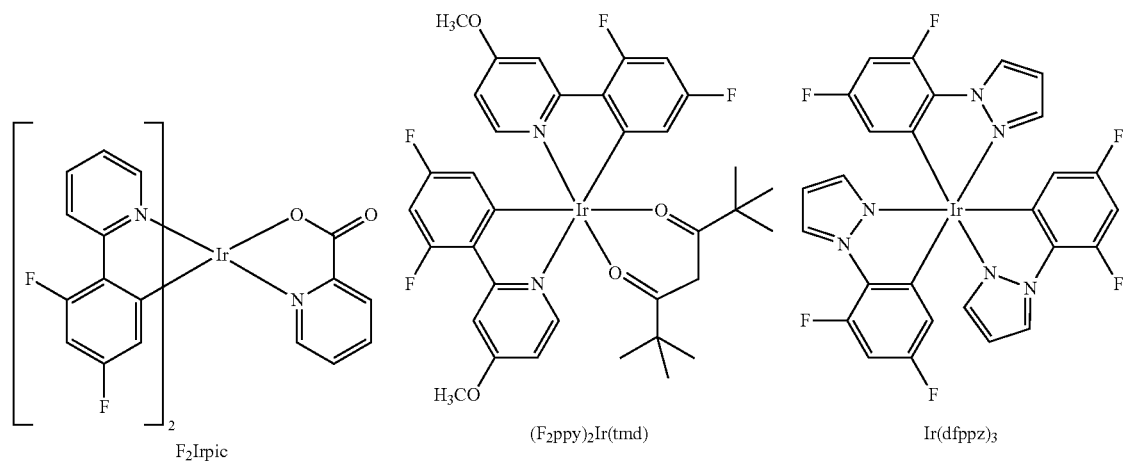

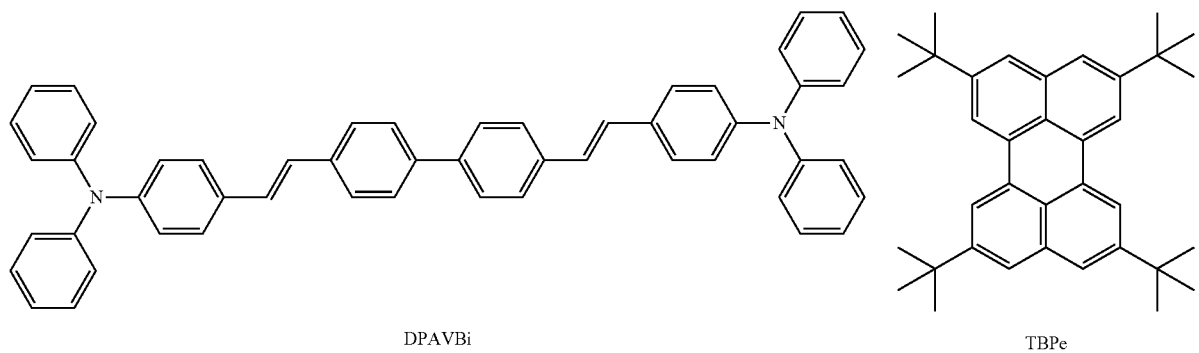

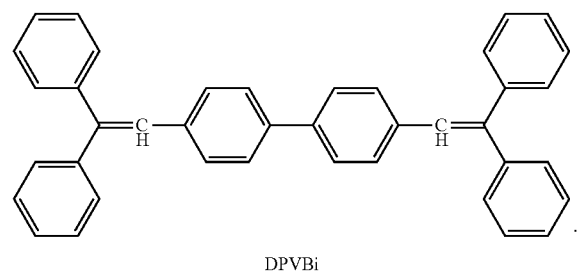

As a known red dopant, PtOEP, Ir(piq)₃, BtpIr, or the like may be used, but is not limited thereto.

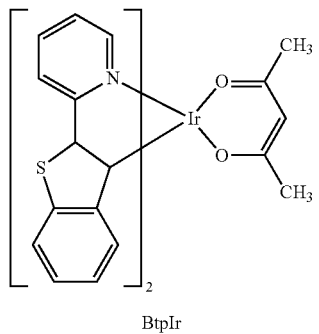

BtpIr

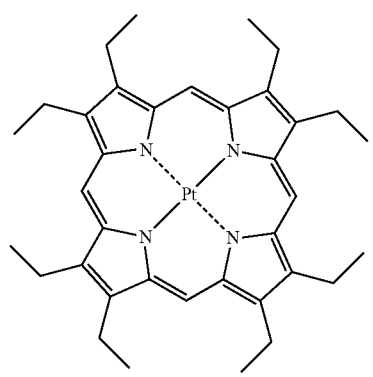

PtOEP

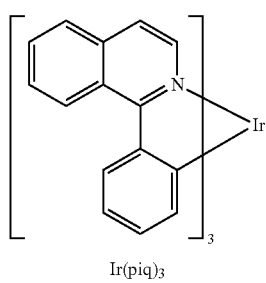

Ir(piq)₃

As a known green dopant, Ir(ppy)₃ (ppy=phenylpyridine), Ir(ppy)₂(acac), Ir(mpyp)₃, or the like may be used but is not limited thereto.

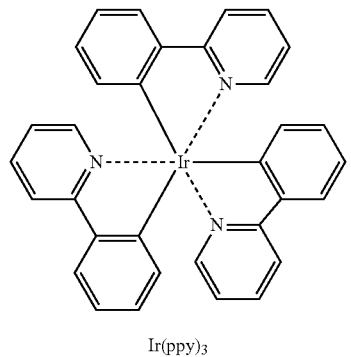

Ir(ppy)₃

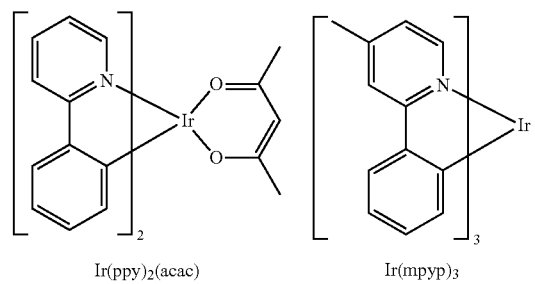

Ir(ppy)₂(acac)    Ir(mpyp)₃

Meanwhile, a dopant that may be included in the EML 133 may be a Pt-complex as described herein, but is not limited thereto:

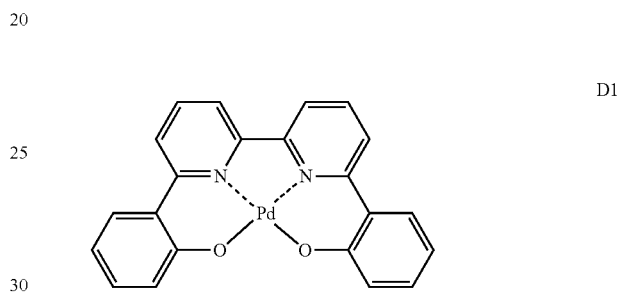

D1

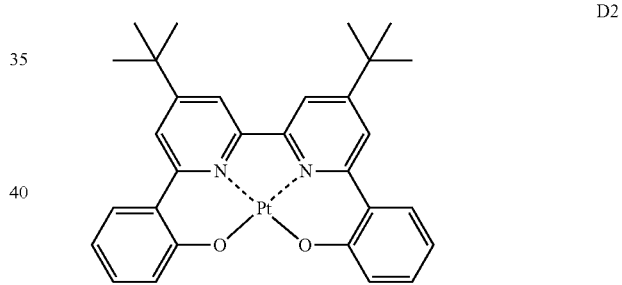

D2

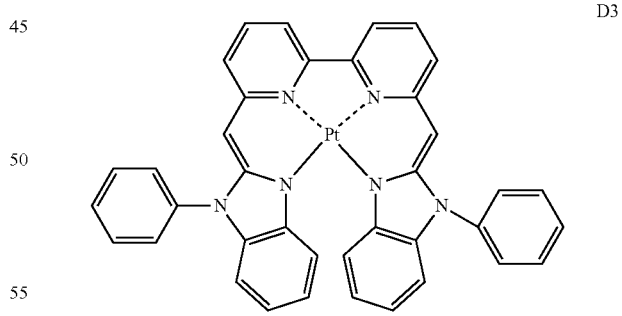

D3

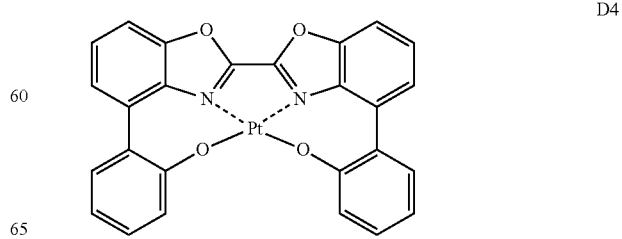

D4

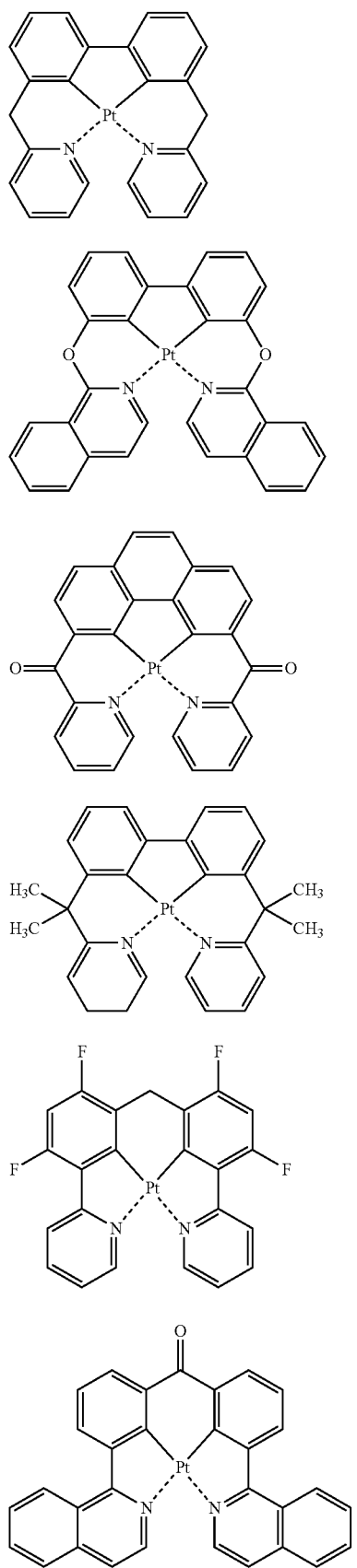
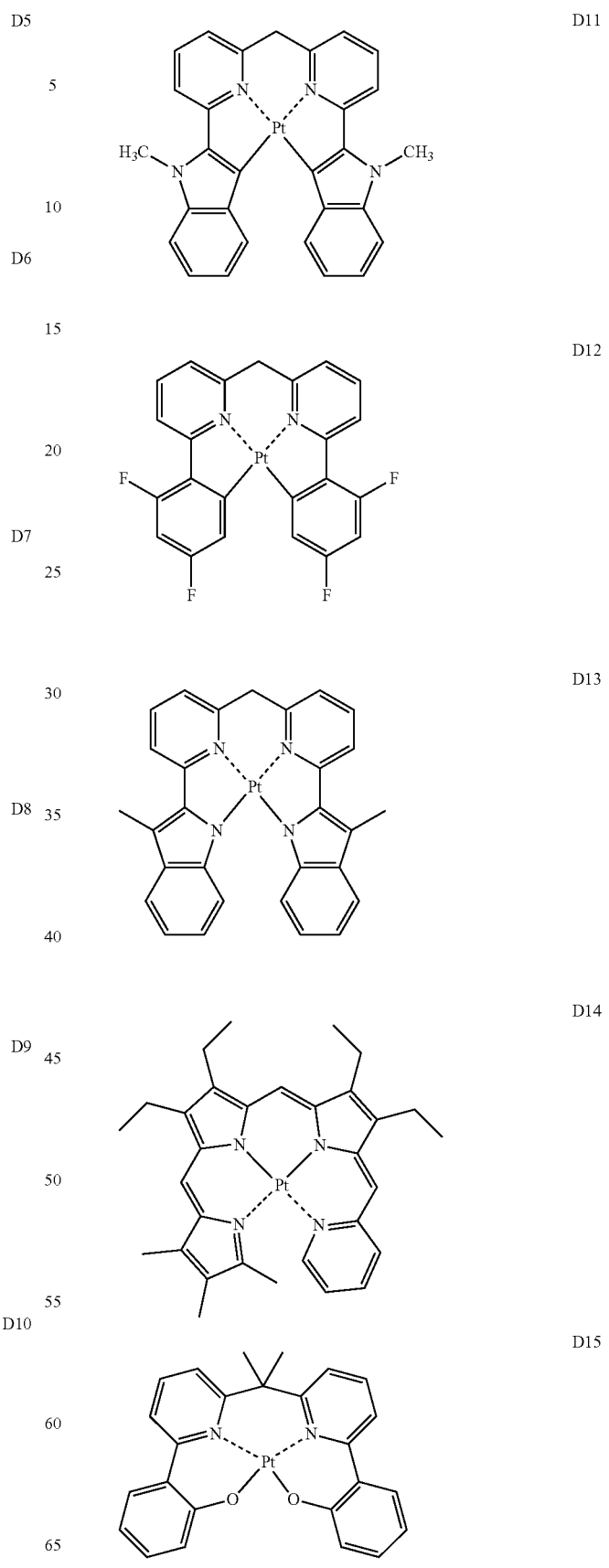

-continued
| | |
|---|---|
| 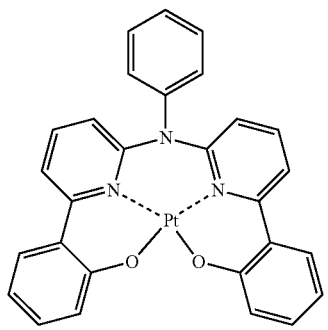 | D16 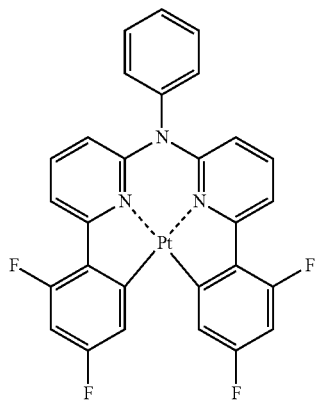 D21 |
| 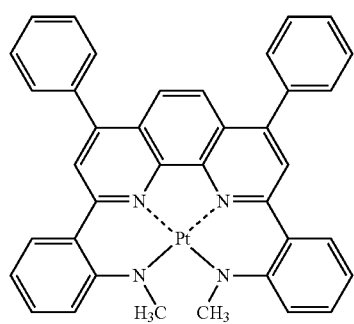 | D17 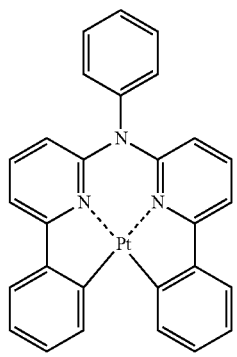 D22 |
| 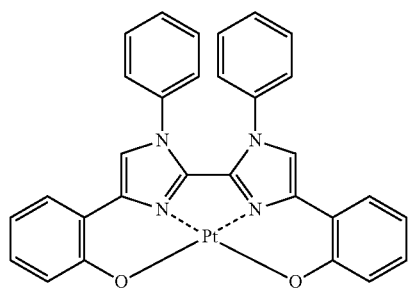 | D18 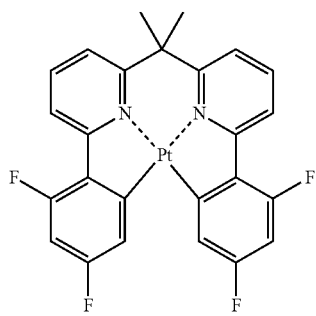 D23 |
| D19 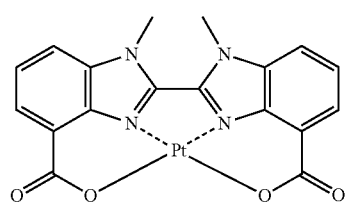 | 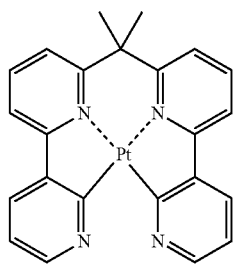 D24 |
| D20 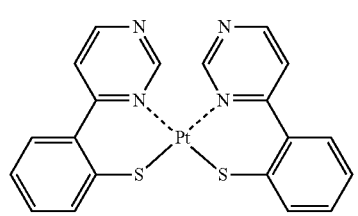 | 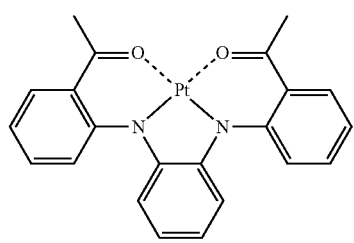 D25 |

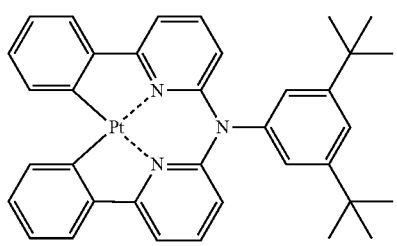
D26
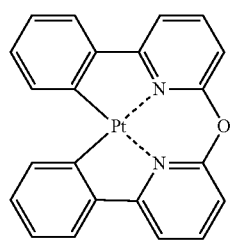
D27
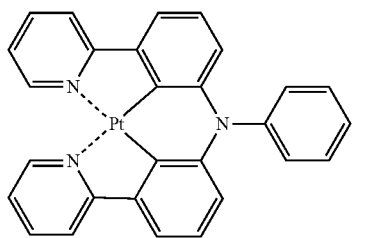
D28
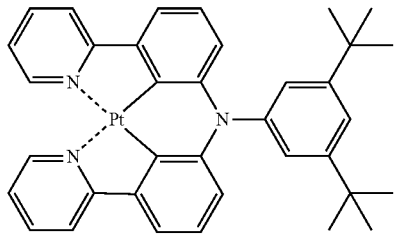
D29
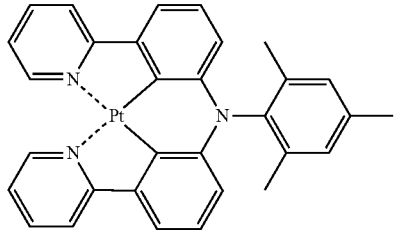
D30
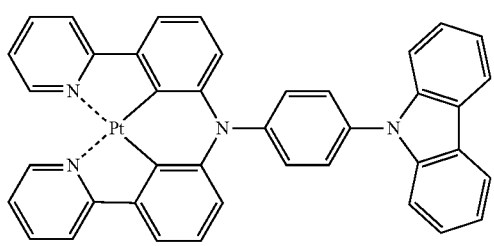
D31
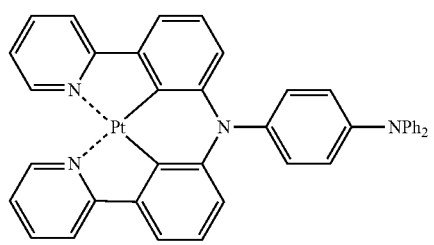
D32
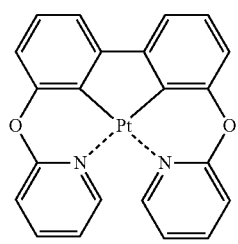
D33
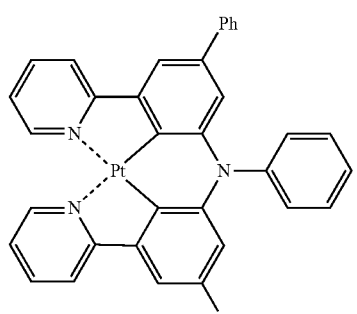
D34
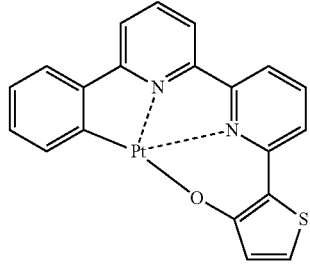
D35
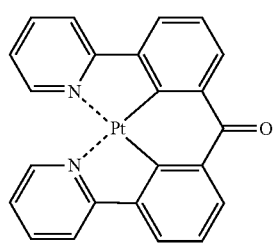
D36

D37
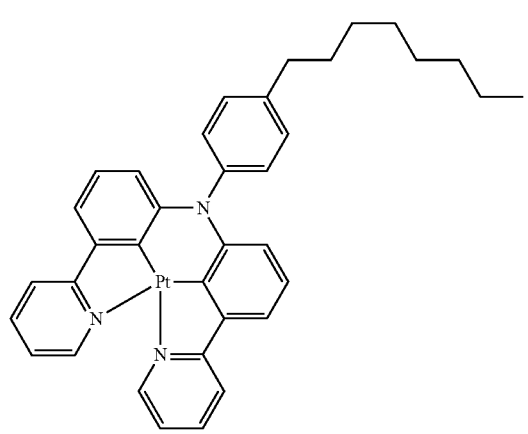
D38
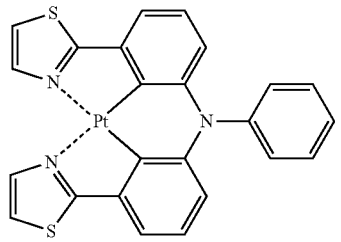
D39
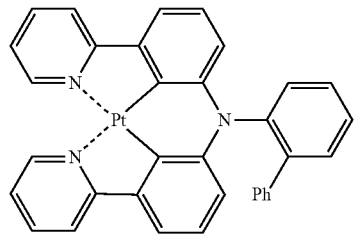
D40
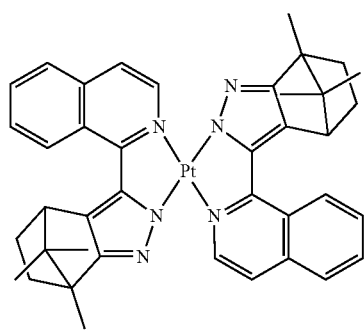
D41
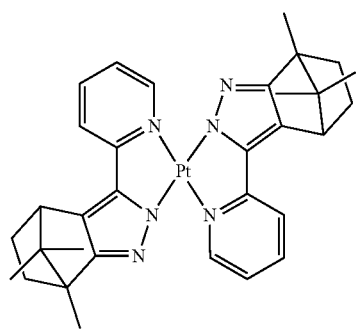
D42
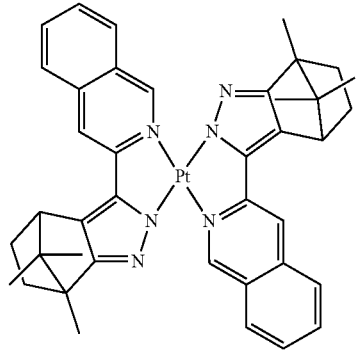
D43
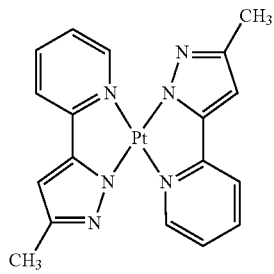
D44
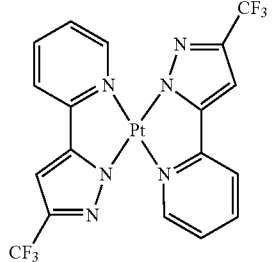
D45
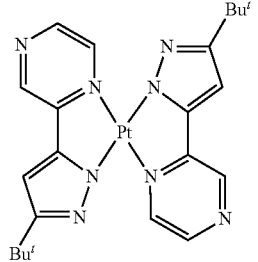
D46
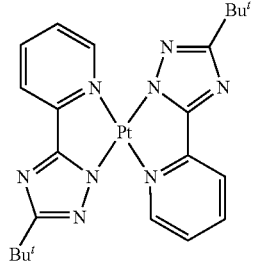

-continued

D47 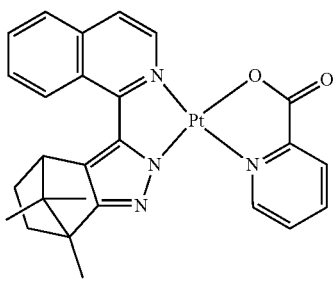

D48 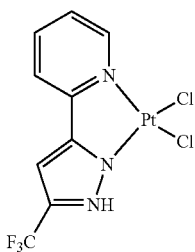

D49 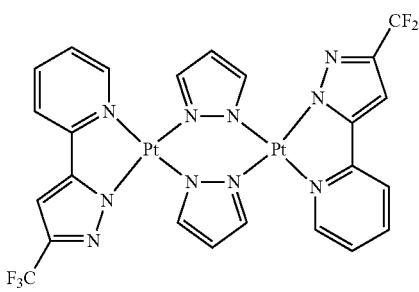

D50 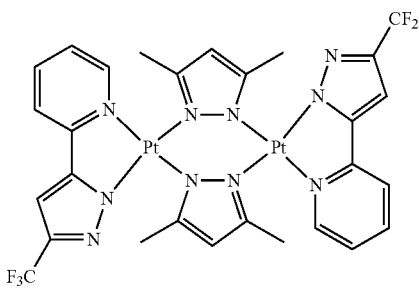

A dopant that may be included in the EML 133 may be an Os-complex as described herein, but is not limited thereto:

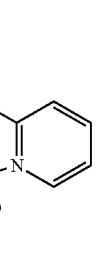

Os(fppz)$_2$(CO)$_2$

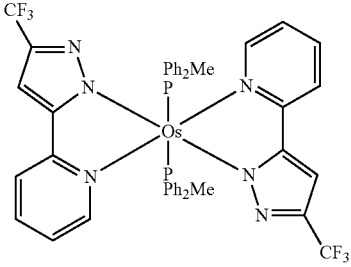

Os(fppz)$_2$(PPh$_2$Me)$_2$

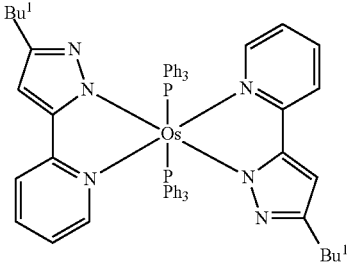

Os(bppz)$_2$(PPh$_3$)$_2$

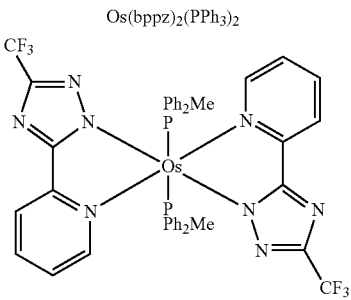

Os(fptz)$_2$(PPh$_2$Me)$_2$

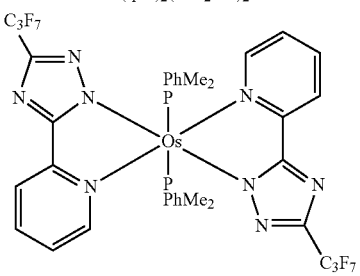

Os(hptz)$_2$(PPhMe$_2$)$_2$

When the EML 133 includes the host and the dopant, an amount of the dopant may generally be selected from the range of about 0.01 wt % to about 15 wt % based on 100 wt % of the EML 133, but the amount the dopant is not limited thereto.

A thickness of the EML 133 may be about 200 Å to about 700 Å. When the thickness of the EML 133 is within these ranges, the EML 133 may have good light-emitting ability without a substantial increase in driving voltage.

Then, the ETL 134 may be formed on the EML 133 by any of a variety of methods, for example, vacuum deposition, spin coating, or casting. When the ETL 134 is formed using vacuum deposition or spin coating, the deposition and coating conditions may be similar to those for the formation of the HIL 131, though the deposition and coating conditions may vary according to a material that is used to form the ETL 134.

A lowest unoccupied molecular orbital (LUMO) energy level of the first electron-transporting material (EL$_1$) may be 2.6 eV≤|EL$_1$|≤2.9 eV, and a highest occupied molecular orbital (HOMO) energy level of the first electron-transporting material (EH$_1$) may be 5.6 eV≤|EH$_1$|≤5.8 eV, but they are not limited thereto. A LUMO energy level of the second electron-transporting (EL$_2$) material may be 2.7 eV≤|EL$_2$|≤3.0 eV and an energy level (EH$_2$) of the HOMO of the second electron-transporting material may be 5.7 eV≤|EH$_2$|≤5.9 eV, but they are not limited thereto.

A method of measuring energy levels of a HOMO and a LUMO of a compound may be as follows, but the method is not limited thereto. HOMO and LUMO energy levels of a compound may be measured by using a cyclic voltammetry device, such as a ZIVE SP2 available from Wonatech. Each sample solution and an electrolyte solution used herein may be as follows, ferrocene may be used as a standard material, and (Bu)$_4$NPF$_6$ may be used as an electrolyte. For example, a sample solution of a compound to be measured is a 5×10$^{-3}$ M dichloromethane solution, a ferrocene sample solution, a (Bu)$_4$NPF$_6$ electrolyte solution, and a 0.1 M acetonitrile solution. An E$_{we}$-I relationship graph of the compound to be measured and the standard material may be drawn, wherein each tangent line is drawn from points at which current is drastically increased, and voltages of points at which the tangent lines contact an x-axis may be recorded. A HOMO energy level of the compound to be measured may be calculated by setting a HOMO energy level of ferrocene at -4.8 eV.

The ETL 134 may include the first electron-transporting material and the second electron-transporting material. A LUMO energy level of the first electron-transporting material (EL$_1$) and a LUMO energy level of the second electron-transporting material (EL$_2$) satisfy Equation 1. Accordingly, the first electron-transporting material and the second electron-transporting material are selected as different compounds.

0.1 eV≤|EL$_1$-EL$_2$|≤0.3 eV     <Equation 1>

As the EL$_1$ and the EL$_2$ satisfy Equation 1, the LUMO energy level of EL$_2$ forms an electron trap such that a number of electrons that move from the second electrode to the EML 133 may be controlled. By doing so, a lifespan of the organic light-emitting device may be improved.

According to an embodiment, the HOMO energy level of the first electron-transporting material (EH$_1$) and the LUMO energy level of the first electron-transporting material (EL$_1$) satisfy Equation 2. The HOMO energy level of the second electron-transporting material (EH$_2$) and the LUMO energy level of the second electron-transporting material (EL$_2$) may satisfy Equation 3, but are not limited thereto:

2.7 eV≤|EL$_1$-EH$_1$|≤3.2 eV     <Equation 2>

2.7 eV≤|EL$_2$-EH$_2$|≤3.2 eV

When each of EH$_1$, EL$_1$, EH$_2$, and EL$_2$ satisfies the relationship of Equation 2 or 3, a suitable electron-transporting ability may be obtained and a driving voltage need not increase substantially.

In another embodiment, a molecular weight of the first electron-transporting material (MW$_1$) and a molecular weight of the second electron-transporting material (MW$_2$) may satisfy Equation 4, but the molecular weights are not limited thereto.

|MW$_1$-MW$_2$|≤30     <Equation 4>

When MW$_1$ and MW$_2$ satisfy Equation 4, a difference in sublimation temperatures of the first electron-transporting material and the second electron-transporting material may be adjusted to a temperature of 30° C. or below. Accordingly, when a first electron-transporting material and a second electron-transporting material satisfying Equation 4 are selected, the materials are advantageous for preparing an ETL by using a vacuum deposition method.

According to another embodiment, both of the first electron-transporting material and the second electron-transporting material may be selected from non-metal-atom-containing organic compounds, but they are not limited thereto. To increase efficiency of an organic light-emitting device, an amount of electrons injected from the second electrode to the EML 133 may be increased. When an excessive amount of electrons is injected into the EML 133 to increase efficiency of an organic light-emitting device, an excessive amount of excitons is generated in the EML 133, thereby comparatively reducing a lifespan of the organic light-emitting device. When both of the first electron-transporting material and the second electron-transporting material are selected from non-metal-atom-containing organic compounds, the amount of electrons reaching the EML 133 may be suitably adjusted to improve the lifespan of the organic light-emitting device. Furthermore, when a metal-atom-containing compound such as LiQ or LiF is doped on the ETL 134, an oxidation may easily occur because the metal-atom-containing compound is highly reactive to oxygen. Accordingly, when both of the first electron-transporting material and the second electron-transporting material are selected from non-metal-atom-containing organic compounds, a lifespan of the organic light-emitting device may be improved.

According to another embodiment, the first electron-transporting material and the second electron-transporting material may be each independently selected from pyridine derivatives, pyrimidine derivatives, and triazine derivatives, but they are not limited thereto. As a number of nitrogen atoms included in the first electron-transporting material and the second electron-transporting material changes, LUMO energy level of the first electron-transporting material and the second electron-transporting material may be finely adjusted and thus, a compound satisfying Equation 1 may be suitably selected.

According to another embodiment, a weight ratio of the first electron-transporting material to the second electron-transporting material may be in a range of about 80:20 to about 50:50, but the weight ratio is not limited thereto. When the weight ratio of the first electron-transporting material to the second electron-transporting material is within the range above, the materials are suitable for forming an ETL 134 by using a vacuum deposition and an organic light-emitting device having improved lifespan may be provided.

According to another embodiment, the first electron-transporting material and the second electron-transporting material may be each independently selected from an amine-based compound represented by Formula 1 and an anthracene-based compound represented by Formula 2, but they are not limited thereto.

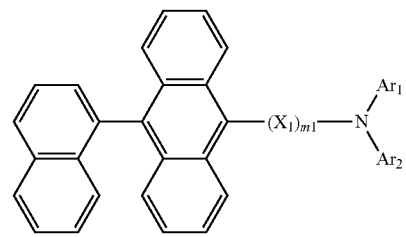

<Formula 1>

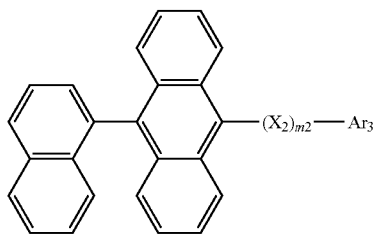

<Formula 2>

In Formulae 1 and 2, groups represented by $X_1$ and $X_2$ are each independently selected from a substituted or unsubstituted $C_6$-$C_{60}$ arylene group or a substituted or unsubstituted $C_2$-$C_{60}$ heteroarylene group. m1 and m2 are each independently selected from an integer of 0 to 5.

In Formula 1, groups represented by $Ar_1$ and $Ar_2$ are each independently selected from a substituted or unsubstituted $C_6$-$C_{60}$ aryl group and a substituted or unsubstituted $C_2$-$C_{60}$ heteroaryl group. At least one of the groups represented by $Ar_1$ and $Ar_2$ is selected from i) a pyridyl group, a pyrimidyl group, and a triazinyl group; ii) a pyridyl group, a pyrimidyl group, and a triazinyl group, each of which may be substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group, each of which may be substituted with at least one of a pyridyl group, a pyrimidyl group, and a triazinyl group; and iv) a pyridyl group, a pyrimidyl group, and a triazinyl group, each of which may be substituted with at least one of a $C_6$-$C_{60}$ aryl group and a $C_2$-$C_{60}$ heteroaryl group, which may each be substituted with at least one of a $C_6$-$C_{60}$ aryl group and a $C_2$-$C_{60}$ heteroaryl group.

A group represented by $Ar_3$ is selected from i) a pyridyl group, a pyrimidyl group, and a triazinyl group; ii) a pyridyl group, a pyrimidyl group, and a triazinyl group, each of which may be substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group, each of which may be substituted with at least one of a pyridyl group, a pyrimidyl group, and a triazinyl group; and iv) a pyridyl group, a pyrimidyl group, and a triazinyl group, each of which may be substituted with at least one of a $C_6$-$C_{60}$ aryl group and a $C_2$-$C_{60}$ heteroaryl group, each of which may be substituted with at least one of a $C_6$-$C_{60}$ aryl group and a $C_2$-$C_{60}$ heteroaryl group.

For example, in Formula 1, groups represented by $X_1$ and $X_2$ are each independently selected from a substituted or unsubstituted a phenylene group, a substituted or unsubstituted a pentalenylene group, a substituted or unsubstituted an indenylene group, a substituted or unsubstituted a naphthylene group, a substituted or unsubstituted an azulenylene group, a substituted or unsubstituted a heptalenylene group, a substituted or unsubstituted indacenylene group, a substituted or unsubstituted acenaphthylene group, a substituted or unsubstituted a fluorenylene group, a substituted or unsubstituted phenalenylene group, a substituted or unsubstituted a phenanthrenylene group, a substituted or unsubstituted an anthrylene group, a substituted or unsubstituted a fluoranthenylene group, a substituted or unsubstituted a triphenylenylene group, a substituted or unsubstituted a pyrenylene group, a substituted or unsubstituted chrysenylene group, a substituted or unsubstituted a naphthacenylene group, a substituted or unsubstituted a picenylene group, a substituted or unsubstituted a perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, a substituted or unsubstituted oxadiazolylene group, a substituted or unsubstituted pyridazinylene group, a substituted or unsubstituted triazolylene group, and a substituted or unsubstituted tetrazolylene group, but they are not limited thereto.

As another example, in Formula 1, groups represented by $X_1$ and $X_2$ are each independently selected from a substituted or unsubstituted a phenylene group, a substituted or unsubstituted a naphthylene group, a substituted or unsubstituted an anthrylene group, a substituted or unsubstituted pyridinylene group, a substituted or unsubstituted pyrimidinylene group, and a substituted or unsubstituted triazolylene group, but they are not limited thereto.

For example, in Formula 1, m1 and m2 are each independently selected from an integer of 1 to 2, but they are not limited thereto. For example, moieties represented by $(X_1)_{m1}$ and $(X_2)_{m2}$ may be any one selected from Formulae 3-1 to 3-4, but they are not limited thereto:

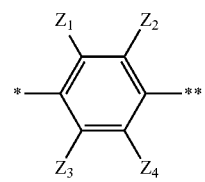

3-1

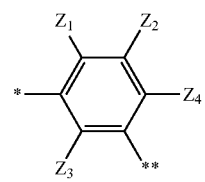

3-2

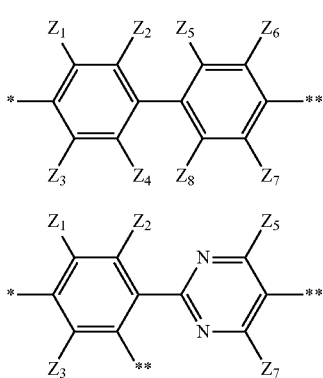

In Formulae 3-1 to 3-4, groups represented by $Z_1$ to $Z_8$ may be each independently selected from a hydrogen atom; a deuterium atom; —F; —Cl; —Br; —I; —CN; a hydroxyl group; —$NO_2$; a $C_1$-$C_{20}$ alkyl group; a $C_1$-$C_{20}$ alkoxy group; a $C_1$-$C_{20}$ alkyl group and a $C_1$-$C_{20}$ alkoxy group, each of which may be substituted with at least one of a deuterium atom, —F, —Cl, —Br, —I, —CN, a hydroxyl group, and —$NO_2$; a $C_6$-$C_{20}$ aryl group; a $C_2$-$C_{20}$ heteroaryl group; and a $C_6$-$C_{20}$ aryl group and a $C_2$-$C_{20}$ heteroaryl group, each of which may be substituted with at least one of a deuterium atom, —F, —Cl, —Br, —I, —CN, a hydroxyl group, —$NO_2$, a $C_1$-$C_{20}$ alkyl group, a $C_1$-$C_{20}$ alkoxy group, a $C_6$-$C_{20}$ aryl group, and a $C_2$-$C_{20}$ heteroaryl group; * is a bonding site to an anthracene of Formulae 1 and 2; ** is a bonding site to a nitrogen atom of Formula 1 or a bonding site to the group represented by $Ar_3$ of Formula 2.

For example, in Formula 1, groups represented by $Ar_1$ and $Ar_2$ are each independently selected from i) a $C_6$-$C_{60}$ aryl group and a $C_2$-$C_{60}$ heteroaryl group; ii) a $C_6$-$C_{60}$ aryl group and a $C_2$-$C_{60}$ heteroaryl group, each of which may be substituted with at least one of a deuterium atom, a halogen atom, a cyano group, a nitro group, a $C_1$-$C_{20}$ alkyl group, a $C_6$-$C_{60}$ aryl group, and a $C_2$-$C_{60}$ heteroaryl group; and iii) a $C_6$-$C_{60}$ aryl group and a $C_2$-$C_{60}$ heteroaryl group, each of which may be substituted with at least one of a $C_6$-$C_{60}$ aryl group and a $C_2$-$C_{60}$ heteroaryl group, each of which may be substituted with at least one of a deuterium atom, a halogen atom, a cyano group, a nitro group, a $C_1$-$C_{20}$ alkyl group, a $C_6$-$C_{60}$ aryl group, and a $C_2$-$C_{60}$ heteroaryl group.

At least one of the groups represented by $Ar_1$ and $Ar_2$ may be selected from i) a pyridyl group, a pyrimidyl group, and a triazinyl group; ii) a pyridyl group, a pyrimidyl group, and a triazinyl group, each of which may be substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group, each of which may be substituted with at least one of a pyridyl group, a pyrimidyl group, and a triazinyl group; and iv) a pyridyl group, a pyrimidyl group, and a triazinyl group, each of which may be substituted with at least one of a $C_6$-$C_{60}$ aryl group and a $C_2$-$C_{60}$ heteroaryl group, each of which may be substituted with at least one of a $C_6$-$C_{60}$ aryl group and a $C_2$-$C_{60}$ heteroaryl group, but they are not limited thereto.

As another example, in Formula 1, the groups represented by $Ar_1$ and $Ar_2$ may be each independently selected from i) a $C_6$-$C_{60}$ aryl group and a $C_2$-$C_{60}$ heteroaryl group; ii) a $C_6$-$C_{60}$ aryl group and a $C_2$-$C_{60}$ heteroaryl group, each of which may be substituted with at least one of a deuterium atom, a halogen atom, a cyano group, a nitro group, a $C_1$-$C_{20}$ alkyl group, a $C_6$-$C_{60}$ aryl group, and a $C_2$-$C_{60}$ heteroaryl group.

At least one of the groups represented by $Ar_1$ and $Ar_2$ may be selected from i) a pyridyl group, a pyrimidyl group, and a triazinyl group; ii) a pyridyl group, a pyrimidyl group, and a triazinyl group, each of which may be substituted with at least one of a phenyl group, a naphthyl group, a pyridyl group, a pyrimidyl group, and a triazinyl group; iii) a phenyl group, a naphthyl group, a pyridyl group, a pyrimidyl group, and a triazinyl group, each of which may be substituted with at least one of a pyridyl group, a pyrimidyl group, and a triazinyl group; and iv) a pyridyl group, a pyrimidyl group, and a triazinyl group, each of which may be substituted with at least one of a phenyl group, a naphthyl group, a pyridyl group, a pyrimidyl group, and a triazinyl group, each of which may be substituted with at least one of a phenyl group, a naphthyl group, a pyridyl group, a pyrimidyl group, and a triazinyl group, but they are not limited thereto.

As another example, in Formula 1, the groups represented by $Ar_1$ and $Ar_2$ may be each independently selected from i) a $C_6$-$C_{60}$ aryl group and a $C_2$-$C_{60}$ heteroaryl group; ii) a $C_6$-$C_{60}$ aryl group and a $C_2$-$C_{60}$ heteroaryl group, each of which may be substituted with at least one of a deuterium atom, a halogen atom, a cyano group, a nitro group, a $C_1$-$C_{20}$ alkyl group, a $C_6$-$C_{60}$ aryl group, and a $C_2$-$C_{60}$ heteroaryl group; and iii) a $C_6$-$C_{60}$ aryl group and a $C_2$-$C_{60}$ heteroaryl group, each of which may be substituted with at least one of a $C_6$-$C_{60}$ aryl group and a $C_2$-$C_{60}$ heteroaryl group, each of which may be substituted with at least one of a deuterium atom, a halogen atom, a cyano group, a nitro group, a $C_1$-$C_{20}$ alkyl group, a $C_6$-$C_{60}$ aryl group, and a $C_2$-$C_{60}$ heteroaryl group. At least one of the groups represented by $Ar_1$ and $Ar_2$ may be represented by any one of Formulae 4-1 to 4-6, but are not limited thereto.

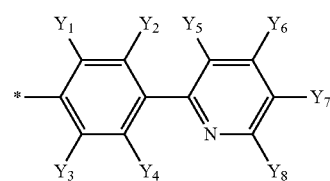

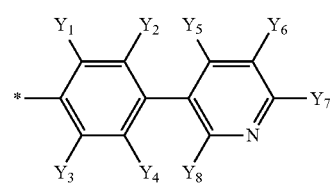

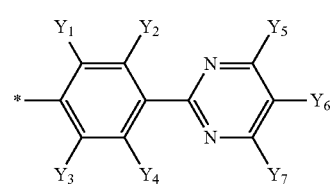

4-4

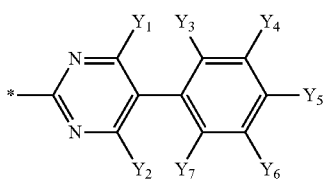

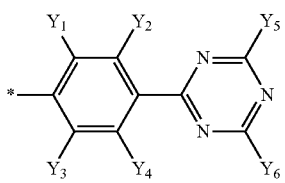
4-5

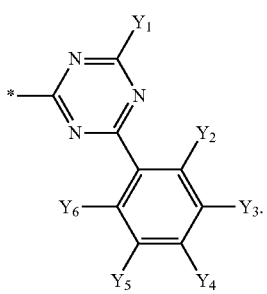
4-6

In Formulae 4-1 to 4-6, groups represented by $Y_1$ to $Y_8$ may be each independently selected from a hydrogen atom, a phenyl group, a naphthyl group, a pyridyl group, a pyrimidyl group, and a triazinyl group; and * is a bonding site to a nitrogen atom of Formula 1.

As another example, in Formula 1, the groups represented by $Ar_1$ and $Ar_2$ may be represented by any one of Formulae 4-1 to 4-9; and at least one of the groups represented by $Ar_1$ and $Ar_2$ may be represented by any one of Formulae 4-1 to 4-6, but they are not limited thereto.

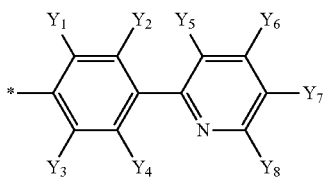
4-1

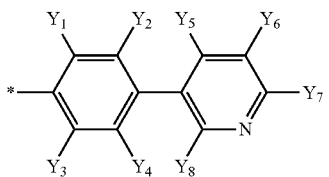
4-2

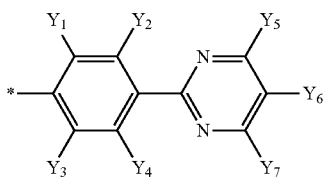
4-3

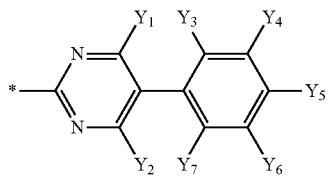
4-4

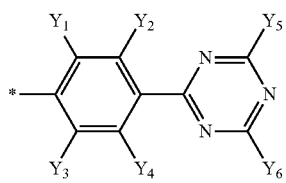
4-5

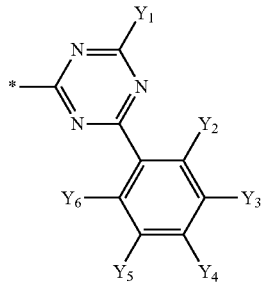
4-6

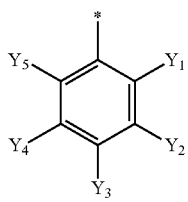
4-7

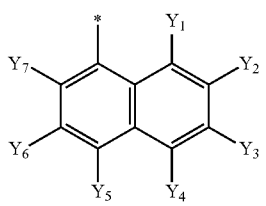
4-8

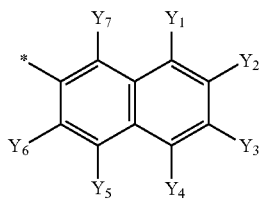
4-9

In Formulae 4-1 to 4-9, the groups represented by $Y_1$ to $Y_8$ may be each independently selected from a hydrogen atom, a phenyl group, a naphthyl group, a pyridyl group, a pyrimidyl group, and a triazinyl group; and * is a bonding site to a nitrogen atom of Formula 1.

For example, in Formula 2, a group represented by $Ar_3$ may be selected from i) a pyridyl group, a pyrimidyl group, and a triazinyl group; ii) a pyridyl group, a pyrimidyl group, and a triazinyl group, each of which may be substituted with at least one of a phenyl group, a naphthyl group, a pyridyl group, a pyrimidyl group, and a triazinyl group; iii) a phenyl group, a naphthyl group, a pyridyl group, a pyrimidyl group, and a triazinyl group, each of which may be substituted with at least one of a pyridyl group, a pyrimidyl group, and a triazinyl group; and iv) a pyridyl group, a pyrimidyl group, and a triazinyl group, each of which may be substituted with at least one of a phenyl group, a naphthyl group, a pyridyl group, a pyrimidyl group, and a triazinyl group, each of which may be substituted with at least one of a phenyl group, a naphthyl group, a pyridyl group, a pyrimidyl group, and a triazinyl group, but is not limited thereto.

As another example, in Formula 2, the group represented by $Ar_3$ may be represented by any one of Formulae 4-1 to 4-6, but is not limited thereto:

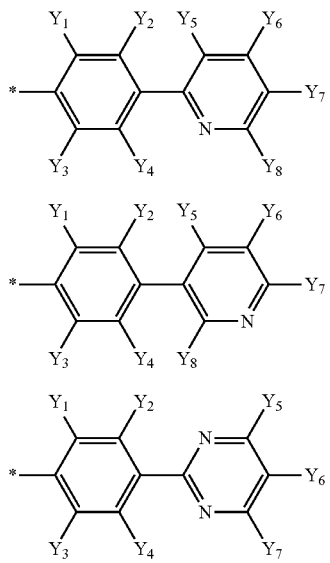

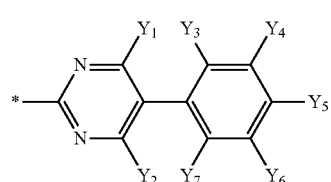

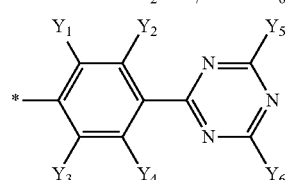

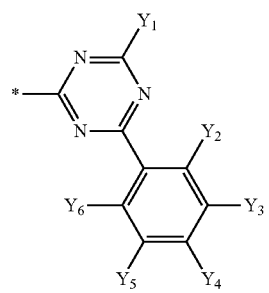

In Formulae 4-1 to 4-6, the groups represented by $Y_1$ to $Y_8$ may be each independently selected from a hydrogen atom, a phenyl group, a naphthyl group, a pyridyl group, a pyrimidyl group, and a triazinyl group; and * is a bonding site to a nitrogen atom of Formula 1.

In an embodiment, the first electron-transporting material and the second electron-transporting material may be each independently selected from Compounds 1 to 15:

<Compound 1>

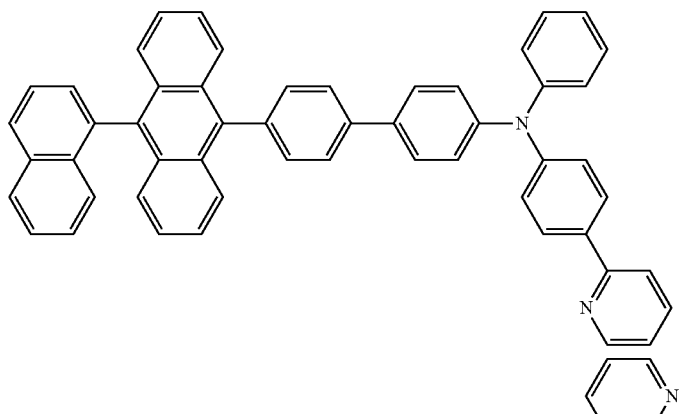

<Compound 2>

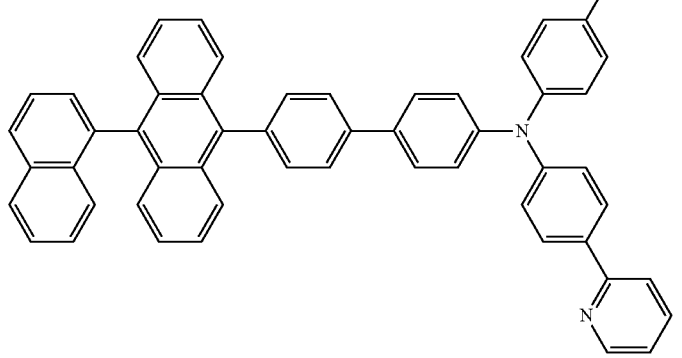

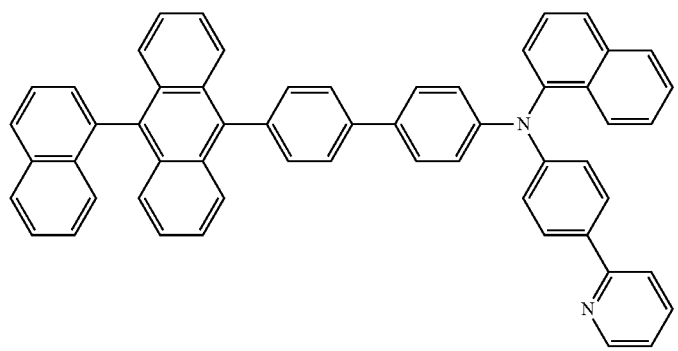
<Compound 3>
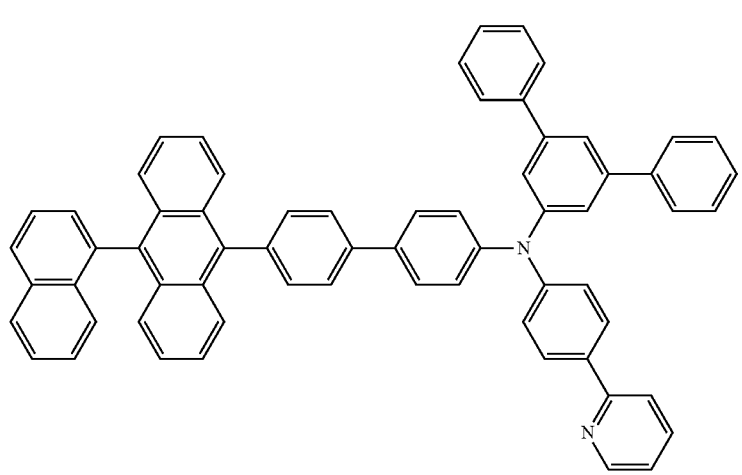
<Compound 4>
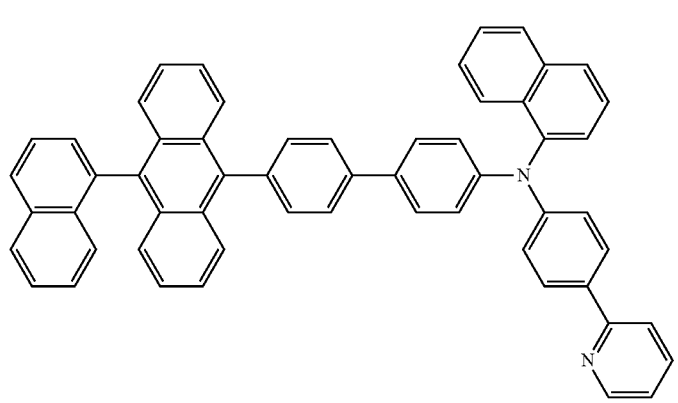
<Compound 5>
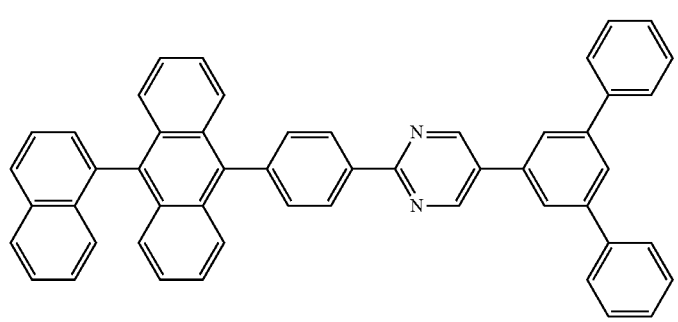
<Compound 6>

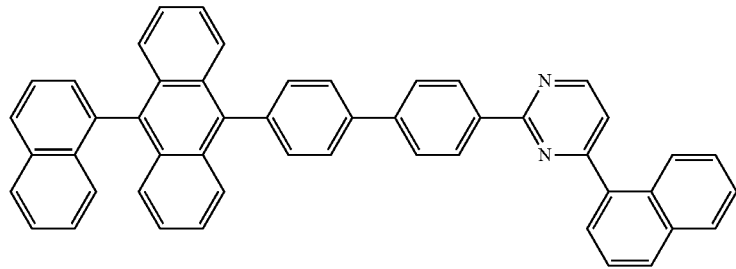
<Compound 7>
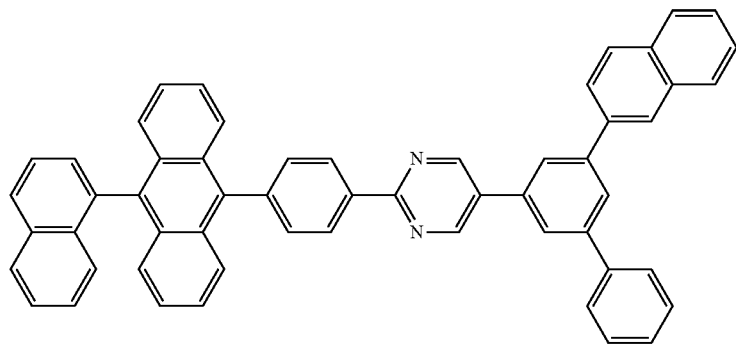
<Compound 8>
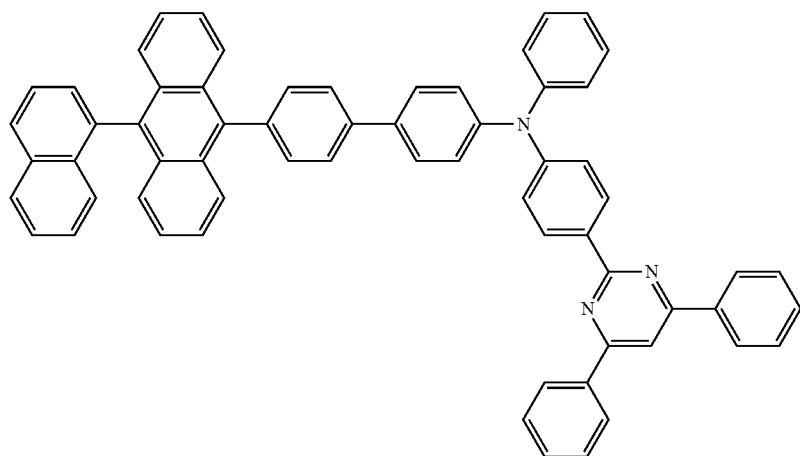
<Compound 9>
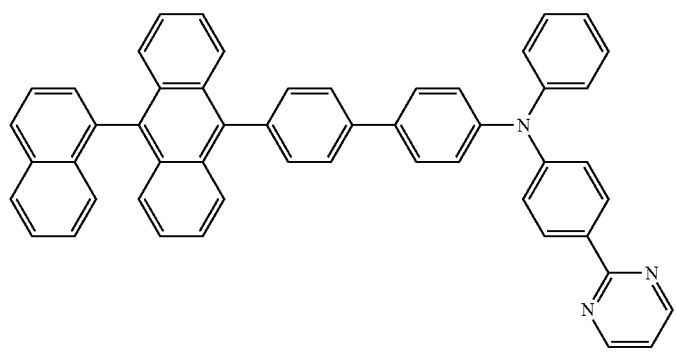
<Compound 10>

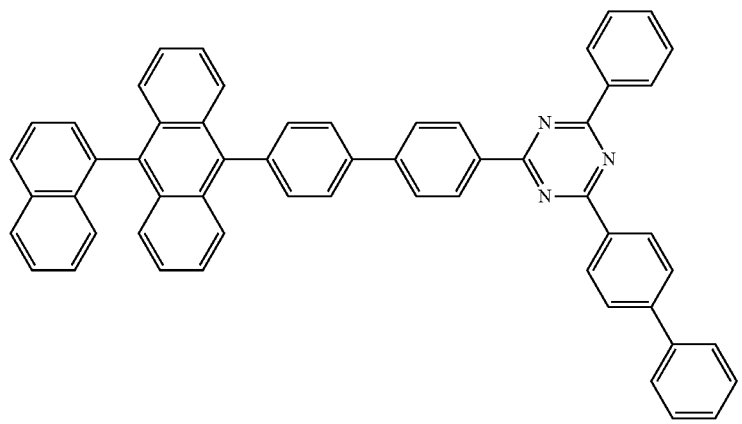
<Compound 11>
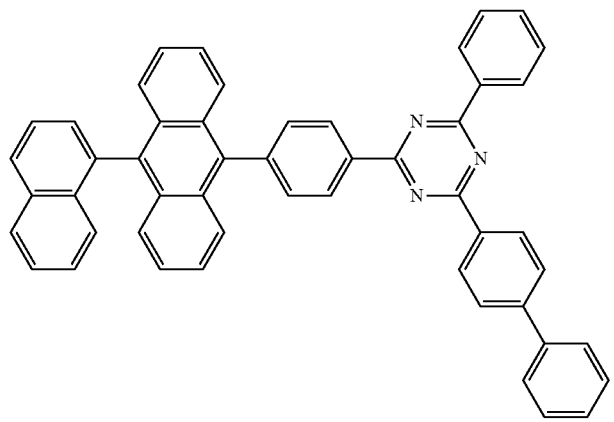
<Compound 12>
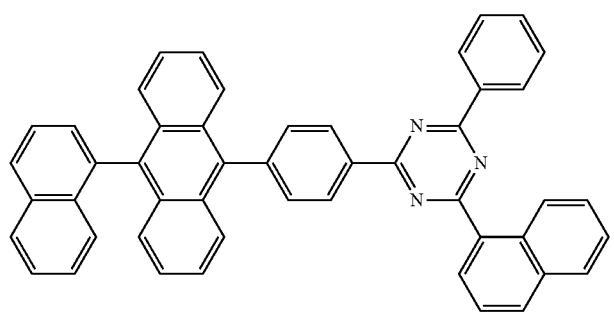
<Compound 13>
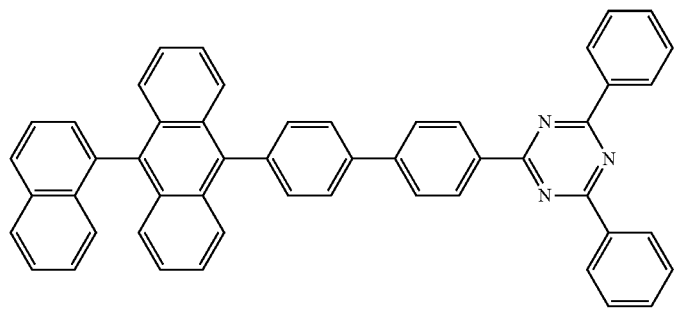
<Compound 14>

-continued

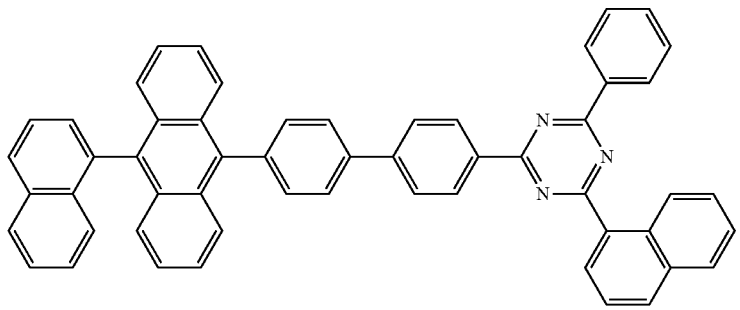

<Compound 15>

In another embodiment, i) the first electron-transporting material is at least one amine-based compound represented by Formula 1 and the second electron-transporting material is at least one amine-based compound represented by Formula 1; ii) the first electron-transporting material is at least one amine-based compound represented by Formula 1 and the second electron-transporting material is one anthracene-based compound represented by Formula 2; or iii) the first electron-transporting material is at least one anthracene-based compound represented by Formula 2 and the second electron-transporting material is an anthracene-based compound represented by Formula 2. The first electron-transporting material and the second electron-transporting material may be different.

In another embodiment, i) the first electron-transporting material and the second electron-transporting material are each independently at least one selected from Compounds 1 to 5; ii) the first electron-transporting material is at least one selected from Compounds 1 to 5 and the second electron-transporting material is at least one selected from Compounds 6 to 10; the first electron-transporting material is at least one selected from Compounds 1 to 5 and the second electron-transporting material is at least one selected from Compounds 11 to 15; iv) the first electron-transporting material and the second electron-transporting material are each independently at least one selected from Compounds 6 to 10; v) the first electron-transporting material is at least one selected from Compounds 6 to 10 and the second electron-transporting material is at least one selected from Compounds 11 to 15; yl) the first electron-transporting material and the second electron-transporting material are each independently at least one selected from Compounds 11 to 15; and the first electron-transporting material and the second electron-transporting material may be different.

The ETL 134 may include just the first electron-transporting material and the second electron-transporting material, but it is not limited thereto. The ETL 134 may further include a known electron-transporting material. Non-limiting examples of known electron-transporting materials include quinoline derivatives such as tris(8-quinolinolate)aluminum (Alq$_3$), TAZ, BAlq, beryllium bis(benzoquinolin-10-olate) (Bebq$_2$), 9,10-di(naphthalene-2-yl)anthracene (ADN), Compound 201, and Compound 202.

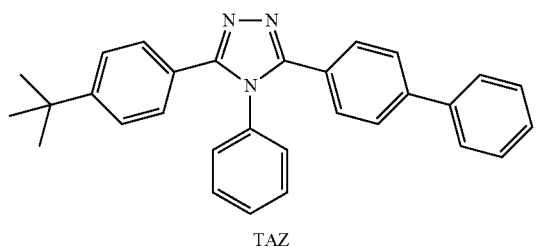

TAZ

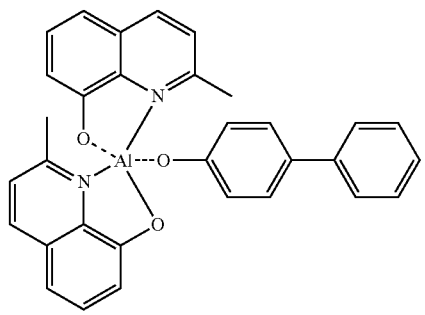

BAlq

<Compound 201>

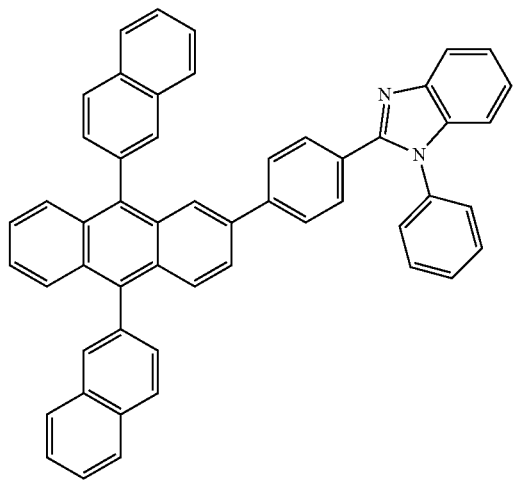

<Compound 202>

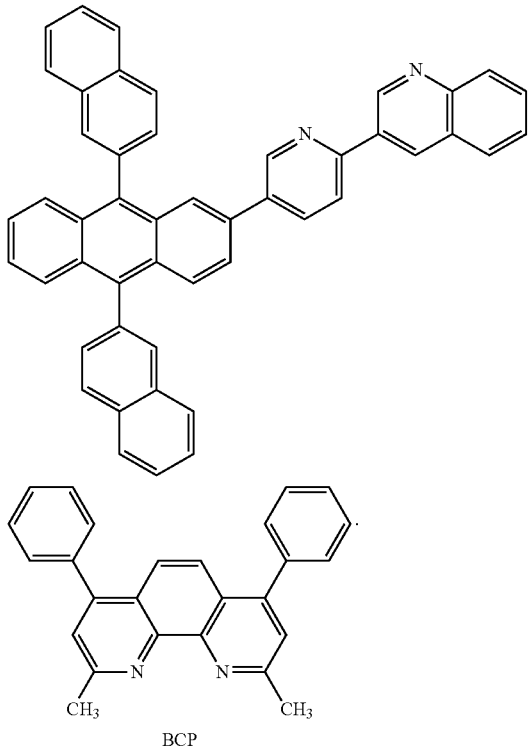

BCP

In some embodiments, the ETL 134 may further include a known metal-containing material.

The metal-containing material may include an Li complex. Non-limiting examples of the Li complex are lithium quinolate (LiQ) and Compound 203.

<Compound 203>

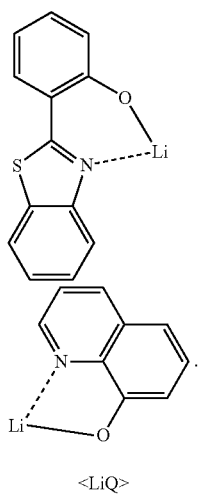

<LiQ>

A thickness of the ETL 134 may be from about 100 Å to about 1,000 Å, and in some embodiments, may be from about 150 Å to about 500 Å. When the thickness of the ETL 134 is within these ranges, the ETL 134 may have satisfactory electron-transporting ability without a substantial increase in driving voltage. The EIL 135, which has a function of facilitating an injection of electrons from the cathode, may be layered on the ETL 134. Any suitable electron-injecting material may be used to form the EIL 135.

As the EIL-forming materials, known EIL-forming materials such as LiF, NaCl, CsF, $Li_2O$, and BaO may be used. The deposition and coating conditions for forming the EIL 135 may be similar to those for the formation of the HIL 131, though the deposition and coating conditions may vary according to the compound that is used to form the EIL 135. A thickness of the EIL 135 may be from about 1 Å to about 100 Å, and in some embodiments, may be from about 3 Å to about 90 Å. When the thickness of the EIL 135 is within these ranges, the EIL 135 may have satisfactory electron-injecting ability without a substantial increase in driving voltage.

The second electrode 140 is disposed on the organic layer 130. The second electrode 140 may be a cathode that is an electron-injecting electrode, wherein a material for forming the second electrode 140 may be a metal, an alloy, or an electro-conductive compound, which have a low work function, or a mixture thereof. In this regard, the second electrode 140 may be formed of lithium (Li), magnesium (Mg), aluminum (Al), aluminum lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting device, the transmission electrode may be formed of indium tin oxide (ITO) or indium zinc oxide (IZO).

The organic light-emitting device 100 has been described with reference to FIG. 1, but the organic light-emitting device 100 is not limited thereto.

When a phosphorescent dopant is used in the EML 133, a hole-blocking layer (HBL) may be formed between the HTL 132 and EML 133 or the H-functional layer and EML 133 by using vacuum deposition, spin coating, casting, LB deposition, or the like, in order to prevent diffusion of triplet excitons or holes into the ETL 134. When the HBL is formed using vacuum deposition or spin coating, the conditions for deposition and coating may be similar to those for the formation of the HIL 131, although the conditions for deposition and coating may vary according to the material that is used to form the HBL. A known hole-blocking material may be used, and non-limiting examples of the known hole-blocking material include oxadiazole derivatives, triazole derivatives, and phenanthroline derivatives. In some embodiments, BCP shown may be used as a hole-blocking material.

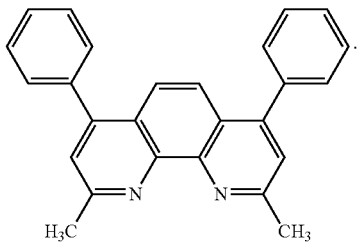

BCP

A thickness of the HBL may be about 20 Å to about 1000 Å, and in some embodiments, may be about 30 Å to about 300 Å. When the thickness of the HBL is within these ranges, the HBL may have improved hole blocking ability without a substantial increase in driving voltage.

An organic light-emitting device according to an embodiment of the present disclosure is described with reference to Synthesis Examples and Examples, but the present disclosure is not limited to the Synthesis Examples and Examples. As used herein, specific examples of an unsubstituted $C_1$-$C_{60}$ alkyl group (or the $C_1$-$C_{60}$ alkyl group) include a linear or a branched $C_1$-$C_{60}$ alkyl group such as methyl, ethyl, propyl, iso-butyl, sec-butyl, pentyl, iso-amyl, and hexyl, and a substituted $C_1$-$C_{60}$ alkyl group is the unsubstituted $C_1$-$C_{60}$ alkyl group, wherein one or more of a hydrogen atoms of the unsubstituted $C_1$-$C_{60}$ alkyl group may be substituted with a deuterium atom, a halogen atom, a hydroxyl group, a cyano group, a nitro group, an amino group, an amidino group, hydrazine, hydrazone, a carboxyl acid group or a salt thereof, a sulfonic acid group or a salt thereof, phosphoric acid or a salt thereof, a $C_1$-$C_{60}$ alkyl group, a $C_1$-$C_{60}$ fluoroalkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$). $Q_{11}$ to $Q_{15}$ may each be independently selected from a hydrogen atom, a $C_1$-$C_{60}$ alkyl group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

An unsubstituted $C_1$-$C_{60}$ alkoxy group (or the $C_1$-$C_{60}$ alkoxy group) has a formula of —OA (wherein, A is the unsubstituted $C_1$-$C_{60}$ alkyl group as described herein), and specific examples of the unsubstituted $C_1$-$C_{60}$ alkoxy group include methoxy, ethoxy, and iso-propoxy, and at least one a hydrogen atom of the alkoxy groups may be substituted with the substituents described above in conjunction with the substituted $C_1$-$C_{60}$ alkyl group.

An unsubstituted $C_6$-$C_{60}$ aryl group is a monovalent group having a carbocyclic aromatic system having 6 to 60 carbon atoms including at least one aromatic ring, and an unsubstituted $C_6$-$C_{60}$ arylene group is a divalent group having a carbocyclic aromatic system having 6 to 60 carbon atoms including at least one aromatic ring. When the unsubstituted $C_6$-$C_{60}$ aryl group and the unsubstituted $C_6$-$C_{60}$ arylene group include at least two rings, two or more rings may be fused to each other. At least one of a hydrogen atom of the unsubstituted $C_6$-$C_{60}$ aryl group and the unsubstituted $C_6$-$C_{60}$ arylene group may be substituted with those substituents described above in conjunction with the substituted $C_1$-$C_{60}$ alkyl group.

Examples of a substituted or unsubstituted $C_6$-$C_{60}$ aryl group include a phenyl group, a $C_1$-$C_{10}$ alkyl phenyl group (for example, an ethyl phenyl group), a $C_1$-$C_{10}$ alkyl biphenyl group (for example, an ethyl biphenyl group), a halophenyl group (for example, an o-, m-, and p-fluorophenyl group and a dichlorophenyl group), a dicyanophenyl group, a trifluoromethoxy phenyl group, an o-, m-, and p-tolyl group, an o-, m-, and p-cumenyl group, a mesityl group, a phenoxy phenyl group, an (α,α-dimethyl benzene)phenyl group, an (N,N'-dimethyl)aminophenyl group, an (N,N'-diphenyl)aminophenyl group, a pentalenyl group, an indenyl group, a naphthyl group, a halonaphthyl group (for example, a fluoronaphthyl group), a $C_1$-$C_{10}$ alkyl naphthyl group (for example, a methyl naphthyl group), a $C_1$-$C_{10}$ alkoxy naphthyl group (for example, a methoxy naphthyl group), an anthracenyl group, an azulenyl group, a heptalenyl group, an acenaphthylenyl group, a phenalenyl group, a fluorenyl group, an anthraquinolyl group, a methyl anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group, and a spiro-fluorenyl group, and examples of the substituted $C_6$-$C_{60}$ aryl group may be inferred based on the examples of the unsubstituted $C_6$-$C_{60}$ aryl group and the substituents described above in conjunction with the substituted $C_1$-$C_{60}$ alkyl group. Examples of the substituted or unsubstituted $C_6$-$C_{60}$ arylene group may be inferred based on the examples of the substituted or unsubstituted $C_6$-$C_{60}$ aryl group.

An unsubstituted $C_2$-$C_{60}$ heteroaryl group is a monovalent group having a system formed of at least one aromatic ring that includes at least one heteroatom selected from N, O, P, and S as ring-forming atoms and carbon atoms as other ring atoms, and an unsubstituted $C_2$-$C_{60}$ heteroarylene group is a divalent group having a system formed of at least one aromatic ring that includes at least one heteroatom selected from N, O, P, and S as ring-forming atoms and carbon atoms as other ring atoms. When the unsubstituted $C_2$-$C_{60}$ heteroaryl group and the unsubstituted $C_2$-$C_{60}$ heteroarylene group include two or more rings, the two or more rings may be fused to each other. At least one hydrogen atom of the unsubstituted $C_2$-$C_{60}$ heteroaryl group and the unsubstituted $C_2$-$C_{60}$ heteroarylene group may be substituted with those substituents described above in conjunction with the substituted $C_1$-$C_{60}$ alkyl group.

Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, an imidazopyrimidinyl group, a furanyl group, a thiophenyl group, a benzofuranyl group, a benzothiophenyl group, a dibenzofuranyl group, and a dibenzothiophenyl group. Examples of the unsubstituted $C_2$-$C_{60}$ heteroarylene group may be inferred based on the examples of a substituted or unsubstituted $C_2$-$C_{60}$ arylene group.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Example 1

Synthesis of Compound 10

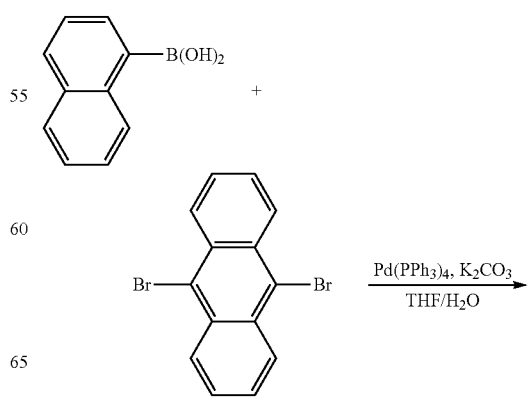

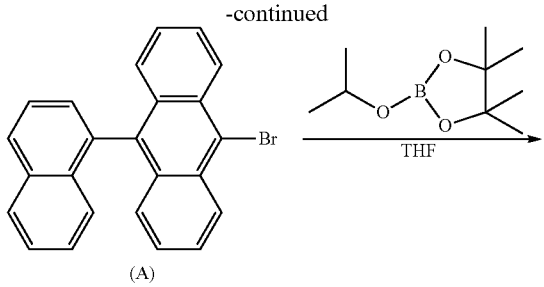

Synthesis of Intermediate I-1

9.0 g (23.6 mmol) of Compound A was dissolved in 100 ml of THF and then 10 mL (25.0 mmol, 2.5M in Hexane) of n-BuLi was slowly drop-wise added at a temperature of −78° C. After stirring at a temperature of −78° C. for 1 hour, 9.3 mL (50.0 mmol) of 2-isopropoxy (−4,4,5,5,-tetramethyl-1,3,2-dioxaborane) was slowly drop-wise added to prepare a reaction solution. The reaction mixture was stirred at a temperature of −78° C. for 1 hour and then additionally stirred at room temperature for 24 hours. After the reaction was completed, 50 mL of 10% of HCl aqueous solution and 50 mL of $H_2O$ were added thereto and then extracted 3 times with 80 mL of diethylether to collect an organic layer. The collected organic layer was dried with magnesium sulfate and then a solvent was evaporated therefrom to obtain residues, which were then isolated and purified using a silica gel column chromatography to obtain 9.34 g (yield 92%) Intermediate I-1. The compound produced was observed through LC-MS.

$C_{30}H_{27}BO_2$: calc. 430.21. found 430.25.

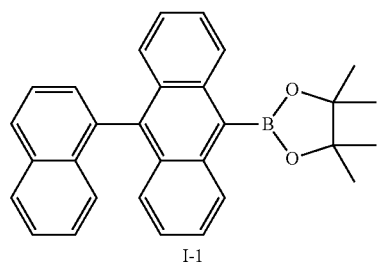

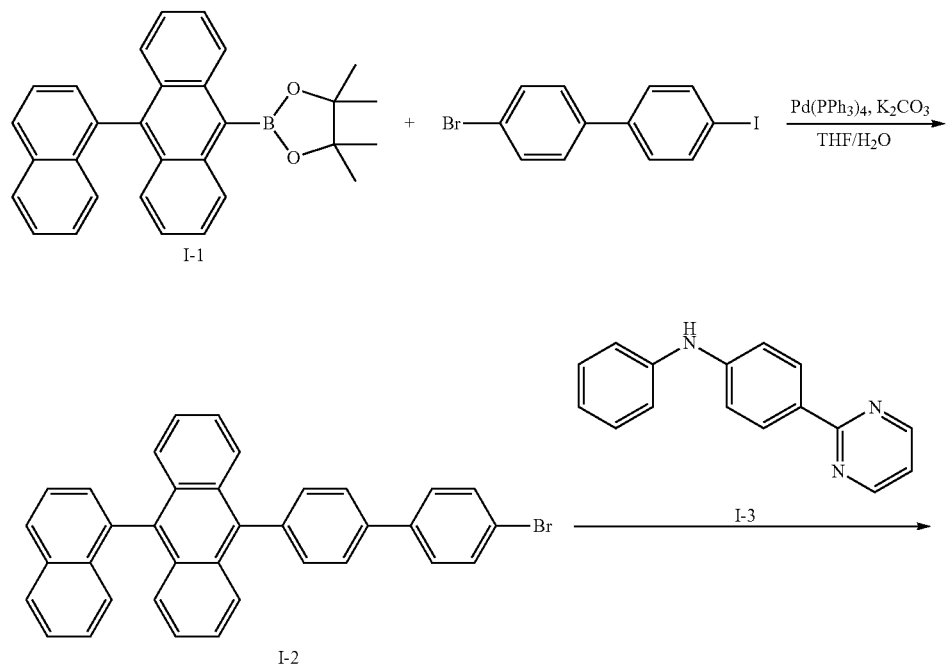

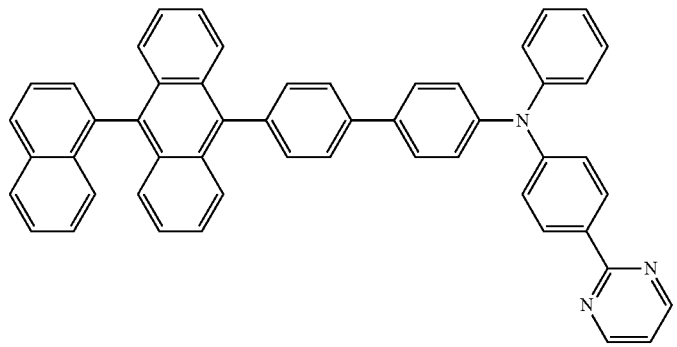

Synthesis of Compound 10

8.60 g (20.0 mmol) of Intermediate I-1, 7.18 g (20.0 mmol) of 4'-bromo-4-iodobenzene, 1.15 g (1.0 mmol) of Pd(PPh$_3$)$_4$, and 8.29 g (60.0 mmol) of K$_2$CO$_3$ were dissolved in 50 mL of a mixture solution of THF/H$_2$O (2/1) to prepare a reaction solution, which was then stirred at a temperature of 70° C. for 5 hours. After the reaction was completed, the reaction mixture was cooled to room temperature, then the reaction solution was extracted three times with 50 mL of water and 50 mL of diethylether to collect an organic layer. The collected organic layer was dried with magnesium sulfate and a solvent was evaporated therefrom to obtain residues, which were then isolated and purified by using a silica gel column chromatography to obtain 8.56 g (yield 80%) of Intermediate I-2.

5.34 g (10.0 mmol) of Intermediate I-2, 2.96 g (12.0 mmol) of Intermediate I-3, 0.18 g (0.2 mmol) of Pd$_2$(dba)$_3$, 0.04 g (0.4 mmol) of PtBu$_3$, and 1.44 g (15.0 mmol) of NaOtBu were dissolved in 50 mL of toluene to prepare a reaction solution, which was then refluxed for 3 hours. After the reaction was completed, the reaction solution was cooled to room temperature, the reaction solution was extracted three times with 40 mL of water and 40 mL of diethylether to collect an organic layer. The collected organic layer was dried with magnesium sulfate and a solvent was evaporated therefrom to obtain residues, which were then isolated and purified using a silica gel column chromatography to obtain 5.96 g (yield 85%) of Compound 10. The compound produced was observed through MS-FAB and $^1$H NMR.

C$_{52}$H$_{35}$N$_3$: calc. 701.28. found 701.30.

$^1$H NMR (CDCl$_3$, 400 MHz) δ (ppm) 8.48-8.45 (m, 2H), 7.94-7.90 (m, 1H), 7.83-7.77 (m, 5H), 7.74-7.65 (m, 5H), 7.55-7.52 (m, 1H), 7.48-7.44 (m, 4H), 7.38-7.25 (m, 7H), 7.09-7.05 (m, 2H), 6.98-6.91 (m, 3H), 6.86-6.82 (m, 2H), 6.66-6.63 (m, 1H), 6.23-6.19 (m, 2H)

Synthesis Example 2

Synthesis of Compound 1

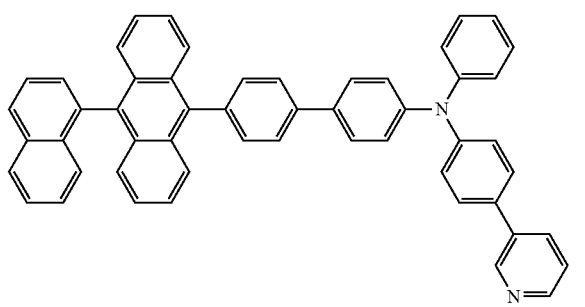

5.67 g (yield 81%) of Compound 1 was obtained by using the same method as in Compound 10 except for using Intermediate I-4 instead of Intermediate I-3. The compound produced was observed through MS-FAB and $^1$H NMR.

<Intermediate I-4>

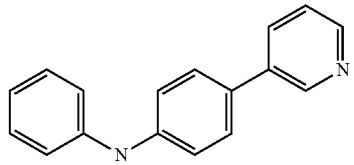

I-4

C$_{53}$H$_{36}$N$_2$: calc. 700.29. found 700.30.

$^1$H NMR (CDCl$_3$, 400 MHz) δ (ppm) 8.74 (dd, 1H), 8.51-8.48 (m, 1H), 7.94-7.90 (m, 1H), 7.83-7.77 (m, 5H), 7.74-7.65 (m, 6H), 7.55-7.52 (m, 1H), 7.48-7.44 (m, 4H), 7.38-7.25 (m, 7H), 7.09-7.05 (m, 2H), 6.98-6.91 (m, 3H), 6.86-6.82 (m, 2H), 6.66-6.63 (m, 1H), 6.23-6.19 (m, 2H)

Example 1

As a substrate and an anode, a Corning 15 Ω/cm$^2$ (1200 Å) ITO glass substrate was cut into a size of 50 mm×50 mm×0.7 mm, and then ultrasonically washed using isopropyl alcohol and ultrapure water for 5 minutes, followed by irradiation of UV and exposure to ozone for cleaning for about 30 minutes. The glass substrate was then loaded onto a vacuum deposition device.

4,4',4"-tris(2-naphthyl(phenyl)amino)triphenylamine (2-TNATA) was vacuum deposited on an ITO layer, which is an anode, to form an HIL having a thickness of 600 Å, and 4,4'-bis[N-(1-naphthyl)-N-phenylamino]biphenyl (hereinafter, NPB) was deposited on the HIL in a thickness of 300 Å to form an HTL.

9,10-di(naphthalene-2-yl)anthracene (hereinafter, ADN) was vacuum deposited on the HTL to form an EML having a thickness of 400 Å.

Then, Compound 1 (ETL1 material), Compound 15 (ETL2 material), and LiQ (EIL material) were vacuum co-deposited on the EML in a weight ratio of 25:25:50 to form an ETL having a thickness of 300 Å, then LiF was deposited on the ETL to form an EIL having a thickness of 10 Å, and then Al was deposited on the EIL to form a second electrode (cathode) having a thickness of 1100 Å to manufacture an organic light-emitting device.

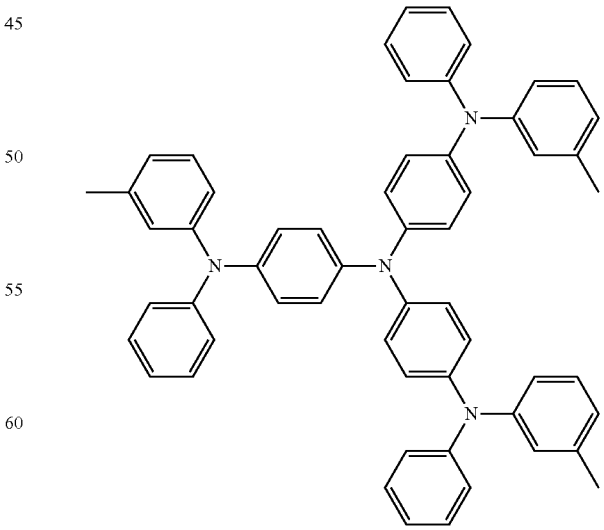

<2-TNATA>

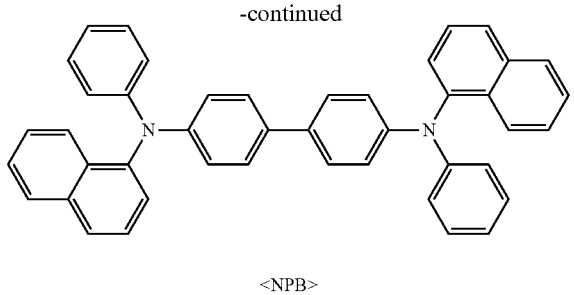

<NPB>

Example 2

An organic light-emitting device was manufactured in the same manner as in Example 1 except for vacuum co-depositing Compound 1 (ETL1 material) and Compound 15 (ETL2 material) and LiQ (EIL material) in a weight ratio of 25:25:50 instead of vacuum co-depositing Compound 1 (ETL1 material), Compound 15 (ETL2 material), and LiQ (EIL material) in a weight ratio of 15:15:70 when forming an HTL.

Comparative Example 1

An organic light-emitting device was manufactured in the same manner as in Example 1 except for vacuum co-depositing Compound 1 (ETL1 material) and LiQ (EIL material) in a weight ratio of 40:60 instead of vacuum co-depositing Compound 1 (ETL1 material), Compound 15 (ETL2 material), and LiQ (EIL material) in a weight ratio of 25:25:50 when forming an HTL.

Comparative Example 2

An organic light-emitting device was manufactured in the same manner as in Example 1 except for depositing only Compound 1 (ETL1 material) when forming an HTL.

Comparative Example 3

An organic light-emitting device was manufactured in the same manner as in Example 1 except for vacuum co-depositing Compound 201 and Compound LiQ (EIL material) in a weight ratio of 40:60 to form an HTL having a thickness of 360 Å when forming an HTL.

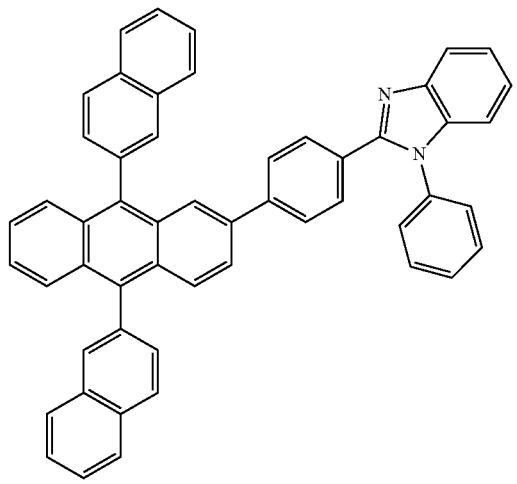

<Compound 201>

Evaluation Example

Driving voltage, current density, efficiency, and color purity of organic light-emitting devices of Examples 1 and 2, and Comparative Examples 1 and 2 were measured and evaluated by supplying power from a current voltmeter (Keithley SMU 236) and using a spectrophotometer, PR650 Spectroscan Source Measurement Unit (available from PhotoResearch). Results are shown in Table 1 (T95 lifespan is time taken until brightness is reduced to 95% when an initial brightness measured under a current condition of 10 mA/cm$^2$ is 100%)

TABLE 1

|  | ETL material (weight ratio) | Driving voltage (V) | Current density (mA/cm$^2$) | efficiency (cd/A) | Color coordinates CIE x | CIE y | T95 lifespan [hr] |
|---|---|---|---|---|---|---|---|
| Example 1 | ETL1:ETL2:EIL = 25:25:50 | 3.8 | 9.5 | 6.1 | 0.136 | 0.055 | 200 |
| Example 2 | ETL1:ETL2:EIL = 15:15:70 | 3.7 | 10.5 | 5.8 | 0.138 | 0.057 | 92 |
| Comparative Example 1 | ETL1:EIL = 40:60 | 3.8 | 11.1 | 5.5 | 0.140 | 0.041 | 40 |
| Comparative Example 2 | ETL1 = 100 | 3.6 | 11.9 | 6 | 0.138 | 0.055 | 10 |
| Comparative Example 3 | Compound 201:LiQ = 40:60 | 3.8 | 8.5 | 5 | 0.141 | 0.05 | 55 |

Referring to Table 1, the organic light-emitting devices of Examples 1 and 2 have a long lifespan without increasing driving voltage and decreasing efficiency compared to the organic light-emitting devices of Comparative Examples 1 to 3.

The organic light-emitting device may have low driving voltage, high efficiency, as well as a long lifespan.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present disclosure as set forth in the following claims.

What is claimed is:

1. An organic light-emitting device, comprising:
a first electrode;
a second electrode disposed opposite to the first electrode;
an emission layer disposed between the first electrode and the second electrode; and
an electron-transporting layer disposed between the emission layer and the second electrode; wherein
the electron-transporting layer includes a first electron-transporting material and a second electron-transporting material; and
a lowest unoccupied molecular orbital (LUMO) energy level of the first electron-transporting material ($EL_1$) and a lowest unoccupied molecular orbital (LUMO) energy level of the second electron-transporting material ($EL_2$) satisfy the equation $0.1\ eV \leq |EL_1-EL_2| \leq 0.3\ eV$,
wherein the first electron-transporting material and the second electron-transporting material are each independently selected from an amine-based compound represented by Formula 1 and an anthracene-based compound represented by Formula 2:

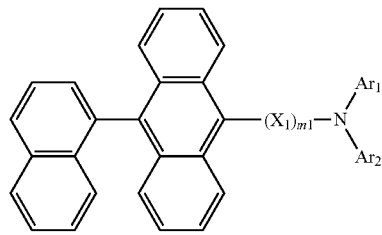

<Formula 1>

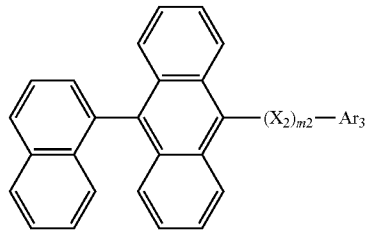

<Formula 2> wherein in Formulae 1 and 2, groups represented by $X_1$ and $X_2$ are each independently selected from a substituted or unsubstituted $C_6$-$C_{60}$ arylene group and a substituted or unsubstituted $C_2$-$C_{60}$ heteroarylene group;

m1 and m2 are each independently an integer of 0 to 5;

groups represented by $Ar_1$ and $Ar_2$ are each independently selected from a substituted or unsubstituted $C_6$-$C_{60}$ aryl group and a substituted or unsubstituted $C_2$-$C_{60}$ heteroaryl group; wherein at least one of the groups represented by $Ar_1$ and $Ar_2$ is selected from i) a pyridyl group, a pyrimidyl group, and a triazinyl group, ii) a pyridyl group, a pyrimidyl group, and a triazinyl group each substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group each substituted with at least one of a pyridyl group, a pyrimidyl group, and a triazinyl group; and iv) a pyridyl group, a pyrimidyl group, and a triazinyl group each substituted with at least one of a $C_6$-$C_{60}$ aryl group and a $C_2$-$C_{60}$ heteroaryl group, which are each substituted with at least one of a $C_6$-$C_{60}$ aryl group and a $C_2$-$C_{60}$ heteroaryl group; and a group represented by $Ar_3$ is selected from i) a pyridyl group, a pyrimidyl group, and a triazinyl group, ii) a pyridyl group, a pyrimidyl group, and a triazinyl group each substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group each substituted with at least one of a pyridyl group, a pyrimidyl group, and a triazinyl group; and iv) a pyridyl group, a pyrimidyl group, and a triazinyl group each substituted with at least one of a $C_6$-$C_{60}$ aryl group and a $C_2$-$C_{60}$ heteroaryl group, which are each substituted with at least one of a $C_6$-$C_{60}$ aryl group and a $C_2$-$C_{60}$ heteroaryl group.

2. The organic light-emitting device as claimed in claim 1, wherein a highest occupied molecular orbital (HOMO) energy level of the first electron-transporting material ($EH_1$) and the lowest unoccupied molecular orbital (LUMO) energy level of the first electron-transporting material ($EL_1$) satisfy the equation $2.7\ eV \leq |EL_1-EH_1| \leq 3.2\ eV$; and a highest occupied molecular orbital (HOMO) of the second electron-transporting material ($EH_2$) and the lowest unoccupied molecular orbital (LUMO) energy level of the second electron-transporting material ($EL_2$) satisfy the equation, $2.7\ eV \leq |EL_2-EH_2| \leq 3.2\ eV$.

3. The organic light-emitting device as claimed in claim 1, wherein a molecular weight of the first electron-transporting material ($MW_1$) and a molecular weight of the second electron-transporting material ($MW_2$) satisfy the equation, $|MW_1-MW_2|\leq 30$.

4. The organic light-emitting device as claimed in claim 1, wherein both of the first electron-transporting material and the second electron-transporting material are each non-metal-atom-containing organic compounds.

5. The organic light-emitting device as claimed in claim 1, wherein the first electron-transporting material and the second electron-transporting material are each independently selected from a pyridine derivative, a pyrimidine derivative, and a triazine derivative.

6. The organic light-emitting device as claimed in claim 1, wherein:
the LUMO energy level of the $EL_1$ satisfies the equation $2.6\ eV\leq|EL_1|\leq 2.9\ eV$; and
the LUMO energy level of the $EL_2$ satisfies the equation $2.7\ eV\leq|EL_1|\leq 3.0\ eV$.

7. The organic light-emitting device as claimed in claim 1, wherein the first electron-transporting material and the second electron-transporting material are each independently selected from Compounds 1 to 15:

<Compound 1>

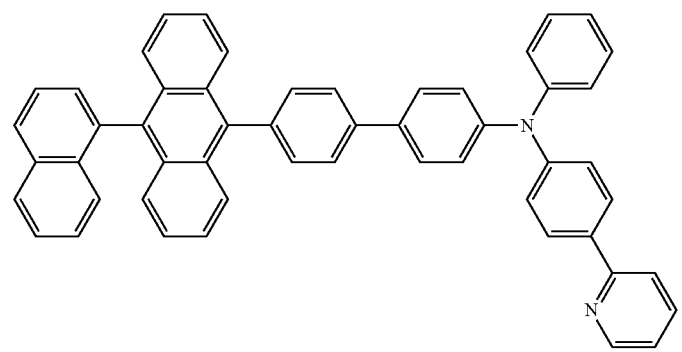

<Compound 2>

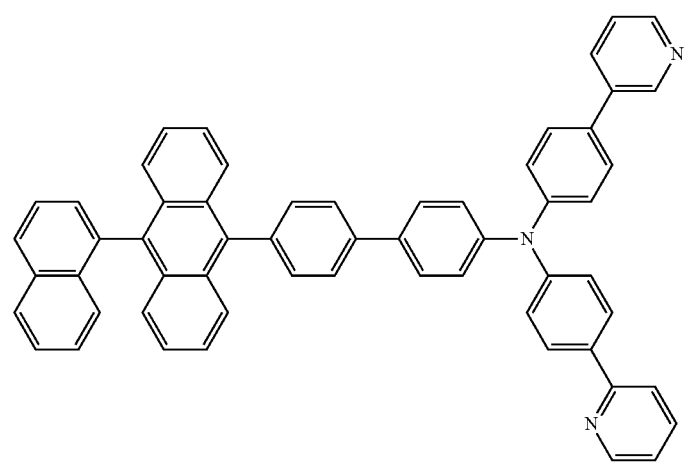

<Compound 3>

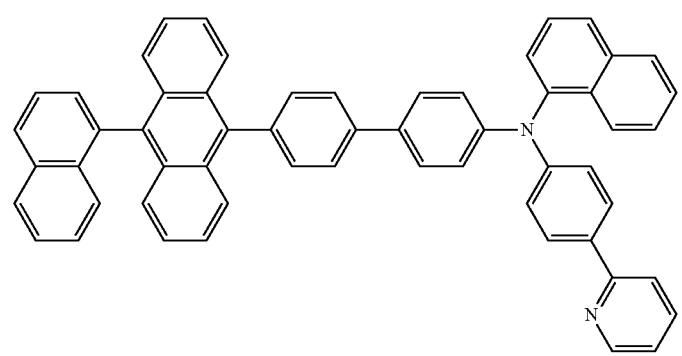

<Compound 4>
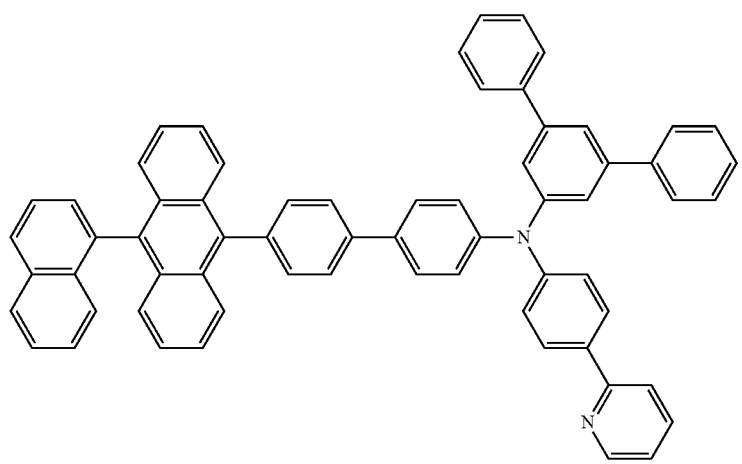
<Compound 5>
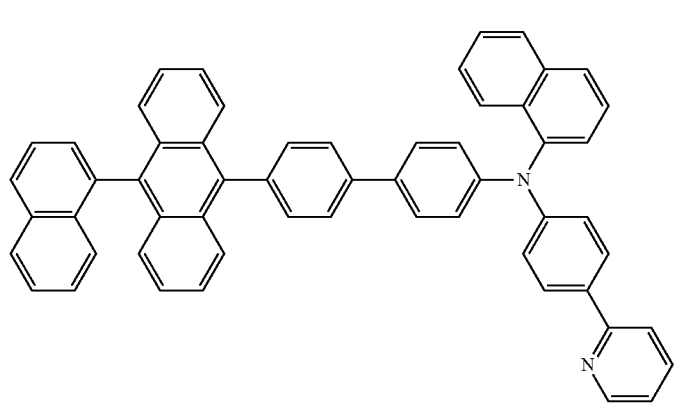
<Compound 6>
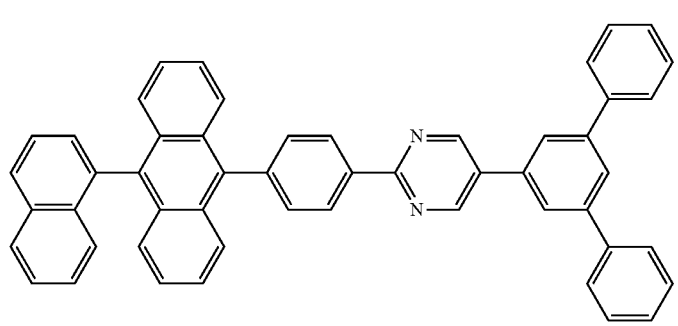
<Compound 7>
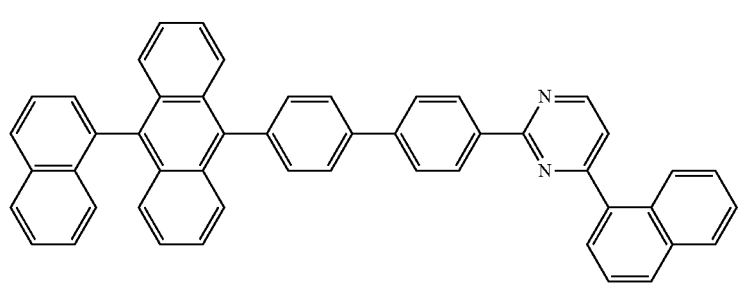

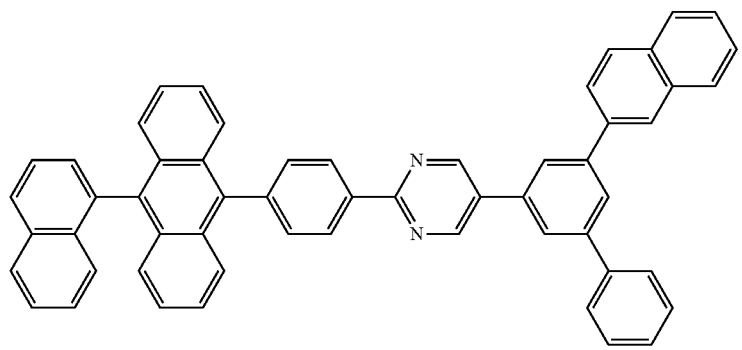
<Compound 8>
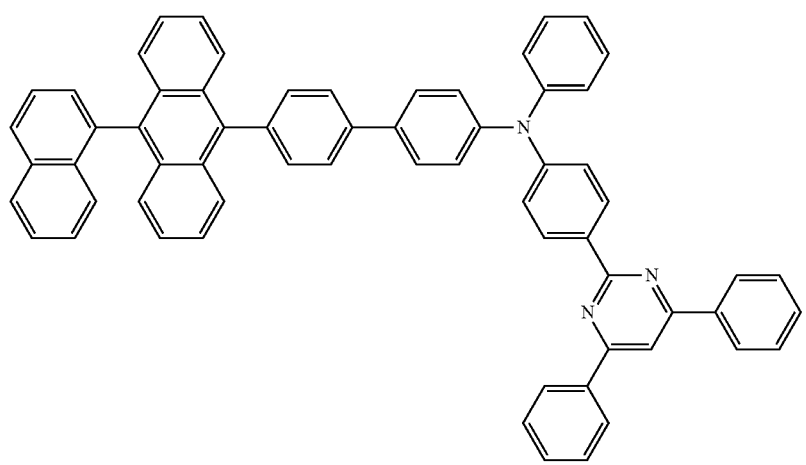
<Compound 9>
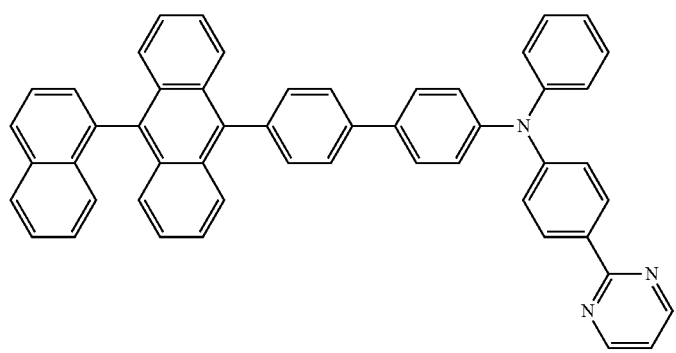
<Compound 10>
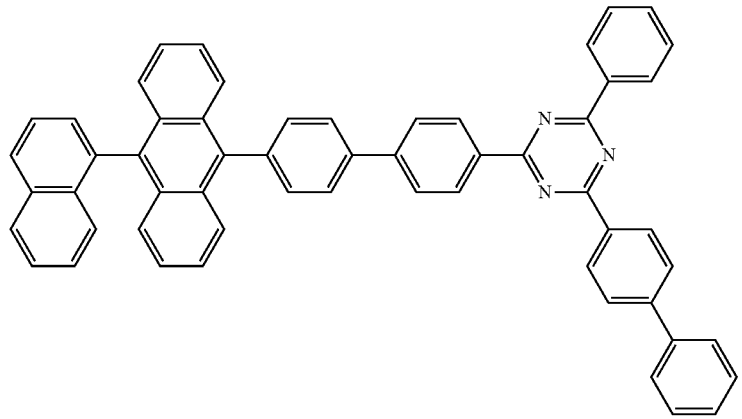
<Compound 11>

<Compound 12>
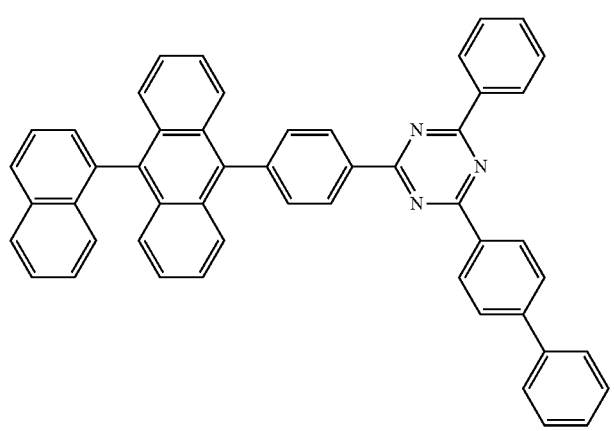
<Compound 13>
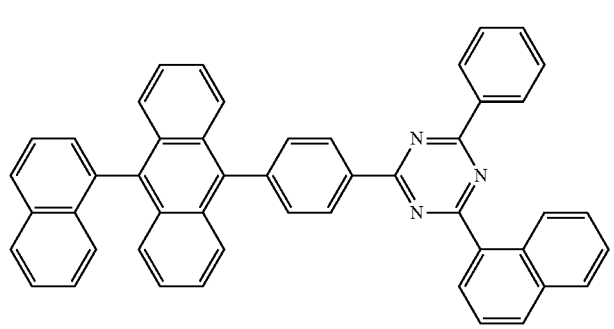
<Compound 14>
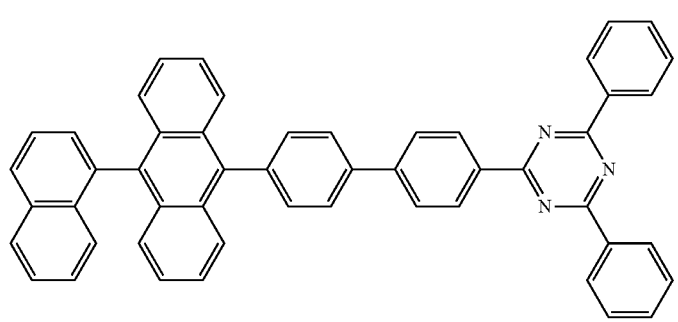
<Compound 15>
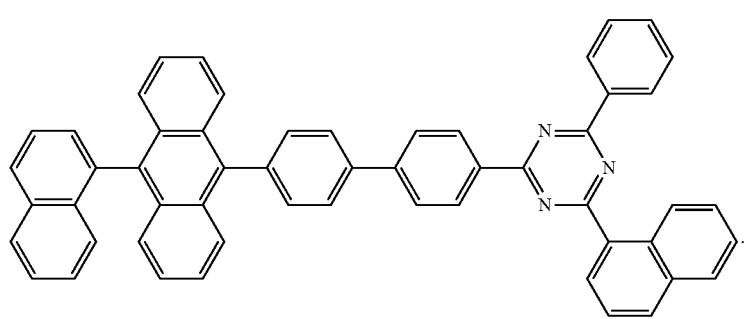

8. An organic light-emitting device, comprising:
a first electrode;
a second electrode disposed opposite to the first electrode;
an emission layer disposed between the first electrode and the second electrode; and
an electron-transporting layer disposed between the emission layer and the second electrode, wherein
the electron-transporting layer includes a first electron-transporting material and a second electron-transporting material,
the first electron-transporting material and the second electron-transporting material are each independently selected from an amine-based compound represented by Formula 1 and an anthracene-based compound represented by Formula 2,
the first electron-transporting material and the second electron-transporting material are different:

<Formula 1>

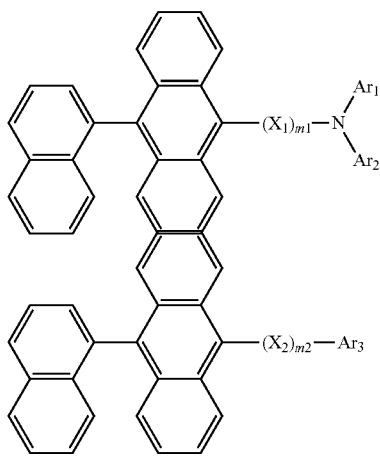

<Formula 2>

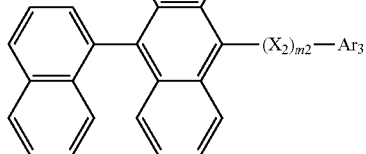

wherein Formulae 1 and 2, groups represented by $X_1$ and $X_2$ are each independently selected from a substituted or unsubstituted $C_6$-$C_{60}$ arylene group and a substituted or unsubstituted $C_2$-$C_{60}$ heteroarylene group;
m1 and m2 are each independently an integer of 0 to 5;
groups represented by $Ar_1$ and $Ar_2$ are each independently selected from a substituted or unsubstituted $C_6$-$C_{60}$ aryl group and a substituted or unsubstituted $C_2$-$C_{60}$ heteroaryl group; wherein
at least one of the groups represented by $Ar_1$ and $Ar_2$ is selected from i) a pyridyl group, a pyrimidyl group, and a triazinyl group, ii) a pyridyl group, a pyrimidyl group, and a triazinyl group each substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group each substituted with at least one of a pyridyl group, a pyrimidyl group, and a triazinyl group; and iv) a pyridyl group, a pyrimidyl group, and a triazinyl group each substituted with at least one of a $C_6$-$C_{60}$ aryl group and a $C_2$-$C_{60}$ heteroaryl group, which are each substituted with at least one of a $C_6$-$C_{60}$ aryl group and a $C_2$-$C_{60}$ heteroaryl group; and
a group represented by $Ar_3$ is selected from i) a pyridyl group, a pyrimidyl group, and a triazinyl group, ii) a pyridyl group, a pyrimidyl group, and a triazinyl group each substituted with at least one of a $C_6$-$C_{60}$ aryl group and a $C_2$-$C_{60}$ heteroaryl group; iii) a $C_6$-$C_{60}$ aryl group and a $C_2$-$C_{60}$ heteroaryl group each substituted with at least one of a pyridyl group, a pyrimidyl group, and a triazinyl group; and iv) a pyridyl group, a pyrimidyl group, and a triazinyl group each substituted with at least one of a $C_6$-$C_{60}$ aryl group and a $C_2$-$C_{60}$ heteroaryl group, which are each substituted with at least one of a $C_6$-$C_{60}$ aryl group and a $C_2$-$C_{60}$ heteroaryl group.

9. The organic light-emitting device as claimed in claim 8, wherein groups represented by $X_1$ and $X_2$ are each independently selected from a substituted or unsubstituted a phenylene group, a substituted or unsubstituted a naphthylene group, a substituted or unsubstituted an anthrylene group, a substituted or unsubstituted pyridinylene group, a substituted or unsubstituted pyrimidinylene group, and a substituted or unsubstituted triazolylene group.

10. The organic light-emitting device as claimed in claim 8, wherein m1 and m2 are each independently an integer of 1 or 2.

11. The organic light-emitting device as claimed in claim 8, wherein moieties represented by $(X_1)_{m1}$ and $(X_2)_{m2}$ are each independently selected from Formulae 3-1 to 3-4:

3-1
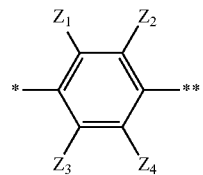

3-2
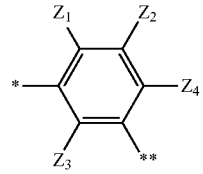

3-3
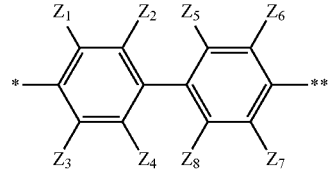

3-4
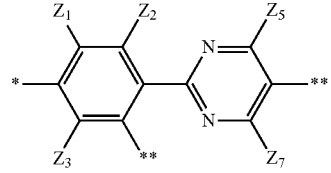

wherein groups represented by $Z_1$ to $Z_8$ are each independently selected from a hydrogen atom; a deuterium atom; —F; —Cl; —Br; —I; —CN; a hydroxyl group; —NO$_2$; a $C_1$-$C_{20}$ alkyl group; a $C_1$-$C_{20}$ alkoxy group; a $C_1$-$C_{20}$ alkyl group and a $C_1$-$C_{20}$ alkoxy group each substituted with at least one of a deuterium atom, —F, —Cl, —Br, —I, —CN, a hydroxyl group, and —NO$_2$; a $C_6$-$C_{20}$ aryl group; a $C_2$-$C_{20}$ heteroaryl group; and a $C_6$-$C_{20}$ aryl group and a $C_2$-$C_{20}$ heteroaryl group each substituted with at least one of a deuterium atom, —F, —Cl, —Br, —I, —CN, a hydroxyl group, —NO$_2$, a $C_1$-$C_{20}$ alkyl group, a $C_1$-$C_{20}$ alkoxy group, a $C_6$-$C_{20}$ aryl group, and a $C_2$-$C_{20}$ heteroaryl group;
* is a bonding site to anthracene of Formulae 1 and 2; and
** is a bonding site to a nitrogen atom of Formula 1 or a bonding site to a group represented by $Ar_3$ of Formula 2.

12. The organic light-emitting device as claimed in claim 8, wherein groups represented by $Ar_1$ and $Ar_2$ are each independently represented by any one selected from Formulae 4-1 to 4-9, provided that at least one of groups represented by $Ar_1$ and $Ar_e$ is represented by any one of Formulae 4-1 to 4-6:

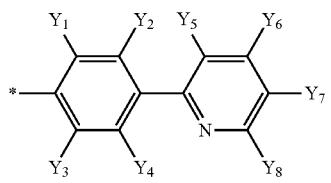
4-1

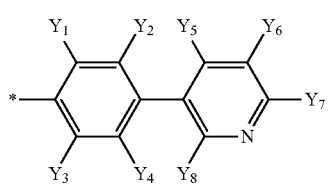
4-2

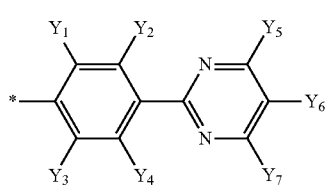
4-3

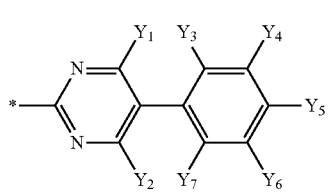
4-4

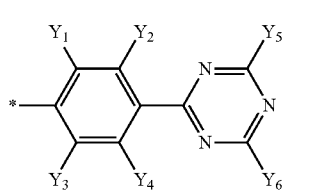
4-5

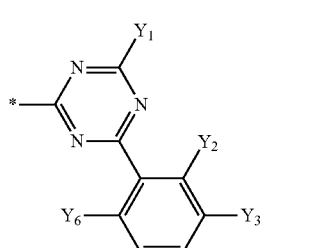
4-6

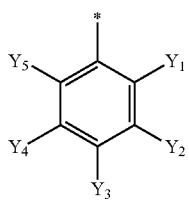
4-7

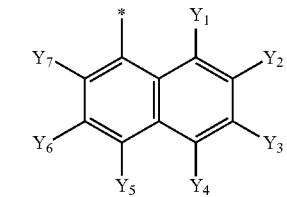
4-8

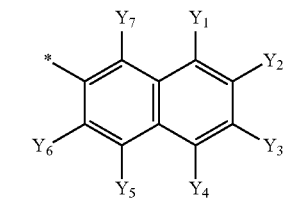
4-9 wherein groups represented by $Y_1$ to $Y_8$ are each independently selected from a hydrogen atom, a phenyl group, a naphthyl group, a pyridyl group, a pyrimidyl group and a triazinyl group; wherein

* is a bonding site to a nitrogen atom of Formula 1.

13. The organic light-emitting device as claimed in claim 8, wherein a group represented by $Ar_3$ is selected from i) a pyridyl group, a pyrimidyl group, and a triazinyl group; ii) a pyridyl group, a pyrimidyl group, and a triazinyl group each substituted with at least one of a phenyl group, a naphthyl group, a pyridyl group, a pyrimidyl group, and a triazinyl group; iii) a phenyl group, a naphthyl group, a pyridyl group, a pyrimidyl group, and a triazinyl group each substituted with at least one of a pyridyl group, a pyrimidyl group, and a triazinyl group; and iv) a pyridyl group, a pyrimidyl group, and a triazinyl group each substituted with at least one of a phenyl group, a naphthyl group, a pyridyl group, a pyrimidyl group, and a triazinyl group, which are each substituted with at least one of a phenyl group, a naphthyl group, a pyridyl group, a pyrimidyl group, and a triazinyl group.

14. The organic light-emitting device as claimed in claim 8, wherein a group represented by $Ar_3$ is represented by any one of Formulae 4-1 to 4-6:

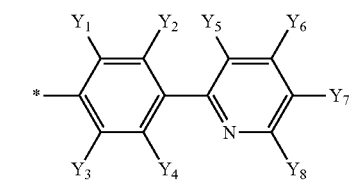
4-1

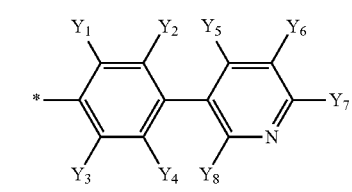
4-2

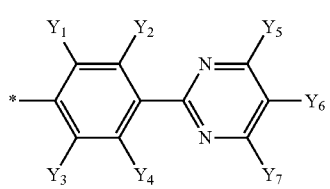

4-3

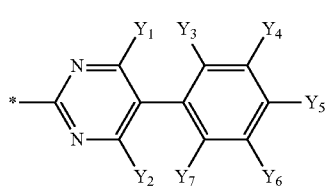

4-4

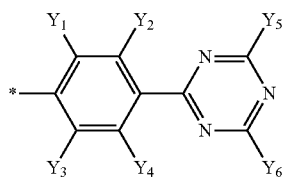

4-5

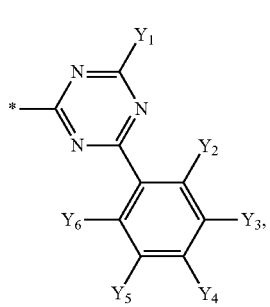

4-6 wherein groups represented by $Y_1$ to $Y_8$ are each independently selected from a hydrogen atom, a phenyl group, a naphthyl group, a pyridyl group, a pyrimidyl group, and a triazinyl group; and * is a bonding site to a nitrogen atom of Formula 1.

15. The organic light-emitting device as claimed in claim 8, wherein the first electron-transporting material and the second electron-transporting material are each independently selected from Compounds 1 to 15:

<Compound 1>

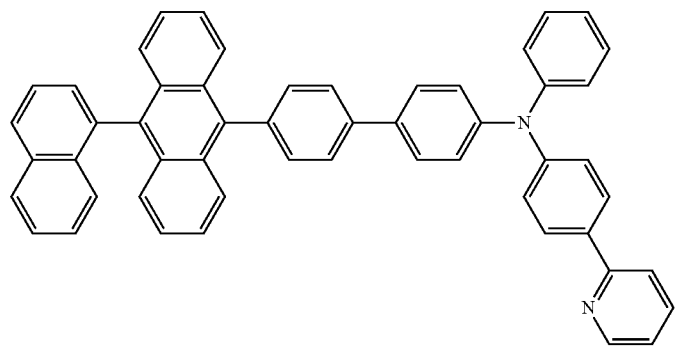

<Compound 2>

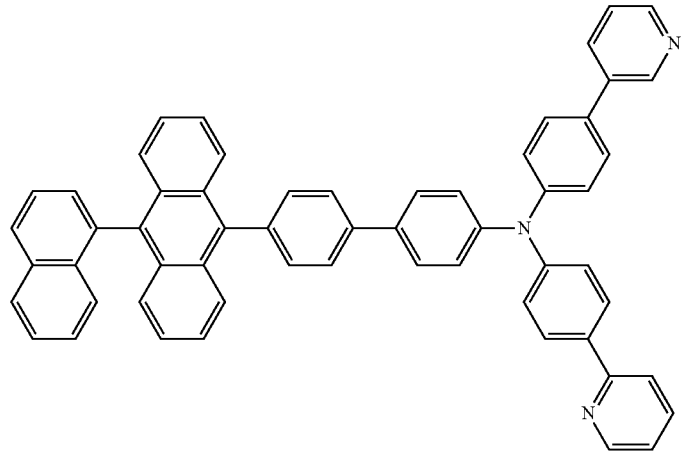

<Compound 3>
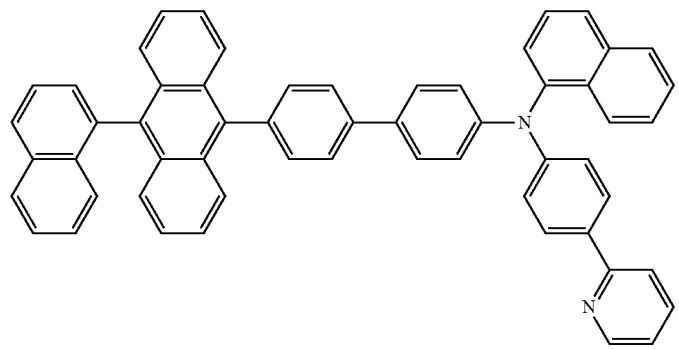
<Compound 4>
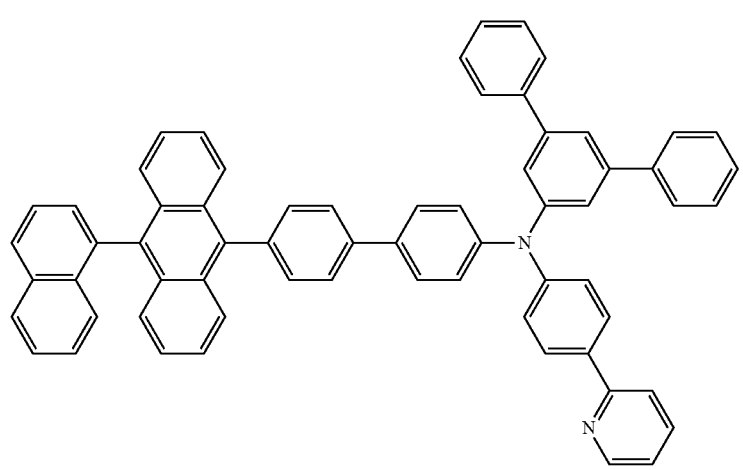
<Compound 5>
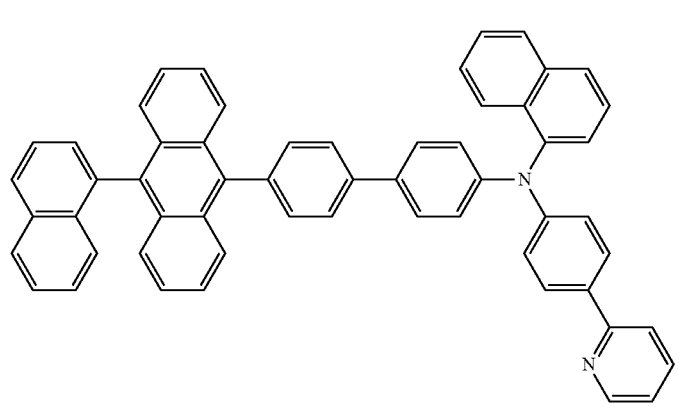
<Compound 6>
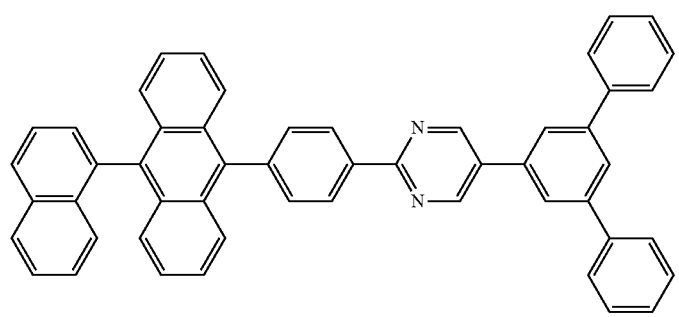

<Compound 7>
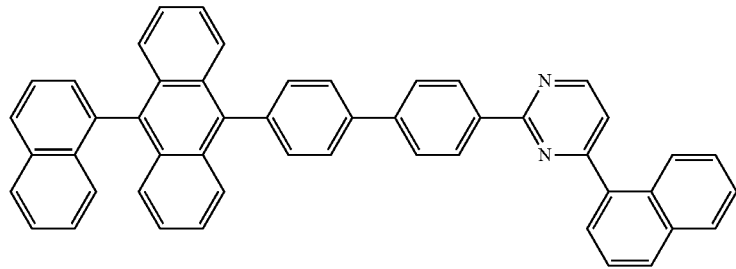
<Compound 8>
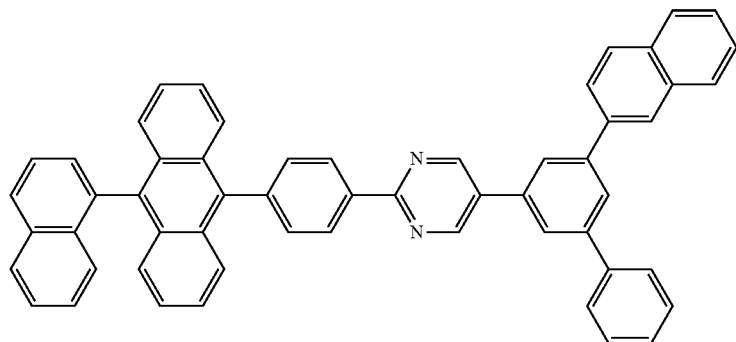
<Compound 9>
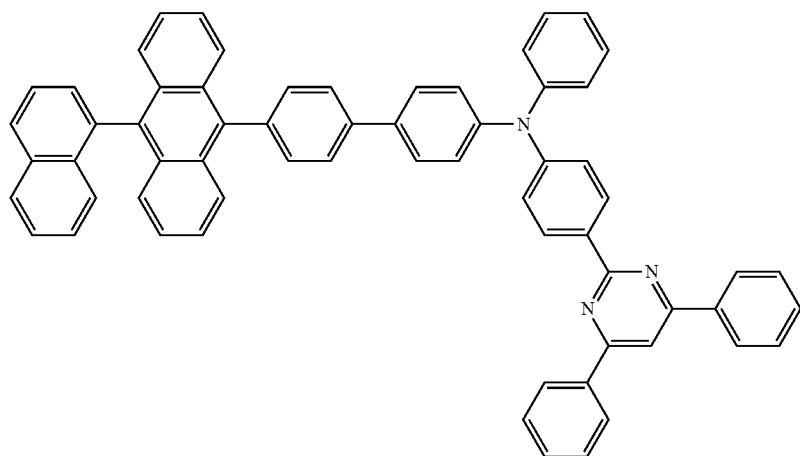
<Compound 10>
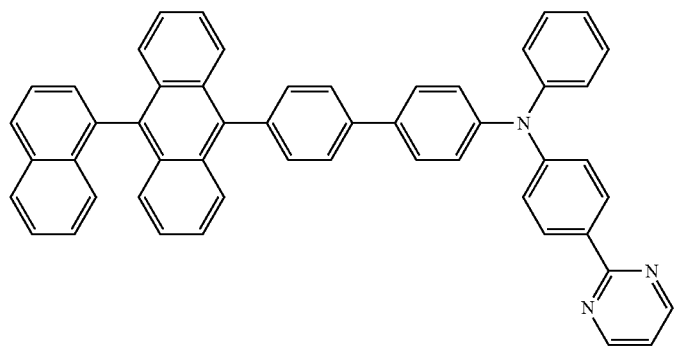

<Compound 11>
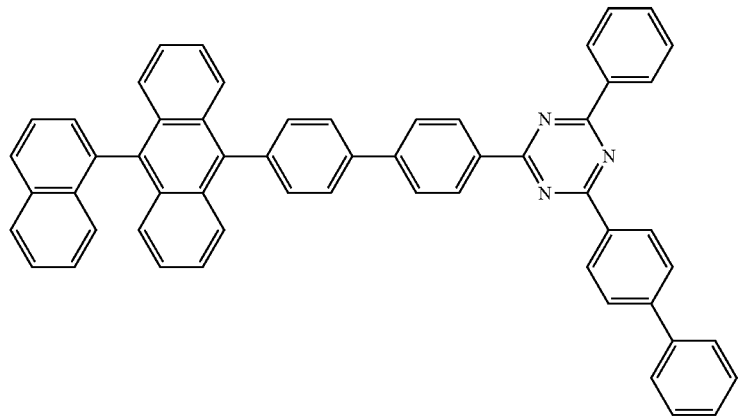
<Compound 12>
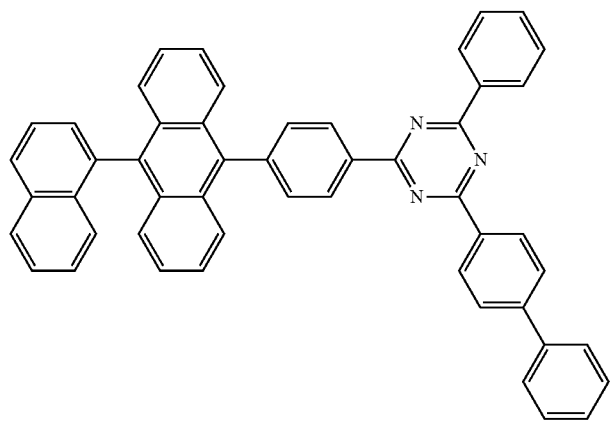
<Compound 13>
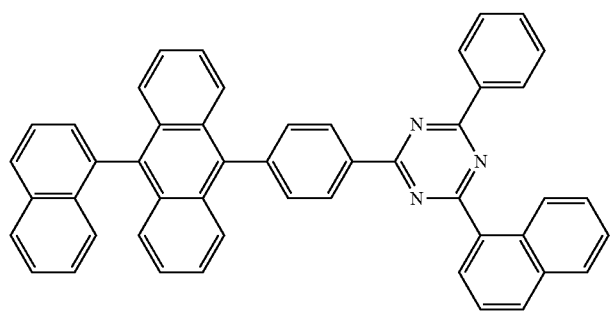
<Compound 14>
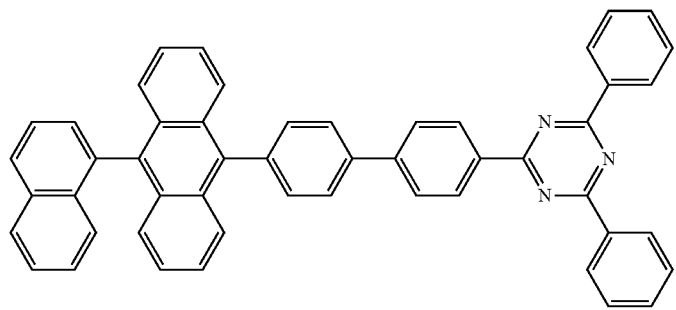

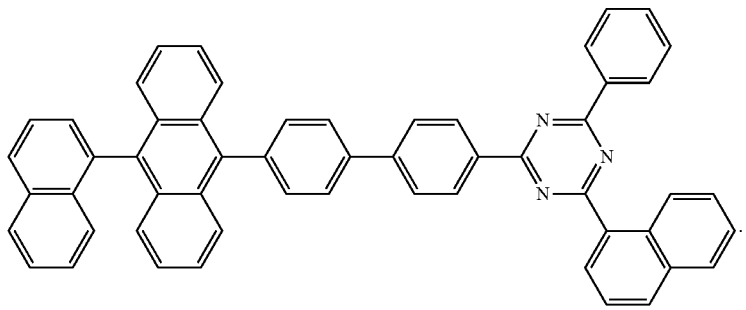

<Compound 15>

16. The organic light-emitting device as claimed in claim 8, wherein a lowest unoccupied molecular orbital energy level (LUMO) of the first electron-transporting material ($EL_1$) and a lowest unoccupied molecular orbital (LUMO) energy level of the second electron-transporting material ($EL_2$) satisfy the equation, $0.1\ eV \le |EL_1 - EL_2| \le 0.3\ eV$.

17. The organic light-emitting device as claimed in claim 16, wherein:
the LUMO energy level of the $EL_1$ satisfies the equation $2.6\ eV \le |EL_1| \le 2.9\ eV$; and
the LUMO energy level of the $EL_2$ satisfies the equation $2.7\ eV \le |EL_1| \le 3.0\ eV$.

18. The organic light-emitting device as claimed in claim 8, wherein a highest occupied molecular orbital (HOMO) energy level of the first electron-transporting material ($EH_1$) and a lowest unoccupied molecular orbital (LUMO) energy level of the first electron-transporting material ($EL_1$) satisfy the equation, $2.7\ eV \le |EL_1 - EH_1| \le 3.2\ eV$; and
a highest occupied molecular orbital (HOMO) energy level of the second electron-transporting material ($EH_2$) and a lowest unoccupied molecular orbital (LUMO) of the second electron-transporting material ($EL_2$) satisfy $2.7\ eV \le |EL_2 - EH_2| \le 3.2\ eV$.

19. The organic light-emitting device as claimed in claim 8, wherein:
i) the first electron-transporting material is at least one selected from amine-based compounds represented by Formula 1 and the second electron-transporting material is at least one selected from the amine-based compounds represented by Formula 1;
ii) the first electron-transporting material is at least one selected from the amine-based compounds represented by Formula 1 and the second electron-transporting material is at least one selected from anthracene-based compounds represented by Formula 2; or
iii) the first electron-transporting material is at least one selected from the anthracene-based compounds represented by Formula 2 and the second electron-transporting material is at least one selected from the anthracene-based compounds represented by Formula 2.

20. The organic light-emitting device as claimed in claim 8, wherein:
i) the first electron-transporting material and the second electron-transporting material are each independently at least one selected from Compounds 1 to 5;
ii) the first electron-transporting material is at least one selected from Compounds 1 to 5 and the second electron-transporting material is at least one selected from Compounds 6 to 10;
iii) the first electron-transporting material is at least one selected from Compounds 1 to 5 and the second electron-transporting material is at least one selected from Compounds 11 to 15;
iv) the first electron-transporting material and the second electron-transporting material are each independently at least one selected from Compounds 6 to 10;
v) the first electron-transporting material is at least one selected from Compounds 6 to 10 and the second electron-transporting material is at least one selected from Compounds 11 to 15; or
vi) the first electron-transporting material and the second electron-transporting material are each independently at least one selected from Compounds 11 to 15,

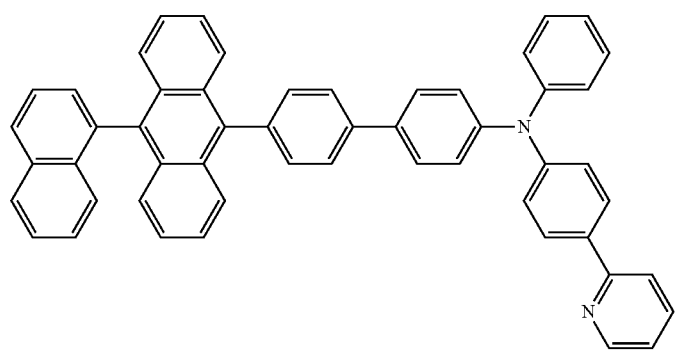

<Compound 1>

<Compound 2>
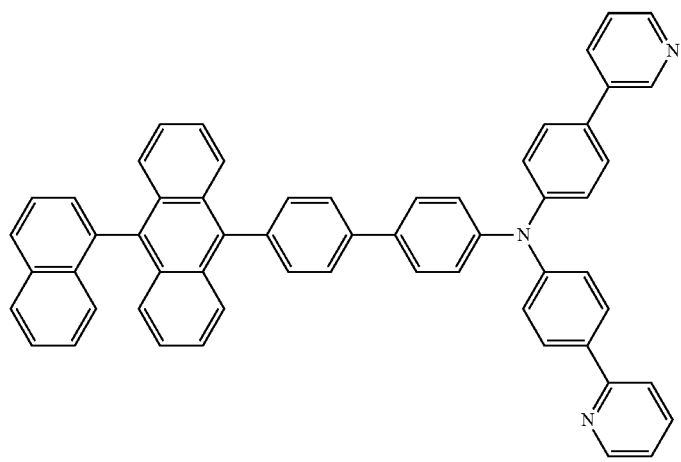
<Compound 3>
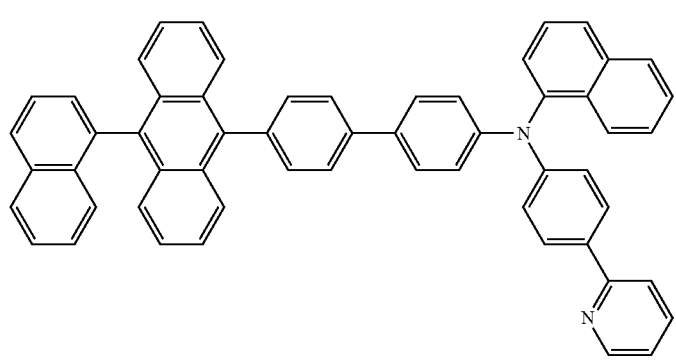
<Compound 4>
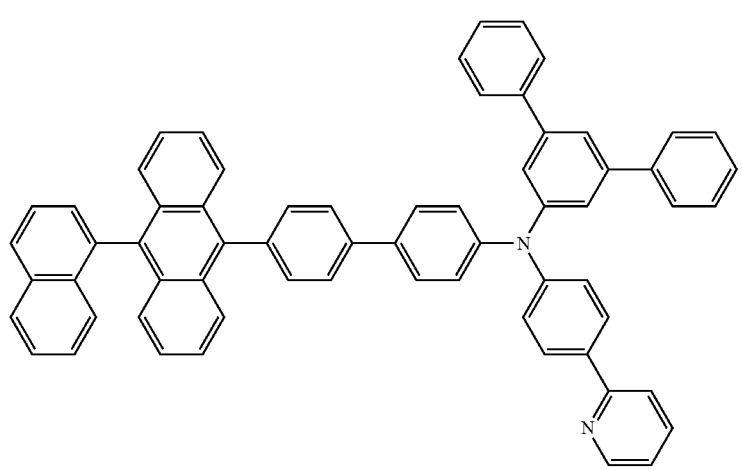
<Compound 5>
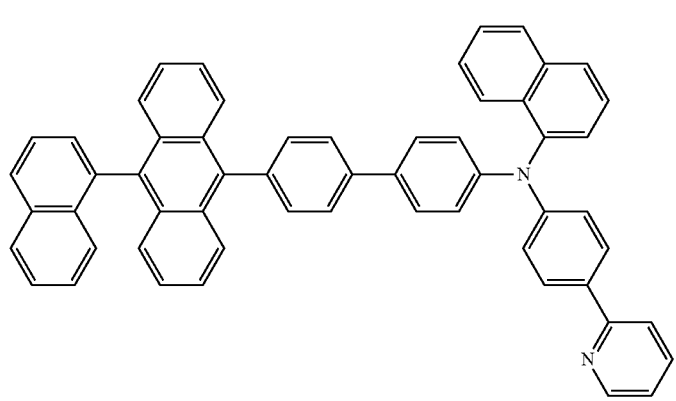

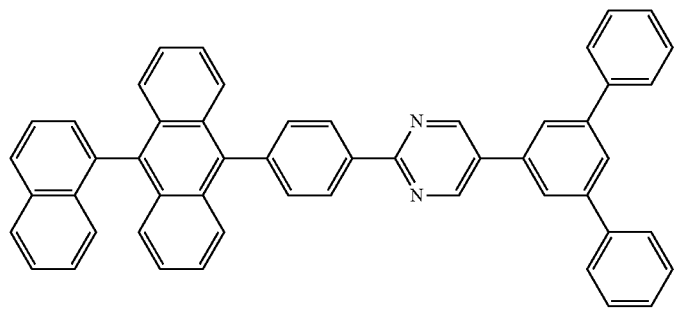
<Compound 6>
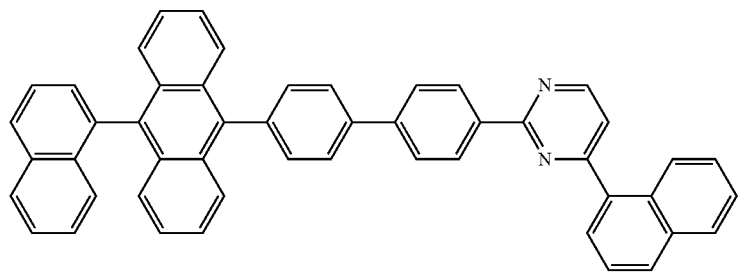
<Compound 7>
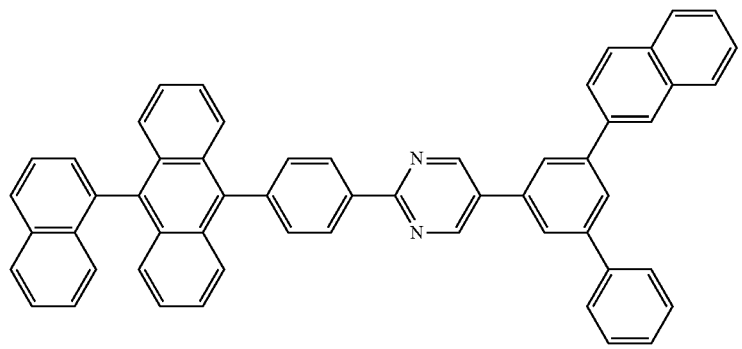
<Compound 8>
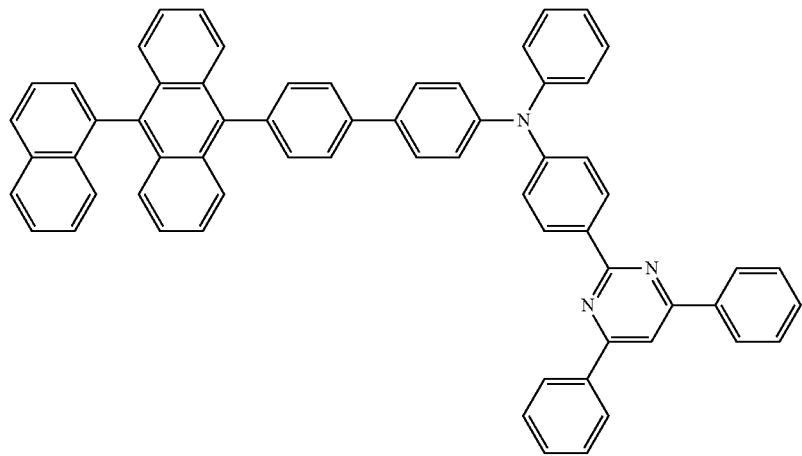
<Compound 9>

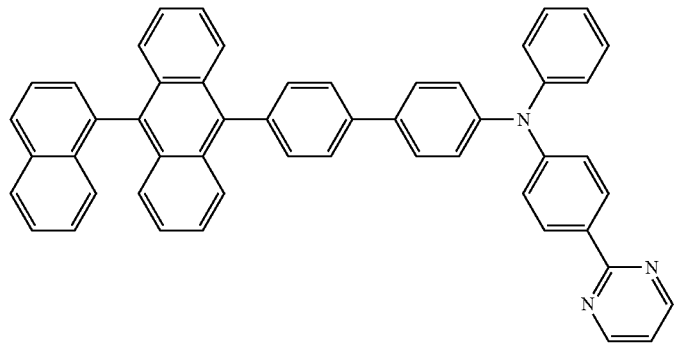
<Compound 10>
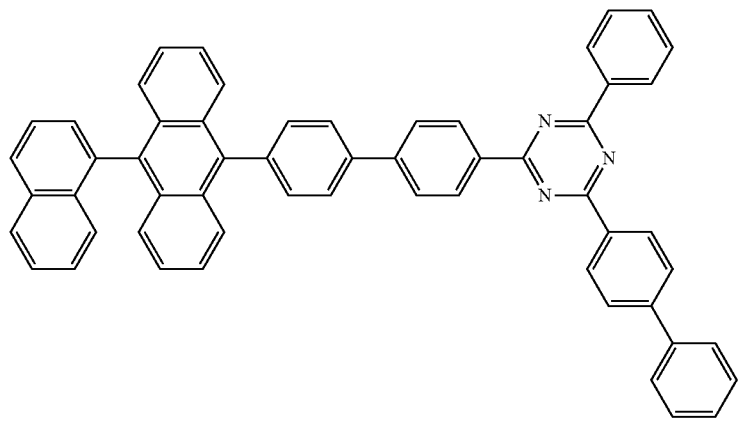
<Compound 11>
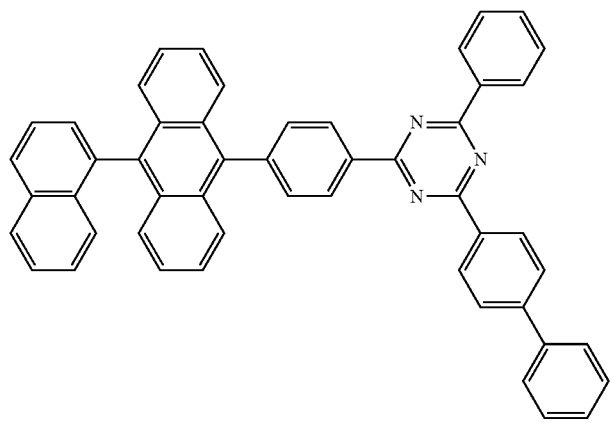
<Compound 12>
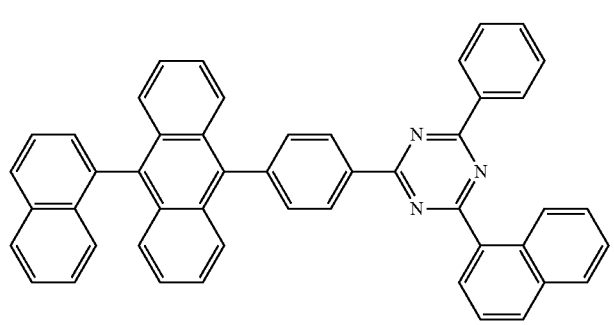
<Compound 13>

<Compound 14>
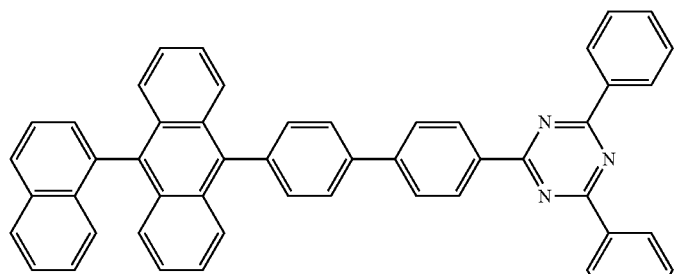
<Compound 15>
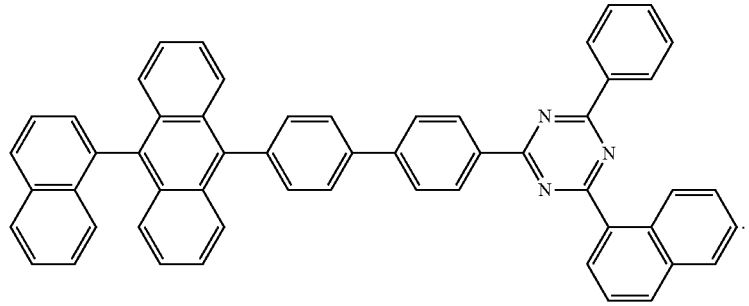
* * * * *